(12) United States Patent
Brown et al.

(10) Patent No.: US 7,538,141 B2
(45) Date of Patent: May 26, 2009

(54) COMPOUNDS FOR THE TREATMENT OF DISEASES

(76) Inventors: Alan Daniel Brown, Ramsgate Road, Sandwich, Kent (GB) CT13 9NJ; Mark Edward Bunnage, Ramsgate Road, Sandwich, Kent (GB) CT13 9NJ; Charlotte Alice Louise Lane, Ramsgate Road, Sandwich, Kent (GB) CT13 9NJ; Russell Andrew Lewthwaite, Ramsgate Road, Sandwich, Kent (GB) CT13 9NJ; Paul Alan Glossop, Ramsgate Road, Sandwich, Kent (GB) CT13 9NJ; Kim James, Ramsgate Road, Sandwich, Kent (GB) CT13 9NJ; David Anthony Price, Ramsgate Road, Sandwich, Kent (GB) CT13 9NJ ( * ) Notice: Subject to any disclaimer, the term of this patent is extended or adjusted under 35 U.S.C. 154(b) by 355 days.

(21) Appl. No.: 11/086,132

(22) Filed: Mar. 21, 2005

(65) Prior Publication Data

US 2005/0222128 A1    Oct. 6, 2005

Related U.S. Application Data

(60) Provisional application No. 60/591,789, filed on Jul. 27, 2004, provisional application No. 60/618,153, filed on Oct. 12, 2004, provisional application No. 60/625,505, filed on Nov. 5, 2004.

(30) Foreign Application Priority Data

Mar. 23, 2004    (EP)    ................... 04290769
Sep. 21, 2004    (GB)    ................... 0420867.4

(51) Int. Cl.
  C07C 233/00    (2006.01)
  C07C 235/00    (2006.01)
  C07C 237/00    (2006.01)
  C07C 239/00    (2006.01)
  A01N 37/18    (2006.01)
  A61K 31/16    (2006.01)

(52) U.S. Cl. ...................................... 514/613; 564/123
(58) Field of Classification Search ........................ None
  See application file for complete search history.

(56) References Cited

U.S. PATENT DOCUMENTS

| 4,160,036 A | 7/1979 | Bradshaw et al. ........... 424/330 |
| 4,460,580 A | 7/1984 | Ostermayer et al. ......... 424/232 |
| 6,106,864 A | 8/2000 | Dolan et al. ................. 424/488 |

FOREIGN PATENT DOCUMENTS

| EP | 0654534 | 5/1995 |
| FR | 2746395 | 9/1997 |
| WO | WO 9111172 | 8/1991 |
| WO | WO 9402518 | 2/1994 |
| WO | WO 9855148 | 12/1998 |
| WO | WO 0035298 | 6/2000 |
| WO | WO 03042164 | 5/2003 |

OTHER PUBLICATIONS

Vippagunta et al. Advanced Drug Delivery reviews, 2001, 48, 3-26.*
Martinon-Torres, F. Expert Opinion in Pharmacotherapy, 2003, 4(8), 1355-71.*
"MedlinePlus: COPD (Chronic Obstructive Pulmonary Disease)", http://www.nlm.nih.gov/medlineplus/copdchronicobstructivepulmonarydisease.html, accessed Oct. 9, 2007.*
"MedlinePlus: Bronchitis", http://www.nlm.nih.gov/medlineplus/bronchitis.html, accessed Oct. 9, 2007.*
"What is Brochiectasis?", http://www.nhlbi.nih.gov/health/dci/Diseases/brn/brn_whatis.html, accessed Oct. 9, 2007.*
Barnes, P. J. Chest, 111:2, pp. 17S-26S (1997).
Bryan, S.A. et al., Expert Opinion on Investigational Drugs, 9:1, pp. 25-42 (2000).
Haleblian, J. Pharm Sci, 64(8), pp. 1269-1288 (1975).
Finnin and Morgan, J. Pharm Sci, 88(10), pp. 955-958 (1999).
Verma et al., Pharm. Technology On-Line, 25(2), pp. 1-14 (2001).
Schirrmacher et al., Bioorganic & Medicinal Chemisty Letters, 13 (2003), pp. 2687-2692.

* cited by examiner

*Primary Examiner*—James O Wilson
*Assistant Examiner*—Noble Jarrell
(74) *Attorney, Agent, or Firm*—Gregg C. Benson; Robert T. Ronau

(57) ABSTRACT

The invention relates to compounds of formula (1)

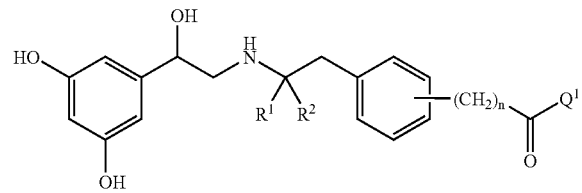

(1)

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

12 Claims, No Drawings

COMPOUNDS FOR THE TREATMENT OF DISEASES

This invention relates to β2 agonists of general formula:

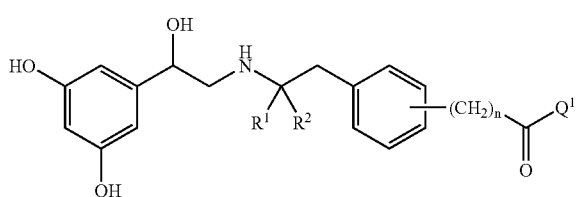

(1)

in which $R^1$, $R^2$, n and $Q^1$ have the meanings indicated below, and to processes for the preparation of, compositions containing and the uses of such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S-26S and Bryan, S. A. et al, Expert Opinion on investigational drugs, 2000, 9:1, pp 25-42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel $β_2$ agonists that would have an appropriate pharmacological profile, for example in terms of potency, selectivity, pharmacokinetics or duration of action. In this context, the present invention relates to novel β2 agonists.

The invention relates to the compounds of general formula (1):

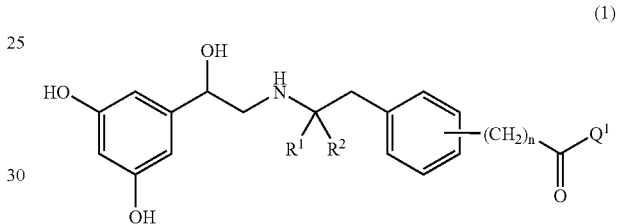

(1)

wherein the $(CH_2)_n$—$C(=O)Q^1$ group is in the meta or para position, $R^1$ and $R^2$ are independently selected from H and $C_1$-$C_4$ alkyl, n is 0, 1 or 2 and $Q^1$ is a group selected from,

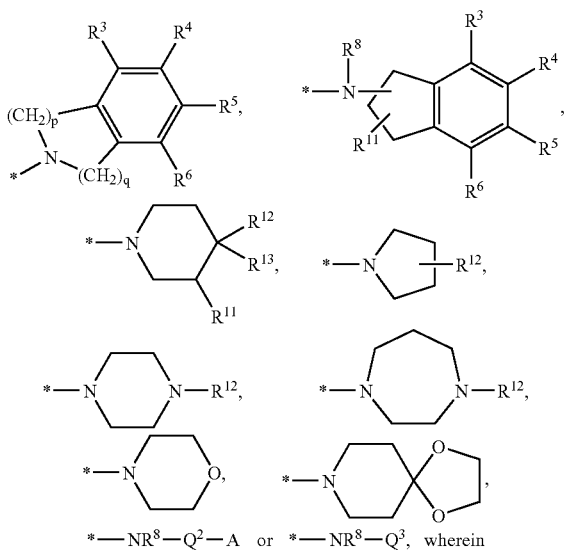

*—$NR^8$—$Q^2$—A or *—$NR^8$—$Q^3$, wherein p is 1 or 2 and q is 1 or 2, $Q^2$ is a single bond or a $C_1$-$C_4$ alkylene optionally substituted with OH, $R^8$ is H or $C_1$-$C_4$ alkyl and, $Q^3$ is $C_1$-$C_6$ alkyl optionally substituted with $NR^9R^{10}$, $OR^9$ or phenoxy, A is selected from:
- $C_3$-$C_{10}$ cycloalkyl, said cycloalkyl being optionally bridged by one or more, preferably 1, 2, 3 or 4, carbon atoms, and being optionally substituted with one hydroxy group,
- a 5 to 6 membered heterocyclic group, optionally aromatic, containing one or two heteroatoms selected from O, N or S, optionally substituted by one or two substituents selected from $C_1$-$C_4$ alkyl, benzyl and cyclopropylmethyl or
- a group

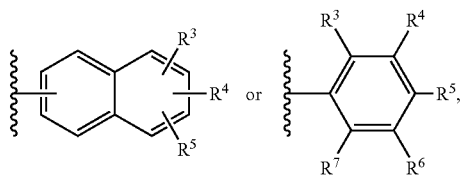

quinolyl or isoquinolyl, $R^3$, $R^4$, $R^5$, $R^6$ and $R^7$ are the same or different and are selected from H, $C_1$-$C_4$ alkyl, $OR^9$, $SR^9$, $SOR^9$, $SO_2R^9$, halo, CN, $CF_3$, $OCF_3$, $SO_2NR^9R^{10}$, $COOR^9$, $CONR^9R^{10}$, $NR^9R^{10}$, $NHCOR^{10}$ and phenyl optionally substituted with OH, $R^9$ and $R^{10}$ are the same or different and are selected from H or $C_1$-$C_4$ alkyl, $R^{11}$ is selected from H or OH, and, $R^{12}$ and $R^{13}$ are the same or different and are selected from H, $C_1$-$C_4$ alkyl optionally susbstituted with $OR^9$, $OR^9$, $C(=O)NH_2$, $C(=O)CH_3$, $N(CH_3)C(=O)CH_3$, $C(=O)OR^9$, phenyl optionally substituted with halogen, pyridyl optionally substituted with CN, oxadiazolyl optionally substituted with $C_1$-$C_4$ alkyl, and, \* represents the attachment point to the carbonyl group;

or, if appropriate, their pharmaceutically acceptable salts and/or isomers, tautomers, solvates or isotopic variations thereof.

The compounds of formula (1) are agonists of the β2 receptors, that are particularly useful for the treatment of β2-mediated diseases and/or conditions, by showing excellent potency, in particular when administered via the inhalation route.

In the here above general formula (1), $C_1$-$C_4$ alkyl and $C_1$-$C_4$ alkylene denote a straight-chain or branched group containing 1, 2, 3 or 4 carbon atoms. $C_1$-$C_6$ alkyl denotes a straight-chain or branched group containing 1, 2, 3, 4, 5 or 6 carbon atoms. This also applies if they carry substituents or occur as substituents of other radicals, for example in O—($C_1$-$C_4$)alkyl radicals, S—($C_1$-$C_4$)alkyl radicals etc. . . . Examples of suitable ($C_1$-$C_4$)alkyl radicals are methyl, ethyl, n-propyl, iso-propyl, n-butyl, isobutyl, sec-butyl, tert-butyl . . . . Examples of suitable O—($C_1$-$C_4$)alkyl radicals are methoxy, ethoxy, n-propyloxy, iso-propyloxy, n-butyloxy, iso-butyloxy, sec-butyloxy and tert-butyloxy. . . .

The $C_3$-$C_{10}$ cycloalkyl wherein 2 carbon atoms or more are optionally bridged by one or more carbon atoms include cyclopropyl, cyclobutyl, cyclopentyl, cyclohexyl, cycloheptyl, adamantyl, bicyclo[3.1.1]heptane, bicyclo[2.2.1]heptane, bicyclo[2.2.2]octane. Preferred cycloalkyl groups are cyclohexyl and adamantyl.

Non limitative examples of "5 to 6 membered heterocyclic group, optionally aromatic, containing one or two heteroatoms selected from O, N or S" are morpholinyl, pyrrolidinyl, piperidyl, piperazinyl, pyrazolyl, thienyl, furanyl, imidazolyl, isothiazolyl, thiazolyl, isoxazolyl, oxazolyl, pyridyl and pyrimidyl.

Preferably, said heterocyclic group contains one nitrogen, two nitrogens or one nitrogen and one oxygen atom.

Preferred aromatic 5 to 6 membered heterocyclic groups are pyrazolyl and pyridyl.

Preferred non aromatic 5 to 6 membered heterocyclic groups are morpholinyl, pyrrolidinyl, piperidyl and piperazinyl.

Finally, halo denotes a halogen atom selected from the group consisting of fluoro, chloro, bromo and iodo in particular fluoro or chloro.

In the following, the free bond on the phenyl group such as in the structure below,

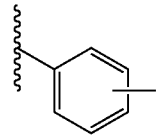

means that the phenyl can be substituted in the meta or para position.

The compounds of the formula (1)

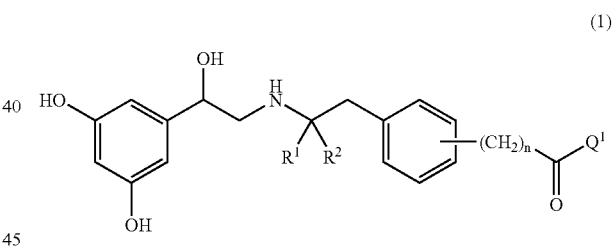

can be prepared using conventional procedures such as by the following illustrative methods in which $Q^1$, $Q^2$, $R^1$, $R^2$, A and n are as previously defined for the compounds of the formula (1) unless otherwise stated.

The amide derivatives of the formula (1) may be prepared by coupling an acid of formula (2):

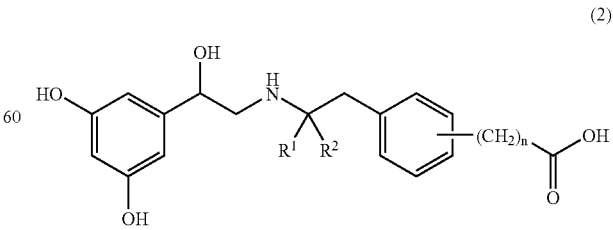

with an amine of formula $NHR^8$-$Q^2$-A, $NHR^8$-$Q^3$

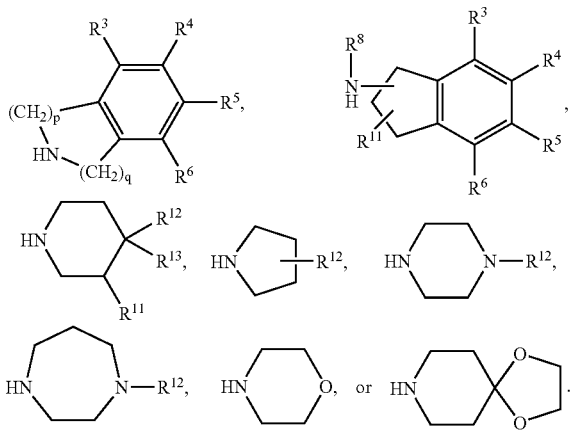

The coupling is generally carried out in an excess of said amine as an acid receptor, with a conventional coupling agent (e.g. 1-(3-dimethylaminopropyl)-3-ethylcarbodiimide hydrochloride or N, N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane N,N-dimethylacetamide, or ethyl acetate, and at temperature comprised between 10° C. and 40° C. (room temperature) for a period of 1-24 hours.

Said amines (are either commercially available or may be prepared by conventional methods well known to the one skilled in the art (e.g. reduction, oxidation, alkylation, transition metal-mediated coupling, protection, deprotection etc. . . ) from commercially available material.

The acid of formula (2) may be prepared from the corresponding ester of formula (4):

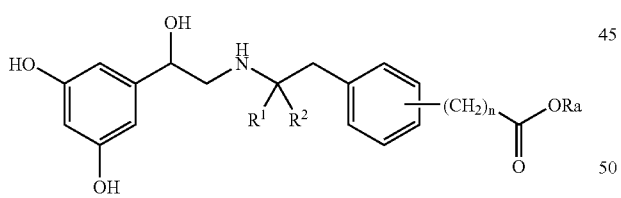

(4)

wherein Ra is a suitable acid protecting group, preferably a ($C_1$-$C_4$)alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

The ester of formula (4) may be prepared by removal of the phenolic protecting group of the compound of formula (5), where PG is defined as a suitable phenol protecting group, typically an alkyl or alkoxy ether (eg. methyl, benzyl, methoxymethyl) and is preferably benzyl:

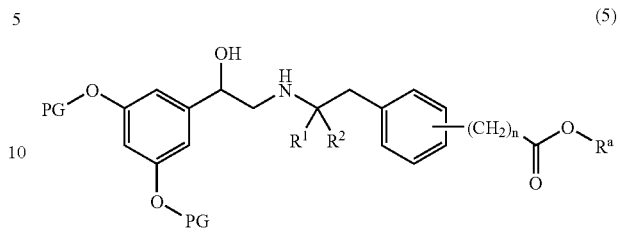

(5)

Reagents suitable to achieve this deprotection are described in the text book T. W. GREENE, Protective Groups in Organic Synthesis, A. Wiley-Interscience Publication, 1981. In a typical procedure, when PG represents benzyl, this may be achieved by hydrogenation using a suitable catalyst (eg. palladium hydroxide or palladium on charcoal) in a suitable solvent such as ethanol or methanol under an atmosphere of hydrogen, optionally at elevated pressure (eg 60 psi) and at a temperature between room temperature and 60° C. for 8-24 hours.

Alternatively transfer hyderogenation can be used with a suitable catalyst (e.g. palladium hydroxide) and ammonium formate as a hydrogen source in a suitable solvent such as ethanol and at a temperature between room temperatrue and 60° C.

The ester of formula (5) may be prepared by reaction of an amine of formula (6):

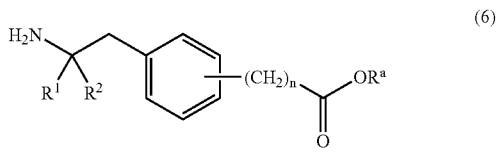

(6)

wherein Ra and n are as previously defined, with a bromide of formula (7):

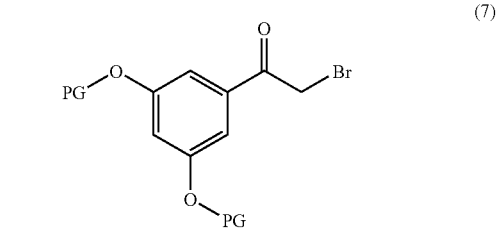

(7)

In a typical procedure, the amine of formula (6) is reacted with a bromide of formula (7) optionally in the presence of a solvent or mixture of solvents (e.g. dimethylsulfoxide, toluene, N, N-dimethylformamide, acetonitrile, THF), optionally in the presence of a suitable base (e.g. triethylamine, diisopropylethylamine, potassium carbonate) at a temperature comprised between 60° C. and 120° C., for 12 to 120 hours. The resulting intermediate amino ketone can then be reduced using a suitable reducing agent such as sodium borohydride or diisobutyl aluminium hydride.

The bromide of formula (7) may be prepared from the ketone of formula (19):

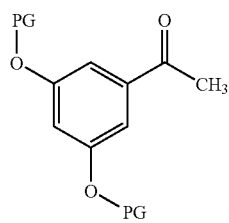

(7)

by bromination with a suitable bromine source. In a typical procedure the ketone is treated with a brominating agent (e.g. Et$_4$NBr$_3$) in a suitable solvent such as THF and methanol at room temperature for about 24 hours.

The ketone of formula (19) is commercially available.

The amine of formula (6), where R$^1$ is Me and R$^2$ is H, may be prepared as either the (R) or (S) enantiomer from the corresponding protected amine of formula (8):

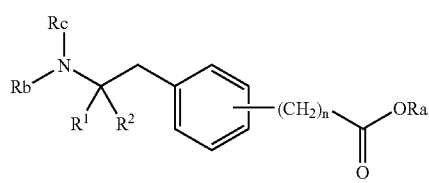

(8)

wherein Ra and n are as previously defined and Rb and Rc represent any suitable substituents so that HNRbRc is a chiral amine (for example, Rb may be hydrogen and Rc may be α-methylbenzyl), provided that the bonds between N and Rb and N and Rc can be easily cleaved to give the free amine of formula (5) using standard methodology for cleaving nitrogen protecting groups, such as those found in the text book T. W. GREENE, Protective Groups in Organic Synthesis, A. Wiley-Interscience Publication, 1981.

The amine of formula (8) may be prepared as a single diastereomer by reaction of an amine of formula HNRbRc with a ketone of formula (9):

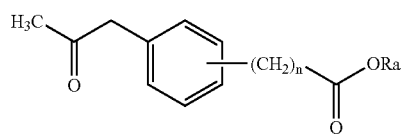

(9)

wherein Ra, Rb, Rc and n are as previously defined.

In a typical procedure, the reaction of the ketone of formula (9) with the amine of formula HNRbRc leads to a chiral intermediate which is in turn reduced by a suitable reducing agent (e.g. sodium cyanoborohydride of formula NaCNBH$_3$ or sodium triacetoxyborohydride of formula Na(OAc)$_3$BH) optionally in the presence of a drying agent (e.g. molecular sieves, magnesium sulfate) and optionally in the presence of an acid catalyst (e.g. acetic acid) to give the amine of formula (8) as a mixture of diastereomers. The reaction is generally done in a solvent such as tetrahydrofuran or dichloromethane at a temperature comprised between 20° C. and 80° C. for 3 to 72 hours. The resulting product is then converted to the hydrochloride salt and selectively crystallised from a suitable solvent or mixture of solvents (e.g. isopropanol, ethanol, methanol, diisopropyl ether or diisopropyl ether/methanol) to give (8) as a single diastereomer.

The ketone of formula (9) where n=1 may be prepared by palladium mediated coupling of an aryl halide of formula (10):

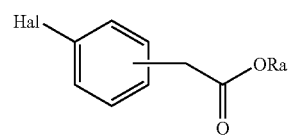

(10)

wherein Ra is as previously defined and Hal represents an halogen atom, which includes, but is not limited to bromo and iodo, with an enolate or enolate equivalent.

In a typical procedure, the aryl halide of formula (10) is reacted with a tin enolate generated in-situ by treatment of isopropenyl acetate with tri-n-butyltin methoxide of formula Bu$_3$SnOMe in the presence of a suitable palladium catalyst (palladium acetate/ tri-ortho-tolylphosphine of formula Pd(OAc)$_2$/P(o-Tol)$_3$) in a non-polar solvent (e.g. toluene, benzene, hexane). Preferably, the reaction is carried out at a temperature comprised between 80° C. and 110° C. for 6 to 16 hours.

The aryl halide of formula (10) may be obtained by esterification of the corresponding acid of formula (11):

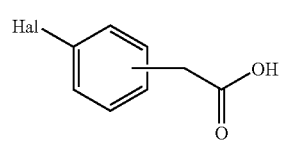

(11)

wherein Hal is as previously defined, according to any method well-known to the one skilled in the art to prepare an ester from an acid, without modifying the rest of the molecule.

In a typical procedure, the acid of formula (11) is reacted with an alcoholic solvent of formula RaOH, wherein Ra is as previously defined, in the presence of an acid such as hydrogen chloride at a temperature between 10° C. and 40° C. (room temperature) for 8 to 16 hours.

The acid of formula (11) is a commercial product.

The amine of formula (6), where R$^1$ and R$^2$ are both C$_1$-C$_4$ alkyl, may be prepared according to the following scheme:

Scheme 1

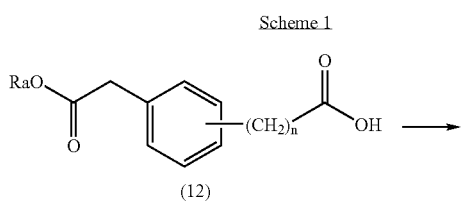

(12)

-continued

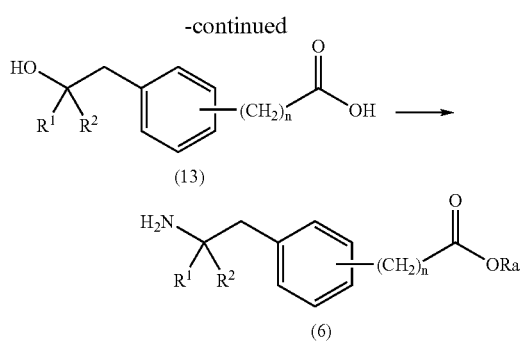

wherein $R^1$, $R^2$ and Ra are as previously defined.

In a typical procedure, the ester of formula (12) is reacted with an "activated" alkyl (organometallic alkyl such as $R^2$MgBr, $R^2$MgCl or $R^2$Li) to give the corresponding tertiary alcohol of formula (13) using the method described above.

Said tertiary alcohol of formula (13) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting amino acid is then esterified using the method described herein to give the amine of formula (6).

Alternatively, the amine of formula (6), where $R^1$ are $R^2$ both $C_1$-$C_4$ alkyl and n=0, may be prepared according to the following scheme:

Scheme 2

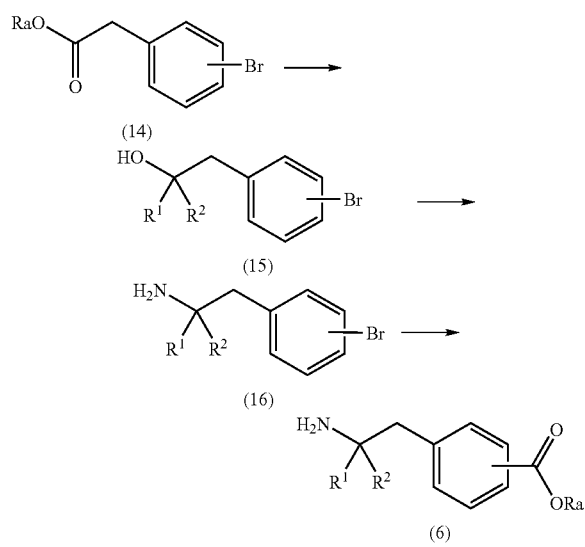

wherein $R^1$, $R^2$ and Ra are as previously defined.

In a typical procedure, the ester of formula (14) is reacted with an "activated" alkyl (organometallic alkyl such as $R^2$MgBr, $R^2$MgCl or $R^2$Li) to give the corresponding tertiary alcohol of formula (15) using the method described above.

Said tertiary alcohol of formula (15) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks to give the bromo amine (16).

The resulting bromo amine (16) is treated with a suitable palladium catalyst (e.g. [1,1'-bis(diphenylphosphino)ferrocene]dichloropalladium(II)) under an atmosphere of carbon monoxide using RaOH as solvent (e.g. MeOH, EtOH) at elevated temperature (100° C.) and pressure (100 psi) to give the ester of formula (6).

The ketone of formula (9) where n=2 may be prepared by reduction of an alkene of formula (17):

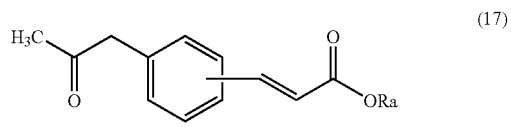

In a typical procedure, a solution of the olefin of formula (17) in a suitable solvent (e.g. methanol, ethanol, ethyl acetate) is treated with a palladium catalyst (e.g. 10% palladium on charcoal) and stirred under an atmosphere of hydrogen, optionally at elevated pressure (e.g. 60 psi), at temperature between room temperature and 60° C. for 8-24 hours.

The alkene of formula (17) may be prepared by a palladium mediated coupling of an activated olefin with an aryl halide of formula (18):

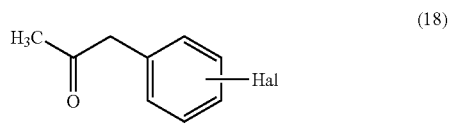

In a typical procedure, the aryl halide (18) is coupled with a vinyl ester (e.g. methyl acrylate) in the presence of a suitable palladium catalyst (e.g. tetrakis(triphenylphosphine)palladium(0) of formula Pd(PPh$_3$)$_4$, palladium acetate/tri-ortho-tolylphosphine of formula Pd(OAc)$_2$/P(o-tol)$_3$ or (diphenylphosphino)ferrocenyl palladium chloride of formula dppfPdCl$_2$) in a suitable solvent (e.g. acetonitrile, N, N-dimethylformamide, toluene), optionally in the presence of a base such as triethylamine at a temperature between 40° C. and 101° C. for 8 to 24 hours.

The ketone of formula (18) is a commercial product.

Alternatively a compound of formula (1) may be prepared by reaction of a bromide of formula (7) and an amine of formula (20):

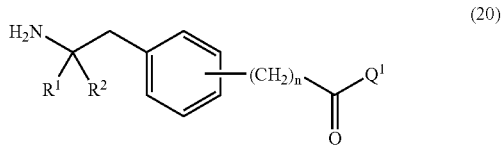

where $R^1$, $R^2$, $Q^1$ and n are as previously defined for the compounds of the formula (1) unless otherwise stated.

In a typical procedure, the amine of formula (20) is reacted with a bromide of formula (7) optionally in the presence of a solvent or mixture of solvents (e.g. dimethylsulfoxide, toluene, N, N-dimethylformamide, acetonitrile), optionally in the presence of a suitable base (e.g. triethylamine, diisopropylethylamine, potassium carbonate) at a temperature comprised between 60° C. and 120° C., for 12 to 48 hours. The resulting intermediate amino ketone can then be reduced using a suitable reducing agent such as sodium borohydride or diisobutyl aluminium hydride.

The amide of formula (20) may be prepared by coupling an acid of formula (21) incorporating a suitable amine protecting group P1:

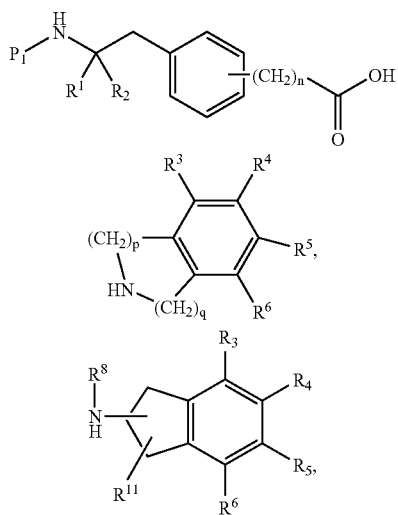

with an amine of formula

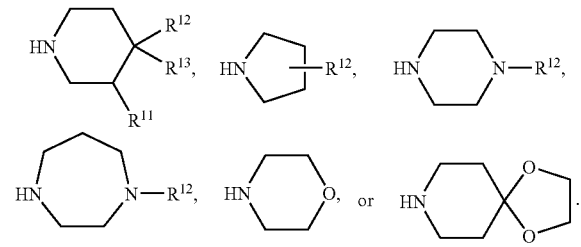

The coupling is generally carried out in an excess of said amine as an acid receptor, with a conventional coupling agent (e.g. 1-(3-dimethylaminopropyl)-3-ethylcarbodiimide hydrochloride or N, N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane or ethyl acetate, and at temperature comprised between 10° C. and 40° C. (room temperature) for a period of 1-24 hours. Said amine is either commercially available or may be prepared by conventional methods well known to the one skilled in the art (e.g. reduction, oxidation, alkylation, transition metal-mediated coupling, protection, deprotection etc. . . ) from commercially available material.

The acid of formula (21) may be prepared from the corresponding ester of formula (6). The acid of formula (21), where $R^1$ and $R^2$ are both $C_1$-$C_4$ alkyl, may be prepared from the ester (6) incorporating a suitable amine protecting group P1 either before or after the acid formation:

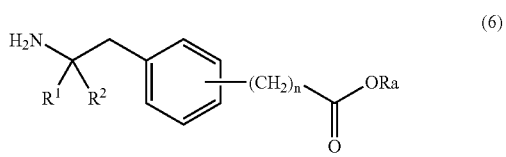

wherein Ra is a suitable acid protecting group, preferably a ($C_1$-$C_4$)alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

The amine of formula (6), where $R^1$ and $R^2$ are both H, may be prepared according to the following scheme:

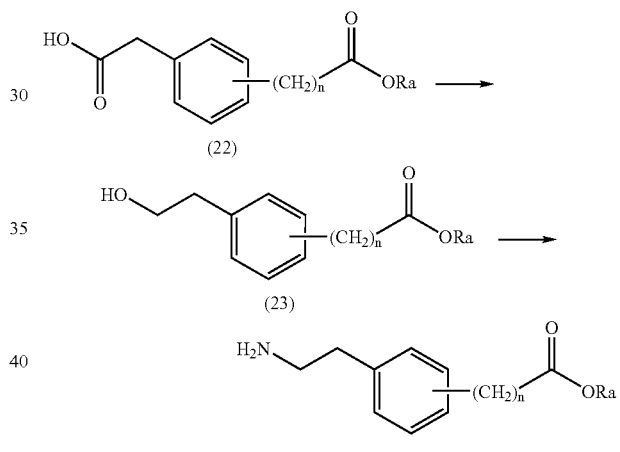

wherein $R^1$, $R^2$ and Ra are as previously defined.

In a typical procedure, the acid of formula (22) is preferentially reduced to the corresponding alcohol (23) in the presence of the ester. This may be performed by formation of the acyl imidazole or mixed anhydride and subsequent reduction with sodium borohydride or another suitable reducing agent.

Said primary alcohol of formula (23) is then converted into a leaving group such as mesylate, tosylate, bromide or iodide and displaced with appropriate amine nucleophile. The preferred nucleophile is azide ion which can then be reduced to the primary amine via hydrogenation or triphenylphosphine. Alternative nucleophiles could include ammonia or alkylamines such as benzylamine or allylamine and subsequent cleavage of the alkyl group to furnish the amine.

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective*

*Groups in Organic Synthesis*, A. Wiley-Interscience Publication, 1981) or by P. J. Kocienski (*Protecting groups*, Georg Thieme Verlag, 1994), can be used.

For example, in the above processes, the bromine of formula (7) may be replaced by a protected bromine of formula

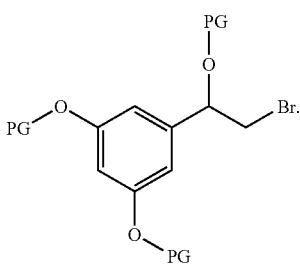

The bromide may be prepared in a racemic fashion using a reducing agent such as sodium borohydride in a suitable solvent such as ethanol. Alternatively the alcohol may be prepared as either the (R) or (S) enantiomer according to methods well described in the literature (Tetrahedron Letters 1994, 35(50), 9375).'

The compound of formula (I) would then be obtained by deprotection of a compound of formula

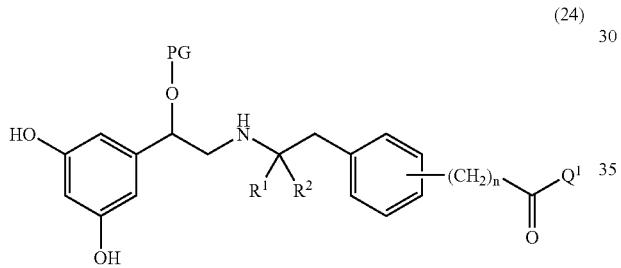

(24)

wherein PG represents a suitable alcohol protecting group, typically a silyl group such as TBDMS or TMS, and preferably TBDMS.

The deprotection may be carried out according to the methods described in standard text-books such as "Protective Groups in Organic Synthesis" by T. W. Greene, A. Wiley-Interscience Publication, 1981. In a typical procedure, where PG represents TBDMS, compound of formula (24) is treated with 10-18 eq ammonium fluoride in aqueous methanol, at about 45° C. for between 18 and 42 hours. An alternative agent for deprotection would be one equivalent of triethylamine trihydrofluoride in tetrahydrofuran or suitable solvent at room temperature for 12 hours.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

In a preferred embodiment of the invention, $Q^2$ is a single bond.

In a preferred embodiment of the invention, A is selected from morpholinyl, pyrrolidinyl, piperidyl, piperazinyl or pyrazolyl, optionally susbstituted by a methyl group.

In a preferred embodiment of the invention, A is selected from pyrazolyl optionally substituted by one or two $C_1$-$C_4$ alkyl group.

In a preferred embodiment of the invention, $Q^1$ is *—$NR^8$-$Q^3$.

In a preferred embodiment of the invention, $Q^1$ is a group selected from,

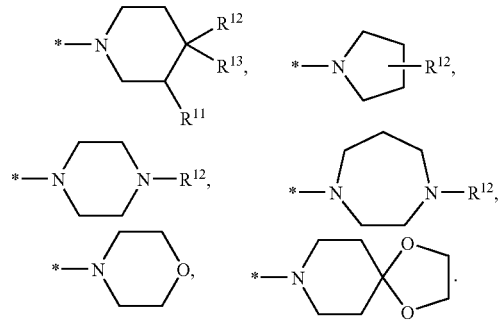

In a preferred embodiment, $Q^1$ is a group

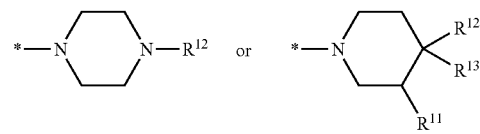

wherein $R^{11}$ and $R^{13}$ are H and $R^{12}$ is pyridyl or oxadiazolyl optionally substituted with a $C_1$-$C_4$ alkyl.

The following group of compounds of formula (1) is more preferred:

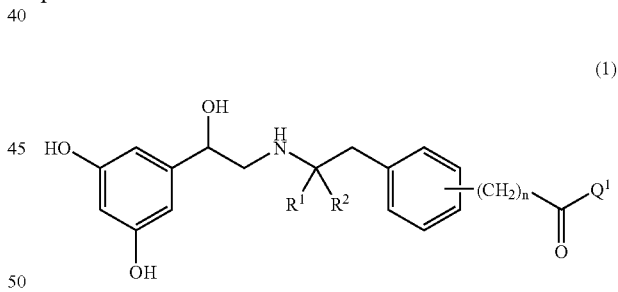

(1)

wherein the $(CH_2)_n$—$C(=O)Q^1$ group is in the meta or para position, $R^1$ and $R^2$ are independently selected from H and $C_1$-$C_4$ alkyl, n is 0, 1 or 2 and $Q^1$ is a group selected from,

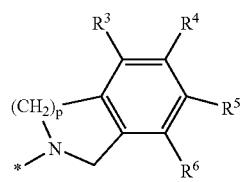

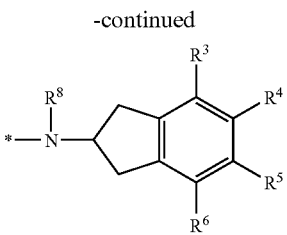

and a group *—NR$^8$-Q$^2$-A, wherein p is 1 or 2, Q$^2$ is a C$_1$-C$_4$ alkylene, R$^8$ is H or C$_1$-C$_4$ alkyl and A is pyridyl, C$_3$-C$_{10}$ cycloalkyl, said cycloalkyl being optionally bridged by 1, 2, 3 or 4 carbon atoms, preferably 1 or 2 carbon atoms, tetrahydropyranyl, piperidinyl, tetrahydrothiopyranyl or a group

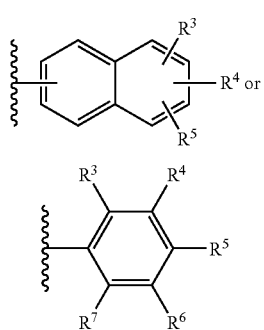

R$^3$, R$^4$, R$^5$, R$^6$ and R$^7$ are the same or different and are selected from H, C$_1$-C$_4$ alkyl, OR$^9$, SR$^9$, SOR$^9$, SO$_2$R$^9$, halo, CN, CF$_3$, OCF$_3$, SO$_2$NR$^9$R$^{10}$, COOR$^9$, CONR$^9$R$^{10}$, NR$^9$R$^{10}$, NHCOR$^{10}$ and phenyl optionally substituted with OH;

R$^9$ and R$^{10}$ are the same or different and are selected from H or C$_1$-C$_4$ alkyl and,

* represents the attachment point to the carbonyl group;

or, if appropriate, their pharmaceutically acceptable salts and/or isomers, tautomers, solvates or isotopic variations thereof.

The compounds of formula (1) containing the following substituents are preferred:

Preferably Q$^1$ is a group *—NH-Q$^2$-A, wherein A is cyclopropyl, cyclohexyl, cycloheptyl or adamantyl.

More preferably Q$^1$ is a group *—NH-Q$^2$-A, wherein A is cyclohexyl or adamantyl.

Preferably, A is naphthyl optionally substituted with OR$^9$.

Preferably R$^8$ is H or CH$_3$. More preferably, R$^8$ is H

Preferably, Q$^1$ is

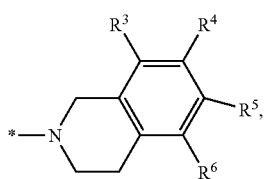

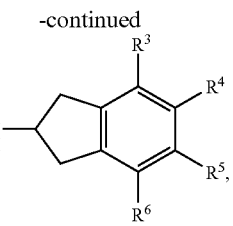

wherein R$_3$, R$_4$, R$_5$ and are H.

Preferably, Q$^1$ is a group *—NH-Q$^2$-A, wherein A is a group

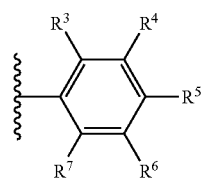

wherein R$^3$, R$^4$, R$^5$, R$^6$ and R$^7$ are the same or different and are selected from H, C$_1$-C$_4$ alkyl, OR$^9$, SR$^9$, halo, CN, CF$_3$, OCF$_3$, SO$_2$NR$^9$R$^{10}$, COOR$^9$, CONR$^9$R$^{10}$, NR$^9$R$^{10}$, NHCOR$^{10}$ and phenyl optionally substituted with OH, provided at least 2 of R$^3$ to R$^7$ are equal to H;

wherein R$^9$ and R$^{10}$ are the same or different and are selected from H or C$_1$-C$_4$ alkyl.

More preferably, Q$^1$ is a group *—NH-Q$^2$-A, wherein A is a group

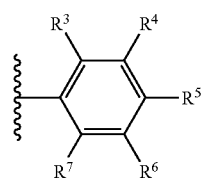

wherein R$^3$, R$^4$, R$^5$, R$^6$ and R$^7$ are the same or different and are selected from H, CH$_3$, OCH$_3$, OCH$_2$—CH$_3$, SCH$_3$, halo, CF$_3$, provided at least 2 of R$^3$ to R$^7$ are equal to H.

In the above groups of compounds, the following substituents are particularly preferred:

Q$^2$ is —CH$_2$—, —(CH$_2$)$_2$—, —(CH$_2$)$_3$—, —CH(CH$_3$)—, —CH$_2$CH(CH$_3$)— or (CH(CH$_3$)$_2$)—, preferably —CH$_2$—.

R$^1$ is H or C$_1$-C$_4$ alkyl and R$^2$ is C$_1$-C$_4$ alkyl. More preferably, R$^1$ is H or CH$_3$ and R$^2$ is CH$_3$.

n is 1.

R$^1$ is H and R$^2$ is CH$_3$ and n is 1.

R$^1$ is CH$_3$, R$^2$ is CH$_3$ and n is 1.

The following compounds, which can be prepared according to the processes disclosed herein, are preferred:

N-benzyl-2-[3-(2-{[2-(3,5-dihydroxyphenyl)-2-hydroxyethyl]amino}-2-methylpropyl)phenyl]acetamide;

N-cyclopropyl-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[(1R,2S)-2-(hydroxymethyl)cyclohexyl]acetamide;

2-[3-(2-{[2-(3,5-dihydroxyphenyl)-2-hydroxyethyl]amino}-2-methylpropyl)phenyl]-N-(3-morpholin-4-ylpropyl)acetamide;

2-[3-(2-{[2-(3,5-dihydroxyphenyl)-2-hydroxyethyl]amino}-2-methylpropyl)phenyl]-N-(pyridin-2-ylmethyl)acetamide;

2-[3-(2-{[2-(3,5-dihydroxyphenyl)-2-hydroxyethyl]amino}-2-methylpropyl)phenyl]-N-(2-morpholin-4-ylethyl)acetamide;

2-[3-(2-{[2-(3,5-dihydroxyphenyl)-2-hydroxyethyl]amino}-2-methylpropyl)phenyl]-N-isopropylacetamide;

N-(4-chlorobenzyl)-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[2-(dimethylamino)ethyl]acetamide;

N-[2-(diethylamino)ethyl]-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[3-(dimethylamino)propyl]acetamide;

2-[3-(2-{[2-(3,5-dihydroxyphenyl)-2-hydroxyethyl]amino}-2-methylpropyl)phenyl]-N-pentylacetamide;

2-[3-(2-{[2-(3,5-dihydroxyphenyl)-2-hydroxyethyl]amino}-2-methylpropyl)phenyl]-N-(2-pyrrolidin-1-ylethyl)acetamide;

N-(2,4-dichlorobenzyl)-2-[3-(2-{[2-(3,5-dihydroxyphenyl)-2-hydroxyethyl]amino}-2-methylpropyl)phenyl]acetamide;

N-(3,4-dichlorobenzyl)-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-(4-methoxybenzyl)acetamide;

2-[3-(2-{[2-(3,5-dihydroxyphenyl)-2-hydroxyethyl]amino}-2-methylpropyl)phenyl]-N-(2-hydroxyethyl)acetamide;

2-[3-(2-{[2-(3,5-dihydroxyphenyl)-2-hydroxyethyl]amino}-2-methylpropyl)phenyl]-N-propylacetamide;

2-[3-(2-{[2-(3,5-dihydroxyphenyl)-2-hydroxyethyl]amino}-2-methylpropyl)phenyl]-N-(3-methoxypropyl)acetamide;

N-cyclobutyl-2-[3-(2-{([2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[(1R)-1-(1-naphthyl)ethyl]acetamide;

N-2,3-dihydro-1H-inden-1-yl-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[2-(1-methylpyrrolidin-2-yl)ethyl]acetamide 2-[3-(2-{[2-(3,5-dihydroxyphenyl)-2-hydroxyethyl]amino}-2-methylpropyl)phenyl]-N-(4-fluorobenzyl)acetamide;

2-[3-(2-{[2-(3,5-dihydroxyphenyl)-2-hydroxyethyl]amino}-2-methylpropyl)phenyl]-N-(4-phenylbutyl)acetamide;

2-[3-(2-{[2-(3,5-dihydroxyphenyl)-2-hydroxyethyl]amino}-2-methylpropyl)phenyl]-N-(3-methoxybenzyl)acetamide;

2-[3-(2-{[2-(3,5-dihydroxyphenyl)-2-hydroxyethyl]amino}-2-methylpropyl)phenyl]-N-(3-ethoxypropyl)acetamide;

2-[3-(2-{[2-(3,5-dihydroxyphenyl)-2-hydroxyethyl]amino}-2-methylpropyl)phenyl]-N-(3,4,5-trimethoxybenzyl)acetamide;

2-[3-(2-{[2-(3,5-dihydroxyphenyl)-2-hydroxyethyl]amino}-2-methylpropyl)phenyl]-N-[4-(trifluoromethyl)benzyl]acetamide;

2-[3-(2-{[2-(3,5-dihydroxyphenyl)-2-hydroxyethyl]amino}-2-methylpropyl)phenyl]-N-[2-(trifluoromethyl)benzyl]acetamide;

2-[3-(2-{[2-(3,5-dihydroxyphenyl)-2-hydroxyethyl]amino}-2-methylpropyl)phenyl]-N-(3,5-dimethoxybenzyl)acetamide;

2-[3-(2-{[2-(3,5-dihydroxyphenyl)-2-hydroxyethyl]amino}-2-methylpropyl)phenyl]-N-(2-phenoxyethyl)acetamide;

2-[3-(2-{[2-(3,5-dihydroxyphenyl)-2-hydroxyethyl]amino}-2-methylpropyl)phenyl]-N-[(1S)-2-hydroxy-1-methylethyl]acetamide;

2-[3-(2-{[2-(3,5-dihydroxyphenyl)-2-hydroxyethyl]amino}-2-methylpropyl)phenyl]-N-[(1S)-1-(hydroxymethyl)-2-methylpropyl]acetamide;

2-[3-(2-{[2-(3,5-dihydroxyphenyl)-2-hydroxyethyl]amino}-2-methylpropyl)phenyl]-N-[(1S,2S)-1-(hydroxymethyl)-2-methylbutyl]acetamide;

N-[(1R)-1-benzyl-2-hydroxyethyl]-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[(1R)-1-(hydroxymethyl)propyl]acetamide;

2-[3-(2-{[2-(3,5-dihydroxyphenyl)-2-hydroxyethyl]amino}-2-methylpropyl)phenyl]-N-[(1S)-1-(hydroxymethyl)-2,2-dimethylpropyl]acetamide;

N-[(1S)-2-cyclohexyl-1-(hydroxymethyl)ethyl]-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-[(1S,2R)-2-hydroxy-2,3-dihydro-1H-inden-1-yl]acetamide;

2-[3-(2-{[2-(3,5-dihydroxyphenyl)-2-hydroxyethyl]amino}-2-methylpropyl)phenyl]-N-(2-propoxyethyl)acetamide;

2-[3-(2-{[2-(3,5-dihydroxyphenyl)-2-hydroxyethyl]amino}-2-methylpropyl)phenyl]-N-(4-hydroxycyclohexyl)acetamide;

2-[3-(2-{[2-(3,5-dihydroxyphenyl)-2-hydroxyethyl]amino}-2-methylpropyl)phenyl]-N-(3-propoxypropyl)acetamide;

2-[3-(2-{[2-(3,5-dihydroxyphenyl)-2-hydroxyethyl]amino}-2-methylpropyl)phenyl]-N-ethyl-N-(2-hydroxyethyl)acetamide;

1-{[3-(2-{[2-(3,5-dihydroxyphenyl)-2-hydroxyethyl]amino}-2-methylpropyl)phenyl]acetyl}piperidine-4-carboxamide;

5-{2-[(2-{3-[2-(4-acetylpiperazin-1-yl)-2-oxoethyl]phenyl}-1,1-dimethylethyl)amino]-1-hydroxyethyl}benzene-1,3-diol;

5-{2-[(2-{3-[2-(3,4-dihydroisoquinolin-2(1H)-yl)-2-oxoethyl]phenyl}-1,1-dimethylethyl)amino]-1-hydroxyethyl}benzene-1,3-diol;

N-benzyl-2-[3-(2-{[2-(3,5-dihydroxyphenyl)-2-hydroxyethyl]amino}-2-methylpropyl)phenyl]-N-methylacetamide;

5-(1-hydroxy-2-{[2-(3-{2-[4-(2-hydroxyethyl)piperazin-1-yl]-2-oxoethyl}phenyl)-1,1-dimethylethyl]amino}ethyl)benzene-1,3-diol;

5-(2-{[2-(3-{2-[4-(4-chlorophenyl)-4-hydroxypiperidin-1-yl]-2-oxoethyl}phenyl)-1,1-dimethylethyl]amino}-1-hydroxyethyl)benzene-1,3-diol;

5-{2-[(1,1-dimethyl-2-{3-[2-(4-methylpiperazin-1-yl)-2-oxoethyl]phenyl}ethyl)amino]-1-hydroxyethyl}benzene-1,3-diol;

2-[3-(2-{[2-(3,5-dihydroxyphenyl)-2-hydroxyethyl]amino}-2-methylpropyl)phenyl]-N-methyl-N-(2-phenylethyl)acetamide;

5-{2-[(1,1-dimethyl-2-{3-[2-oxo-2-(4-pyridin-2-ylpiperazin-1-yl)ethyl]phenyl}ethyl)amino]-1-hydroxyethyl}benzene-1,3-diol;

2-[3-(2-{[2-(3,5-dihydroxyphenyl)-2-hydroxyethyl]amino}-2-methylpropyl)phenyl]-N-[3-(dimethylamino)propyl]-N-methylacetamide;

2-[3-(2-{[2-(3,5-dihydroxyphenyl)-2-hydroxyethyl]amino}-2-methylpropyl)phenyl]-N-(2-hydroxyethyl)-N-propylacetamide;

N-[2-(diethylamino)ethyl]-2-[3-(2-{[2-(3,5-dihydroxyphenyl)-2-hydroxyethyl]amino}-2-methylpropyl)phenyl]-N-methylacetamide;

5-{2-[(1,1-dimethyl-2-{3-[2-(4-methyl-1,4-diazepan-1-yl)-2-oxoethyl]phenyl}ethyl)amino]-1-hydroxyethyl}benzene-1,3-diol;

5-[2-({1-dimethyl-2-[3-(2-morpholin-4-yl-2-oxoethyl)phenyl]ethyl}amino)-1-hydroxyethyl]benzene-1,3-diol;

2-[3-(2-{[2-(3,5-dihydroxyphenyl)-2-hydroxyethyl]amino}-2-methylpropyl)phenyl]-N-methyl-N-[(1S)-1-phenylethyl]acetamide;

5-[2-({1,1-dimethyl-2-[3-(2-oxo-2-piperidin-1-ylethyl)phenyl]ethyl}amino)-1-hydroxyethyl]benzene-1,3-diol;

5-(1-hydroxy-2-{[2-(3-{2-[(3R)-3-hydroxypyrrolidin-1-yl]-2-oxoethyl}phenyl)-1,1-dimethylethyl]amino}ethyl)benzene-1,3-diol;

5-(1-hydroxy-2-{[2-(3-{2-[(3R)-3-hydroxypiperidin-1-yl]-2-oxoethyl}phenyl)-1,1-dimethylethyl]amino}ethyl)benzene-1,3-diol;

5-{2-[(2-{3-[2-(4-acetyl-1,4-diazepan-1-yl)-2-oxoethyl]phenyl}-1,1-dimethylethyl)amino]-1-hydroxyethyl}benzene-1,3-diol;

5-(1-hydroxy-2-{[2-(3-{2-[4-(hydroxymethy)piperidin-1-yl]-2-oxoethyl}phenyl)-1,1-dimethylethyl]amino}ethyl)benzene-1,3-diol;

N-(1-{[3-(2-{[2-(3,5-dihydroxyphenyl)-2-hydroxyethyl]amino}-2-methylpropyl)phenyl]acetyl}pyrrolidin-3-yl)-N-methylacetamide;

2-[3-(2-([2-(3,5-dihydroxyphenyl)-2-hydroxyethyl]amino)-2-methylpropyl)phenyl]-N-(2-methoxyethyl)-N-propylacetamide;

2-[3-(2-{[2-(3,5-dihydroxyphenyl)-2-hydroxyethyl]amino}-2-methylpropyl)phenyl]-N-ethyl-N-(2-methoxyethyl)acetamide;

2-[3-(2-{[2-(3,5-dihydroxyphenyl)-2-hydroxyethyl]amino}-2-methylpropyl)phenyl]-N-[3-(dimethylamino)-2,2-dimethylpropyl]acetamide;

2-[3-(2-{[2-(3,5-dihydroxyphenyl)-2-hydroxyethyl]amino}-2-methylpropyl)phenyl]-N-[3-fluoro-5-(trifluoromethyl)benzyl]acetamide;

2-[3-(2-{[2-(3,5-dihydroxyphenyl)-2-hydroxyethyl]amino}-2-methylpropyl)phenyl]-N-[(1S)-1-(hydroxymethyl)-3-methylbutyl]acetamide;

2-[3-(2-{[2-(3,5-dihydroxyphenyl)-2-hydroxyethyl]amino}-2-methylpropyl)phenyl]-N-[(1S)-2-hydroxy-1-phenylethyl]acetamide;

2-[3-(2-{[2-(3,5-dihydroxyphenyl)-2-hydroxyethyl]amino}-2-methylpropyl)phenyl]-N,N-diethylacetamide;

2-[3-(2-{[2-(3,5-dihydroxyphenyl)-2-hydroxyethyl]amino}-2-methylpropyl)phenyl]-N-1H-pyrazol-5-ylacetamide;

2-[3-(2-{[2-(3,5-dihydroxyphenyl)-2-hydroxyethyl]amino}-2-methylpropyl)phenyl]-N-(5-methyl-1H-pyrazol-3-yl)acetamide;

N-(cyclohexylmethyl)-2-[3-(2-{[2-(3,5-dihydroxyphenyl)-2-hydroxyethyl]amino}-2-methylpropyl)phenyl]acetamide;

ethyl 4-{[3-(2-{[2-(3,5-dihydroxyphenyl)-2-hydroxyethyl]amino}-2-methylpropyl)phenyl]acetyl}piperazine-1-carboxylate;

N-(5-chloropyridin-2-yl)-2-[3-(2-{[2-(3,5-dihydroxyphenyl)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-(6-methylpyridin-2-yl)acetamide;

2-[3-(2-{[2-(3,5-dihydroxyphenyl)-2-hydroxyethyl]amino}-2-methylpropyl)phenyl]-N-(3-methylpyridin-2-yl)acetamide;

2-[3-(2-{[2-(3,5-dihydroxyphenyl)-2-hydroxyethyl]amino}-2-methylpropyl)phenyl]-N-isoquinolin-1-ylacetamide;

2-[3-(2-{[2-(3,5-dihydroxyphenyl)-2-hydroxyethyl]amino}-2-methylpropyl)phenyl]-N-(4,6-dimethylpyridin-2-yl)acetamide;

2-[3-(2-{[2-(3,5-dihydroxyphenyl)-2-hydroxyethyl]amino}-2-methylpropyl)phenyl]-N-(2-methoxybenzyl)acetamide;

N-[(1S)-1-benzyl-2-hydroxyethyl]-2-[3-(2-{[2-(3,5-dihydroxypheny)-2-hydroxyethyl]amino}-2-methylpropyl)phenyl]acetamide;

2-[3-(2-{[2-(3,5-dihydroxyphenyl)-2-hydroxyethyl]amino}-2-methylpropyl)phenyl]-N-(1-ethyl-1H-pyrazol-5-yl)acetamide;

2-[3-(2-{[2-(3,5-dihydroxyphenyl)-2-hydroxyethyl]amino}-2-methylpropyl)phenyl]-N-(1,3-dimethyl-1H-pyrazol-5-yl)acetamide;

2-[3-(2-{[2-(3,5-dihydroxyphenyl)-2-hydroxyethyl]amino}-2-methylpropyl)phenyl]-N-(3-fluorobenzyl)acetamide;

1-{[3-(2-{[2-(3,5-dihydroxyphenyl)-2-hydroxyethyl]amino}-2-methylpropyl)phenyl]acetyl}-L-prolinamide;

5-{2-[(2-{3-[2-(5-amino-3-tert-butyl-1H-pyrazol-1-yl)-2-oxoethyl]phenyl}-1,1-dimethylethyl)amino]-1-hydroxyethyl}benzene-1,3-diol;

2-[3-(2-{[2-(3,5-dihydroxyphenyl)-2-hydroxyethyl]amino}-2-methylpropyl)phenyl]-N-[(1S)-1-phenylethyl]acetamide;

5-{2-[(2-{3-[2-(1,4-dioxa-8-azaspiro[4.5]dec-8-yl)-2-oxoethyl]phenyl}-1,1-dimethylethyl)amino]-1-hydroxyethyl}benzene-1,3-diol;

N-[2-(4-Chloro-phenyl)-ethyl]-3-{2-[2-(3,5-dihydroxy-phenyl)-2-hydroxy-ethylamino]-2-methyl-propyl}-benzamide;

N-Adamantan-1-yl-2-(3-{2-[2-(3,5-dihydroxy-phenyl)-2-hydroxy-ethylamino]-propyl}-phenyl)-acetamide;

3-{2-[2-(3,5-Dihydroxy-phenyl)-2-hydroxy-ethylamino]-2-methyl-propyl}-N-[2-(3-fluoro-phenyl)-ethyl]-benzamide;

N-[2-(2-Chloro-phenyl)-ethyl]-3-{2-[2-(3,5-dihydroxy-phenyl)-2-hydroxy-ethylamino]-2-methyl-propyl}-benzamide;

3-{2-[2-(3,5-Dihydroxy-phenyl)-2-hydroxy-ethylamino]-2-methyl-propyl}-N-[2-(2,3-dimethyl-phenyl)-ethyl]-benzamide;

N-[2-(2-Chloro-4-fluoro-phenyl)-ethyl]-3-{2-[2-(3,5-dihydroxy-phenyl)-2-hydroxy-ethylamino]-2-methyl-propyl}-benzamide;
3-{2-[2-(3,5-Dihydroxy-phenyl)-2-hydroxy-ethylamino]-2-methyl-propyl}-N-[2-(4-methoxy-2,3-dimethyl-phenyl)-ethyl]-benzamide;
N-(3,4-Dichloro-benzyl)-2-(3-{2-[2-(3,5-dihydroxy-phenyl)-2-hydroxy-ethylamino]-2-methyl-propyl}-phenyl)-acetamide;
N-(3,4-Dichloro-benzyl)-3-{2-[2-(3,5-dihydroxy-phenyl)-2-hydroxy-ethylamino]-2-methyl-propyl}-benzamide;
N-(4-Chloro-benzyl)-3-{2-[2-(3,5-dihydroxy-phenyl)-2-hydroxy-ethylamino]-2-methyl-propyl}-benzamide;
N-Adamantan-1-yl-3-{2-[2-(3,5-dihydroxy-phenyl)-2-hydroxy-ethylamino]-2-methyl-propyl}-benzamide;
N-(4-Chloro-benzyl)-2-(3-{2-[2-(3,5-dihydroxy-phenyl)-2-hydroxy-ethylamino]-2-methyl-propyl}-phenyl)-acetamide;
N-(4-Trifluoromethoxybenzyl)-2-(3-{2-[2-(3,5-dihydroxy-phenyl)-2-hydroxy-ethylamino]-2-methyl-propyl}-phenyl)-acetamide;
2-(3-{2-[2-(3,5-Dihydroxy-phenyl)-2-hydroxy-ethylamino]-2-methyl-propyl}-phenyl)-N-pyridin-2-ylmethyl-acetamide;
N-(3,4-Dichloro-benzyl)-2-(3-{2-[2-(3,5-dihydroxy-phenyl)-2-hydroxy-ethylamino]-propyl}-phenyl)-acetamide;
N-(Benzyl)-2-(3-{2-[2-(3,5-dihydroxy-phenyl)-2-hydroxy-ethylamino]-propyl}-phenyl)-acetamide;
N-Cyclohexylmethyl-2-(3-{2-[2-(3,5-dihydroxy-phenyl)-2-hydroxy-ethylamino]-propyl}-phenyl)-acetamide;
1-(3,4-Dihydro-1H-isoquinolin-2-yl)-2-(3-{2-[2-(3,5-dihydroxy-phenyl)-2-hydroxy-ethylamino]-propyl}-phenyl)-ethanone;
N-Benzyl-2-(3-{2-[2-(3,5-dihydroxy-phenyl)-2-hydroxy-ethylamino]-propyl}-phenyl)-N-methyl-acetamide;
2-(3-{2-[2-(3,5-Dihydroxy-phenyl)-2-hydroxy-ethylamino]-propyl}-phenyl)-N-(2-hydroxy-benzyl)-acetamide;
N-(4-Cyano-benzyl)-2-(3-{2-[2-(3,5-dihydroxy-phenyl)-2-hydroxy-ethylamino]-2-methyl-propyl}-phenyl)-acetamide;
N-(2,4-Dichloro-benzyl)-2-(3-{2-[2-(3,5-dihydroxy-phenyl)-2-hydroxy-ethylamino]-2-methyl-propyl}-phenyl)-acetamide;
N-(Benzyl)-2-(3-{2-[2-(3,5-dihydroxy-phenyl)-2-hydroxy-ethylamino]-2-methyl-propyl}-phenyl)-acetamide;
N-(2-Chlorobenzyl)-2-(3-{2-[2-(3,5-dihydroxy-phenyl)-2-hydroxy-ethylamino]-2-methyl-propyl}-phenyl)-acetamide;
N-(3-Methoxybenzyl)-2-(3-{2-[2-(3,5-dihydroxy-phenyl)-2-hydroxy-ethylamino]-2-methyl-propyl}-phenyl)-acetamide;
N-(Cyclohexylmethyl)-2-(3-{2-[2-(3,5-dihydroxy-phenyl)-2-hydroxy-ethylamino]-2-methyl-propyl}-phenyl)-acetamide;
2-(3-{2-[2-(3,5-Dihydroxy-phenyl)-2-hydroxy-ethylamino]-2-methyl-propyl}-phenyl)-N-phenethyl-acetamide;
2-(3-{2-[2-(3,5-Dihydroxy-phenyl)-2-hydroxy-ethylamino]-2-methyl-propyl}-phenyl)-N-(4-chlorophenethyl)-acetamide;
2-(3-{2-[2-(3,5-Dihydroxy-phenyl)-2-hydroxy-ethylamino]-2-methyl-propyl}-phenyl)-N-(4-phenylphenethyl)-acetamide;
2-(3-{2-[2-(3,5-Dihydroxy-phenyl)-2-hydroxy-ethylamino]-2-methyl-propyl}-phenyl)-N-(4'-hydroxy-biphenyl-3-ylmethyl)-acetamide;
N-Cycloheptyl-2-(3-{2-[2-(3,5-dihydroxy-phenyl)-2-hydroxy-ethylamino]-2-methyl-propyl}-phenyl)-acetamide;
2-(3-{2-[2-(3,5-Dihydroxy-phenyl)-2-hydroxy-ethylamino]-propyl}-phenyl)-N-phenethyl-acetamide;
2-(3-{2-[2-(3,5-Dihydroxy-phenyl)-2-hydroxy-ethylamino]-propyl}-phenyl)-N-(2-methylsulfanyl-benzyl)-acetamide;
N-(2,6-Dichloro-benzyl)-2-(3-{2-[2-(3,5-dihydroxy-phenyl)-2-hydroxy-ethylamino]-propyl}-phenyl)-acetamide;
2-(3-{2-[2-(3,5-Dihydroxy-phenyl)-2-hydroxy-ethylamino]-propyl}-phenyl)-N-indan-2-yl-acetamide;
N-(2-Chloro-6-fluorobenzyl)-2-(3-{2-[2-(3,5-dihydroxy-phenyl)-2-hydroxy-ethylamino]-propyl}-phenyl)-acetamide;
N-(4-Chlorobenzyl)-2-(3-{2-[2-(3,5-dihydroxy-phenyl)-2-hydroxy-ethylamino]-propyl}-phenyl)-acetamide;
N-(2,5-Dichloro-benzyl)-2-(3-{2-[2-(3,5-dihydroxy-phenyl)-2-hydroxy-ethylamino]-2-methyl-propyl}-phenyl)-acetamide;
N-(3,5-Dichloro-benzyl)-2-(3-{2-[2-(3,5-dihydroxy-phenyl)-2-hydroxy-ethylamino]-2-methyl-propyl}-phenyl)-acetamide;
N-(2,6-Dichloro-benzyl)-2-(3-{2-[2-(3,5-dihydroxy-phenyl)-2-hydroxy-ethylamino]-2-methyl-propyl}-phenyl)-acetamide;
N-Biphenyl-2-ylmethyl-2-(3-{2-[2-(3,5-dihydroxy-phenyl)-2-hydroxy-ethylamino]-2-methyl-propyl}-phenyl)-acetamide;
N-(2-Chlorobenzyl)-2-(3-{2-[2-(3,5-dihydroxy-phenyl)-2-hydroxy-ethylamino]-propyl}-phenyl)-acetamide;
N-(3-Methoxybenzyl)-2-(3-{2-[2-(3,5-dihydroxy-phenyl)-2-hydroxy-ethylamino]-propyl}-phenyl)-acetamide;
N-(3-Trifluoromethylbenzyl)-2-(3-{2-[2-(3,5-dihydroxy-phenyl)-2-hydroxy-ethylamino]-propyl}-phenyl)-acetamide;
N-(3,4-Difluorobenzyl)-2-(3-{2-[2-(3,5-dihydroxy-phenyl)-2-hydroxy-ethylamino]-propyl}-phenyl)-acetamide;
N-(2-Methoxybenzyl)-2-(3-{2-[2-(3,5-dihydroxy-phenyl)-2-hydroxy-ethylamino]-propyl}-phenyl)-acetamide;
N-(3,4-Dimethylbenzyl)-2-(3-{2-[2-(3,5-dihydroxy-phenyl)-2-hydroxy-ethylamino]-propyl}-phenyl)-acetamide;
N-(3,4-Dimethoxybenzyl)-2-(3-{2-[2-(3,5-dihydroxy-phenyl)-2-hydroxy-ethylamino]-propyl}-phenyl)-acetamide;
4-{[2-(3-{2-[2-(3,5-Dihydroxy-phenyl)-2-hydroxy-ethylamino]-propyl}-phenyl)-acetylamino]-methyl}-benzamide;
2-(3-{2-[2-(3,5-Dihydroxy-phenyl)-2-hydroxy-ethylamino]-propyl}-phenyl)-N-indan-1-yl-acetamide;
3-{2-[2-(3,5-Dihydroxy-phenyl)-2-hydroxy-ethylamino]-propyl}-N-[2-(3-fluoro-phenyl)-ethyl]-benzamide;
3-{2-[2-(3,5-Dihydroxy-phenyl)-2-hydroxy-ethylamino]-propyl}-N-[2-(2-chloro-phenyl)-ethyl]-benzamide;
2-(3-{2-[2-(3,5-Dihydroxy-phenyl)-2-hydroxy-ethylamino]-propyl}-phenyl)-N-naphthalen-1-ylmethyl-acetamide;
2-(3-{2-[2-(3,5-Dihydroxy-phenyl)-2-hydroxy-ethylamino]-propyl}-phenyl)-N-(2-fluoro-5-trifluoromethyl-benzyl)-acetamide;
2-(3-{2-[2-(3,5-Dihydroxy-phenyl)-2-hydroxy-ethylamino]-propyl}-phenyl)-N-(3-chlorobenzyl)-acetamide;
2-(3-{2-[2-(3,5-Dihydroxy-phenyl)-2-hydroxy-ethylamino]-propyl}-phenyl)-N-(4-fluoro-3-trifluoromethyl-benzyl)-acetamide;
2-(3-{2-[2-(3,5-Dihydroxy-phenyl)-2-hydroxy-ethylamino]-2-methyl-propyl)-phenyl}-N-(2-methylsulfanyl-benzyl)-acetamide;

4-{[2-(3-{2-[2-(3,5-Dihydroxy-phenyl)-2-hydroxy-ethylamino]-2-methyl-propyl}-phenyl)-acetylamino]-methyl}-benzamide;
2-(3-{2-[2-(3,5-Dihydroxy-phenyl)-2-hydroxy-ethylamino]-2-methyl-propyl}-phenyl)-N-(4-sulfamoyl-benzyl)-acetamide;
4-{[2-(3-{2-[2-(3,5-Dihydroxy-phenyl)-2-hydroxy-ethylamino]-2-methyl-propyl}-phenyl)-acetylamino]-methyl}-benzoic acid methyl ester;
N-(1-Benzyl-piperidin-4-yl)-2-(3-{2-[2-(3,5-dihydroxy-phenyl)-2-hydroxy-ethylamino]-2-methyl-propyl}-phenyl)-acetamide;
3-{2-[2-(3,5-Dihydroxy-phenyl)-2-hydroxy-ethylamino]-propyl}-N-[2-phenethyl]-benzamide;
3-{2-[2-(3,5-Dihydroxy-phenyl)-2-hydroxy-ethylamino]-propyl}-N-[2-(5-fluoro-2-methyl-phenyl)-ethyl]-benzamide;
3-{2-[2-(3,5-Dihydroxy-phenyl)-2-hydroxy-ethylamino]-propyl}-N-[2-(2-trifluoromethyl-phenyl)-ethyl]-benzamide;
3-{2-[2-(3,5-Dihydroxy-phenyl)-2-hydroxy-ethylamino]-propyl}-N-(2-naphthalen-1-yl-ethyl)-benzamide;
3-{2-[2-(3,5-Dihydroxy-phenyl)-2-hydroxy-ethylamino]-propyl}-N-[2-(2,4,5-trimethyl-phenyl)-ethyl]-benzamide;
3-{2-[2-(3,5-Dihydroxy-phenyl)-2-hydroxy-ethylamino]-propyl}-N-[2-(2,3-dimethyl-phenyl)-ethyl]-benzamide;
3-{2-[2-(3,5-Dihydroxy-phenyl)-2-hydroxy-ethylamino]-propyl}-N-[2-(2-hydroxy-3-chloro-phenyl)-ethyl]-benzamide;
3-{2-[2-(3,5-Dihydroxy-phenyl)-2-hydroxy-ethylamino]-propyl}-N-[2-(4-chloro-phenyl)-ethyl]-benzamide;
3-{2-[2-(3,5-Dihydroxy-phenyl)-2-hydroxy-ethylamino]-propyl}-N-[2-(2-hydroxy-5-chloro-phenyl)-ethyl]-benzamide;
3-{2-[2-(3,5-Dihydroxy-phenyl)-2-hydroxy-ethylamino]-propyl}-N-[2-(2-chloro-4-fluoro-phenyl)-ethyl]-benzamide;
2-(3-{2-[2-(3,5-Dihydroxy-phenyl)-2-hydroxy-ethylamino]-2-methyl-propyl}-phenyl)-N-(2-methyl-benzyl)-acetamide;
2-(3-{2-[2-(3,5-Dihydroxy-phenyl)-2-hydroxy-ethylamino]-2-methyl-propyl}-phenyl)-N-(3-methyl-benzyl)-acetamide;
2-(3-{2-[2-(3,5-Dihydroxy-phenyl)-2-hydroxy-ethylamino]-2-methyl-propyl}-phenyl)-N-(4-methyl-benzyl)-acetamide;
2-(3-{2-[2-(3,5-Dihydroxy-phenyl)-2-hydroxy-ethylamino]-2-methyl-propyl}-phenyl)-N-(2-methoxy-benzyl)-acetamide
2-(3-{2-[2-(3,5-Dihydroxy-phenyl)-2-hydroxy-ethylamino]-2-methyl-propyl}-phenyl)-N-(4-methoxy-benzyl)-acetamide;
2-(3-{2-[2-(3,5-Dihydroxy-phenyl)-2-hydroxy-ethylamino]-2-methyl-propyl}-phenyl)-N-(2,3-dimethyl-benzyl)-acetamide;
2-(3-{2-[2-(3,5-Dihydroxy-phenyl)-2-hydroxy-ethylamino]-2-methyl-propyl}-phenyl)-N-(3,4-dimethyl-benzyl)-acetamide;
2-(3-{2-[2-(3,5-Dihydroxy-phenyl)-2-hydroxy-ethylamino]-2-methyl-propyl}-phenyl)-N-(2-chloro-6-methyl-benzyl)-acetamide;
2-(3-{2-[2-(3,5-Dihydroxy-phenyl)-2-hydroxy-ethylamino]-2-methyl-propyl}-phenyl)-N-(3-chloro-4-methyl-benzyl)-acetamide;
2-(3-{2-[2-(3,5-Dihydroxy-phenyl)-2-hydroxy-ethylamino]-2-methyl-propyl}-phenyl)-N-[2-(6-methoxy-naphthalen-2-yl)-ethyl]-acetamide;
N-(2-Chlorobenzyl)-3-(3-{2-[2-(3,5-dihydroxyphenyl)-2-hydroxyethylamino]propyl}phenyl)propionamide;
N-(2,6-Dichlorobenzyl)-3-(3-{2-[2-(3,5-dihydroxyphenyl)-2-hydroxyethylamino]propyl}phenyl)propionamide;
1-(3,4-Dihydro-1H-isoquinolin-2-yl)-3-(3-{2-[2-(3,5-dihydroxyphenyl)-2-hydroxyethylamino]propyl}phenyl)propan-1-one;
N-(2-Chloro-4-fluorobenzyl)-2-(3-{2-[2-(3,5-dihydroxyphenyl)-2-hydroxyethylamino]propyl}phenyl)acetamide;
N-(4-Bromobenzyl)-2-(3-{2-[2-(3,5-dihydroxyphenyl)-2-hydroxyethylamino]-2-methylpropyl}phenyl)acetamide;
2-(3-{2-[2-(3,5-Dihydroxyphenyl)-2-hydroxyethylamino]-2-methylpropyl}phenyl)-N-(3,4-dimethylphenyl)acetamide;
2-(3-{2-[2-(3,5-Dihydroxyphenyl)-2-hydroxyethylamino]propyl}phenyl)-N-(2,3-dimethylbenzyl)acetamide;
2-(3-{2-[2-(3,5-Dihydroxyphenyl)-2-hydroxyethylamino]propyl}phenyl)-N-(4-fluorobenzyl)acetamide;
2-(3-{2-[2-(3,5-Dihydroxyphenyl)-2-hydroxyethylamino]propyl}phenyl)-1-(4-pyridin-2-ylpiperazin-1-yl)ethanone; and,
2-(3-{2-[2-(3,5-Dihydroxyphenyl)-2-hydroxyethylamino]-2-methylpropyl}phenyl)-N-(2-phenylpropyl)acetamide.

According to one aspect of the present invention, the compounds of formula (1) wherein the $(CH_2)_n$—$C(=O)Q^1$ group is in the meta position are generally preferred.

Pharmaceutically acceptable salts of the compounds of formula (1) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:
(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (1) contains a carboxylic acid functionality (—COOH), an ester thereof, for example, a compound wherein the hydrogen of the carboxylic acid functionality of the compound of formula (1) is replaced by $(C_1-C_8)$alkyl;
(ii) where the compound of formula (1) contains an alcohol functionality (—OH), an ether thereof, for example, a compound wherein the hydrogen of the alcohol functionality of the compound of formula (1) is replaced by $(C_1-C_6)$alkanoyloxymethyl; and
(iii) where the compound of formula (1) contains a primary or secondary amino functionality (—$NH_2$ or —NHR where R≠H), an amide thereof, for example, a compound wherein, as the case may be, one or both hydrogens of the amino functionality of the compound of formula (1) is/are replaced by $(C_1-C_{10})$alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a methyl group, an hydroxymethyl derivative thereof (—$CH_3$→—$CH_2OH$):
(ii) where the compound of formula (1) contains an alkoxy group, an hydroxy derivative thereof (—OR→—OH);
(iii) where the compound of formula (1) contains a tertiary amino group, a secondary amino derivative thereof (—$NR^1R^2$→—$NHR^1$ or —$NHR^2$);
(iv) where the compound of formula (1) contains a secondary amino group, a primary derivative thereof (—$NHR^1$ →—$NH_2$);
(v) where the compound of formula (1) contains a phenyl moiety, a phenol derivative thereof (—Ph→—PhOH); and
(vi) where the compound of formula (1) contains an amide group, a carboxylic acid derivative thereof (—$CONH_2$→COOH).

Compounds of formula (1) containing one or more asymmetric carbon atoms can exist as two or more stereoisomers. Where a compound of formula (1) contains an alkenyl or alkenylene group, geometric cisitrans (or Z/E) isomers are possible. Where structural isomers are interconvertible via a low energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer (s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

According to one aspect of the present invention, the (R,R)-stereoisomer of the formula below, wherein $R^1$ is hydrogen and $R^2$ is $C_1$-$C_4$ alkyl, preferably methyl, and n and $Q^1$ are as defined above, is generally preferred:

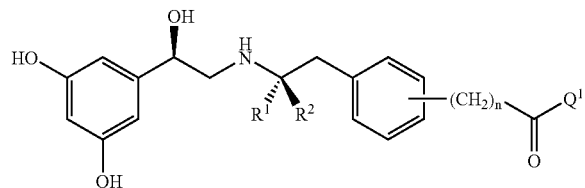

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (1), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical_compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:
(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids, such as DAGR (dissociated agonists of the corticoid receptor),
(k) Monoclonal antibodies active against endogenous inflammatory entities,
(l) Anti-tumor necrosis factor (anti-TNF-α) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκβ pathway, e.g. IKK inhibitors,
(w) modulators of cytokine signalling pathyways such as p38 MAP kinase, syk kinase or JAK kinase inhibitor,
(x) Agents that can be classed as mucolytics or anti-tussive,
(y) Antibiotics,
(z) HDAC inhibitors, and,
(aa) PI3 kinase inhibitors.

According to the present invention, combination of the compounds of formula (1) with
H3 antagonists,
Muscarinic M3 receptor antagonists,
PDE4 inhibitors,
glucocorticosteroids,
Adenosine A2a receptor agonists,
Modulators of cytokine signalling pathyways such as p38 MAP kinase or syk kinase, or,
Leukotriene antagonists (LTRAs) including antagonists of $LTB_4$, $LTC_4$, $LTD_4$, and $LTE_4$, are preferred.

According to the present invention, combination of the compounds of formula (1) with
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine,
are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the β2 receptor and thereby have a wide range of therapeutic applications, as described further below, because of the essential role which the β2 receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the β2 receptor is involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions in a mammal, including a human being, in particular the diseases and/or conditions listed above, comprising admidministering said mammal with an effective amount of a compound of formula (1), its pharmaceutically acceptable salts and/or derived forms.

The following examples illustrate the preparation of the compounds of the formula (1):

PREPARATION 1

Diethyl 2,2'-(1,3-phenylene)diacetate

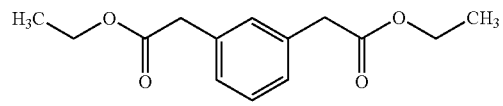

2,2'-(1,3-Phenylene)diacetic acid (10.0 g, 51 mmol) was dissolved in ethanol (100 mL) and the solution treated dropwise with catalytic acetyl chloride (2.5 mL). The reaction mixture was stirred at reflux for 18 hours before being allowed to cool and concentrated under reduced pressure. The residue was taken up in ethyl acetate (100 mL) and washed with sodium bicarbonate solution (3×50 mL) and brine (3×50 mL). The organic phase was dried over magnesium sulphate and concentrated under reduced pressure. The residue was triturated with pentane to yield the title product, 11.8 g.

$^1$HNMR (CDCl$_3$, 400 MHz) δ 1.31 (6H, t), 3.65 (4H, s), 4.20 (4H, q), 7.24-7.36 (4H, m). LRMS: m/z ES$^+$ 251 [MH]$^+$

PREPARATION 2

[3-(2-Ethoxy-2-oxoethyl)phenyl]acetic acid

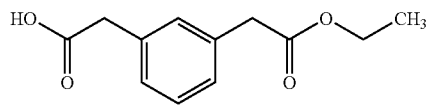

A solution of the diester from preparation 1 (44.3 g, 177 mmol) and 2,2'-(1,3-phenylene)diacetic acid (59.2 g, 308 mmol) in ethanol (24 mL) and dioxan (290 mL) was treated dropwise with 12M hydrochloric acid (4.9 mL, 58.8 mmol). The reaction mixture was stirred and heated under reflux for 18 hours before being allowed to cool and concentrated to low volume. The reaction mixture was diluted with toluene (125 mL) and the resulting slurry filtered. The filtrate was concentrated under reduced pressure and the residue taken up in water and neutralised with sodium bicarbonate. The mixture was diluted with ethyl acetate (200 mL) and the organic layer was separated and washed with sodium bicarbonate solution (5×30 mL) and brine (50 mL). The combined aqueous extracts were acidified to pH 3 with 6M hydrochloric acid and extracted with ether (3×30 mL). The organics were combined, dried over magnesium sulphate and concentrated under reduced pressure. The residue was triturated with pentane giving the title compound as a colourless solid 10.8 g.

¹HNMR (CD₃OD, 400 MHz) δ 1.25 (3H, t), 3.60 (2H, m), 3.63 (2H, m), 4.15 (2H, q), 7.18-7.32 (4H, m) LRMS: m/z ES⁺ 245 [MNa]⁺

PREPARATION 3

[3-(2-Hydroxy-2-methyl-propyl)-phenyl]-acetic acid

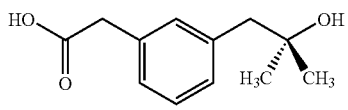

A solution of the acid of preparation 2 (6.85 g, 32 mmol) in diethyl-ether (100 mL) was cooled to 0° C. and treated with a 3M solution of methylmagnesium bromide in ether (23.5 mL, 70.0 mmol). The reaction mixture was allowed to warm gradually to room temperature. After 2 hours the reaction was quenched by addition of saturated aqueous ammonium chloride solution (200 mL). The organic phase was separated and washed with brine (100 mL), dried over magnesium sulfate and concentrated under reduced pressure. Purification by column chromatography on silica gel eluting with pentane: dichloromethane (60:40 to 0:100) gave the title compound as a colourless oil, 6.23 g.

¹H NMR (CDCl₃, 400 MHz) δ 1.22 (6H, s), 2.75 (2H, s), 3.63 (2H, s), 7.12-7.30 (4H, m). LRMS: m/z ES⁺ 209 [MH]⁺

PREPARATION 4

{3-[2-(2-Chloro-acetylamino)-2-methyl-prsopyl]-phenyl}-acetic acid

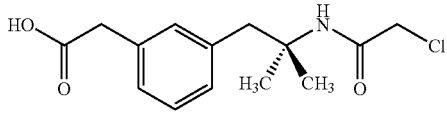

2-Chloroacetonitrile (8.8 mL, 140 mmol) was added to a solution of the alcohol from preparation 3 (16.0 g, 70 mmol), in acetic acid (33 mL). The resulting solution was cooled to 0° C., treated with concentrated sulfuric acid (33 mL), and the reaction mixture allowed to warm gradually to room temperature. After 4 hours the reaction mixture was poured onto ice and basified with solid sodium carbonate. The solution was extracted with ethyl acetate (2×500 mL) and the combined organic extracts dried over magnesium sulphate and concentrated under reduced pressure to give the title product as a colourless solid, 19.0 g.

¹H NMR (CDCl₃, 400 MHz) δ 1.36 (6H, s), 3.02 (2H, s), 3.62 (2H, s) 3.95 (2H, s), 6.19 (1H, br s), 7.06-7.31 (4H, m) LRMS: m/z ES⁻ 282, 284 [M-H]⁻

PREPARATION 5

Methyl [3-(2-amino-2-methylpropyl)phenyl]acetate

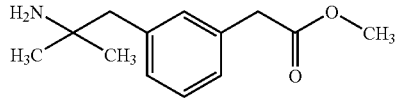

A solution of the amide from preparation 4 (5.1 g, 18 mmol), thiourea (1.6 g, 21 mmol) and acetic acid (18 mL) in methanol (80 mL) was heated to reflux under a nitrogen atmosphere for 16 hours. The reaction mixture was cooled and filtered. The filtrate was concentrated under reduced pressure and the residue dissolved in methanol (150 mL). The solution was saturated with hydrogen chloride gas and then heated to reflux for 16 hours. The solvent was reduced in vacuo and the residue partitioned between ethyl acetate (200 mL) and 5% aqueous sodium carbonate (200 mL). The organic extract was washed with saturated sodium chloride (100 mL), dried over sodium sulphate and reduced in vacuo. The residue was purified on strong cation exchange resin, eluting with methanol and then 2N ammonia in methanol to elute the product. The eluent was concentrated in vacuo to give the title compound as a yellow oil, 2.68 g.

¹H NMR (CDCl₃, 400 MHz) δ 1.14 (6H, s), 2.68 (2H, s), 3.62 (2H, s), 3.69 (3H, s), 7.08-7.16 (3H, m), 7.23-7.27 (1H, m). LRMS : m/z ES⁺ 236 [MH]⁺

PREPARATION 6

1-[3,5-bis(Benzyloxy)phenyl]-2-bromoethanone

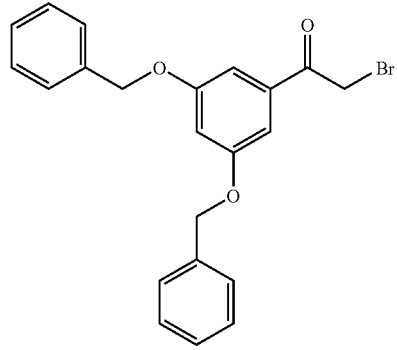

To a stirred solution of 1-[3,5-bis(benzyloxy)phenyl]ethanone (5 g, 15.04 mmol) in tetrahydrofuran (60 mL) and methanol (35 mL) was added tetrabutylammonium tribromide (7.25 g, 15.04 mmol) in tetrahydrofuran (20 mL) at room temperature. The reaction mixture was stirred for 24 hours and the solvent removed in vacuo. The residue was dissolved in ethyl acetate (100 mL) and washed with water (2×50 mL). The combined organic extracts were dried over magnesium sulfate and concentrated to afford the desired compound as a yellow oil in quantitative yield.

PREPARATION 7

Methyl {3-[2-({2-[3,5-bis(benzyloxy)phenyl]-2-hydroxyethyl}amino)-2-methylpropyl]phenyl}acetate

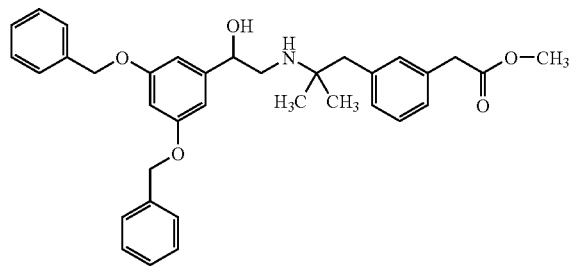

A stirred solution of the compound of preparation 6 (4.7 g, 11.4 mmol), the compound of preparation 5 (2.53 g, 11.4 mmol) and N-ethyldiisopropylamine (2 mL, 11.4 mmol) in tetrahydrofuran (140 mL) were heated under reflux for 24 hours. The reaction mixture was cooled to room temperature, sodium borohydride (647 mg, 17.10 mmol) was added and the mixture stirred for 5 hours at room temperature. The reaction was quenched by addition of methanol (5 mL) and the solvent was evaporated in vacuo. The residual orange oil was partitioned between dichloromethane (60 mL) and saturated sodium hydrogen carbonate solution (40 mL). The phases were separated and the aqueous phase was extracted with dichloromethane (3×40 mL). The organic extracts were combined and concentrated in vacuo. Purification by column chromatography on silica gel using dichloromethane and then dichloromethane:methanol:0.88 ammonia (95:5:0.5) as eluent afforded the desired product, 4.50 g (70%).

$^1$H NMR (400 MHz, CD$_3$OD) δ 1.01 (6H, d), 2.61 (4H, m), 3.58 (2H, s), 3.62 (3H, s), 4.61-4.64 (1H, dd), 5.03 (4H, s), 6.54-6.55 (1H, t), 6.63-6.64 (2H, d), 7.00-7.01 (1H, d), 7.08-7.10 (2H, d), 7.16-7.20 (1H, t), 7.25-7.28 (2H, m), 7.31-7.34 (4H, t), 7.38-7.40 (4H, d). LRMS: m/z APCl$^+$ 554 [MH$^+$].

PREPARATION 8

Methyl [3-(2-{[2-(3,5-dihydroxyphenyl)-2-hydroxyethyl]amino}-2-methylpropyl)phenyl]acetate

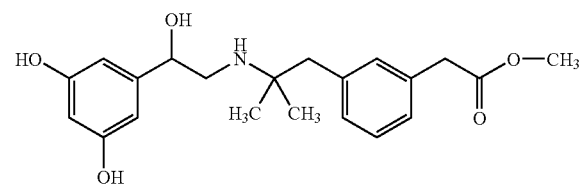

A mixture of the compound of preparation 7 (4.50 g, 8.13 mmol), ammonium formate (3.59 g, 113.86 mmol) and palladium hydroxide on carbon (900 mg) in ethanol (80 mL) was heated under reflux for 24 hours. The reaction mixture was cooled to room temperature, filtered through Arbocel® and washed with methanol (3×20 mL). The filtrate was concentrated in vacuo to give an orange oil as the desired product, 2.64 g (87%).

$^1$H NMR (400 MHz, CD$_3$OD) δ 1.06 (3H, s), 1.07 (3H, s), 2.67-287 (4H, m), 3.62 (2H, s), 3.66 (3H, s), 4.56-4.59 (1H, q), 6.18-6.19 (1H, t), 6.34 (2H, d), 7.03-7.23 (4H, m). LRMS: m/z APCl$^+$ 374 [MH$^+$].

PREPARATION 9

[3-(2-{([2-(3,5-Dihydroxyphenyl)-2-hydroxyethyl]amino}-2-methylpropyl)phenyl]acetic acid

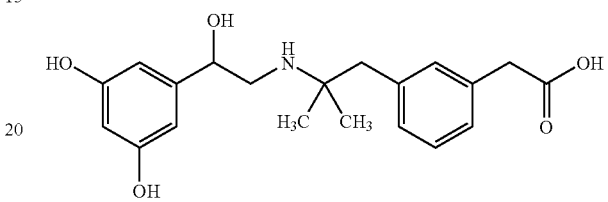

1M Lithium hydroxide solution (21.2 mL, 21.2 mmol) was added dropwise to a solution of the compound of preparation 8 (2.64 g, 7.07 mmol) in tetrahydrofuran (30 mL) and the reaction mixture was stirred for 24 hours. A 1M solution of hydrochloric acid (21.2 mL, 21.2 mmol) was added and the solvent removed in vacuo. The crude residue obtained was azeotroped with methanol, and the product used subsequently without further purification.

$^1$H NMR (400 MHz, DMSO-d$_6$) δ 1.07 (6H, s), 2.74-2.87 (4H, m), 3.39 (2H, s), 4.63-4.61 (1H, d), 6.14-6.15 (1H, t), 6.24-6.25 (2H, d), 6.96-7.22 (4H, m). LRMS: m/z APCl$^+$ 357 [MH$^+$].

PREPARATION 10

1-(3,5-Bis-benzyloxy-phenyl)-2-bromo-ethanol

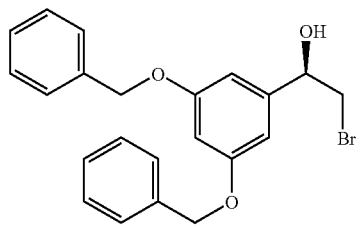

Trimethylboroxine (0.58 mL, 4.20 mmol) in toluene (15 mL) was added to (R)-2-(diphenylhydroxymethylpyrrolidine) (1.48 g, 5.80 mmol) and the reaction stirred under nitrogen for 15 minutes. The solution was concentrated to a volume of 5 mL by distillation at 1 atmosphere and further toluene (10 mL) was added. The distillation/redilution cycle was performed 3 times to furnish an orange solution (volume of toluene 10 mL). This solution was added in one portion to a stirred solution of the compound of preparation 6 (5.00 g, 12.2 mmol) in tetrahydrofurarn (72 mL) at −8° C. under nitrogen. To this mixture a solution of borane dimethylsulfide complex (1.60 mL, 16.8 mmol) in tetrahydrofuran (16 mL) was added by syringe pump over 90 minutes maintaining a temperature of −8° C. Once addition was complete methanol (16 mL) was added by syringe pump over 45 minutes maintaining a temperature of 0° C. and the reaction allowed to warm to room temperature over 12 hours. The solvent was removed in vacuo to give a yellow oil and methanol (80 mL) added and removed in vacuo. Methanol (80 mL) was added and removed in vacuo and the resulting yellow oil dissolved in dichloromethane (500 mL), washed with 1M aqueous hydrochloric acid (96 mL), water (2×120 mL), dried (magnesium sulfate) and the solvent removed in vacuo to furnish the title compound as a cream solid, 4.73 g.

$^1$H NMR (400MHz, CD$_3$OD) δ 3.52 (1H, m), 3.62 (1H, m), 4.82 (1H, dd), 5.09 (4H, s), 6.60 (1H, m), 6.69 (1H, s), 6.70 (1H, s), 7.33 (2H, m), 7.40 (4H, m), 7.45 (5H, m). LRMS: m/z electrospray 413, 415 [M+H$^+$].

PREPARATION 11

[1-(3,5-Bis-benzyloxy-phenyl)-2-bromo-ethoxy]-tert-butyl-dimethyl-silane

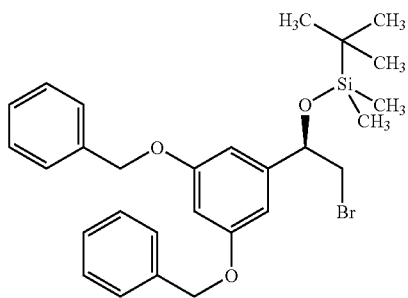

Tert-butyldimethylsilanetriflate (3.40 mL, 7.45 mmol) was added dropwise to a solution of the compound of preparation 10 (3.08 g, 7.45 mmol) and 2,6-lutidine (1.75 mL, 15.0 mmol) in dichloromethane (74 mL) at 0° C., under nitrogen. The reaction was allowed to warm to room temperature over 12 hours and then washed with 1M aqueous hydrochloric acid (2×24 mL), water (2×32 mL), dried (magnesium sulfate) and the solvent removed in vacuo to give a yellow oil. This was purified by column chromatography on silica gel eluting with dichloromethane to furnish the title compound as a colourless oil, 3.51 g.

$^1$H NMR (400 MHz, CD$_3$OD) δ −0.07 (3H, s), 0.13 (3H, s), 0.93 (9H, s), 3.52 (2H, m), 4.86 (1H, dd), 5.10 (4H, s), 6.60 (1H, m), 6.65 (1H, s), 6.66 (1H, s), 7.33 (2H, m), 7.40 (4H, m), 7.45 (4H, m). LRMS: m/z electrospray 549 [M+Na$^+$].

PREPARATION 12

3-{2-[2-(3,5-Bis-benzyloxy-phenyl)-2-(tert-butyl-dimethyl-silanyloxy)-ethylamino]-2-methyl-propyl}-benzoic acid methyl ester

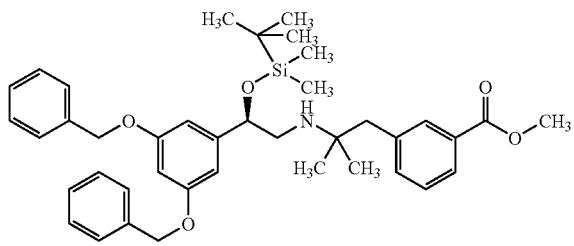

A solution of the compound of preparation 11 (2.54 g, 4.80 mmol) and the compound of preparation 21 (2.00 g, 9.60 mmol) in dichloromethane (40 mL) was heated to 75° C. and the solvent allowed to evaporate off. The resulting melt was heated at 75° C. for 4 days and then allowed to cool to room temperature. The residue was purified by column chromatography on silica gel eluting with dichloromethane:methanol:880 ammonia (100:0:0 then 95:5:0.5) to furnish the title compound as a yellow oil, 2.00 g.

$^1$H NMR (400 MHz, CD$_3$OD) δ −0.18 (3H, s), −0.04 (3H, s), 0.78 (9H, s), 1.11 (3H, s), 1.13 (3H, s), 2.70 (4H, m), 3.92 (3H, s), 4.70 (1H, dd), 5.12 (4H, s), 6.60 (1H, m), 6.62 (1H, s), 6.63 (1H, s), 7.32 (2H, m), 7.38 (6H, m), 7.45 (4H, m), 7.92 (2H, m). LRMS: m/z electrospray 654 [M+H$^+$].

PREPARATION 13

3-{2-[2-(tert-Butyl-dimethyl-silanyloxy)-2-(3,5-di-hydroxy-phenyl)-ethylamino]-2-methyl-propyl}-benzoic acid methyl ester

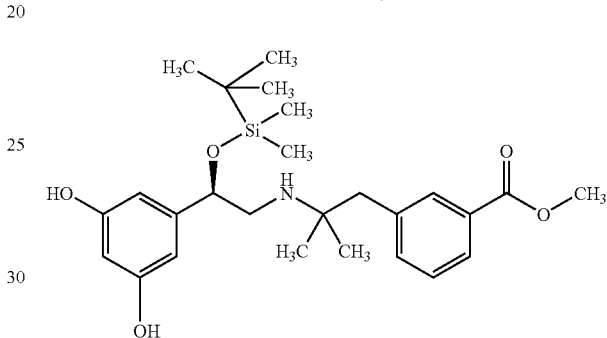

Palladium hydroxide (340 mg) was added in one portion to a stirred solution of the compound of preparation 12 (1.97 g, 3.00 mmol) and ammonium formate (2.17 g, 47.1 mmol) in ethanol (31 mL) at room temperature. The reaction was heated under reflux for 2 hours and allowed to cool to room temperature. The reaction was filtered through Arbocel® and the filtrate concentrated in vacuo to furnish the title compound as a white foam, 1.41 g.

$^1$H NMR (400 MHz, CD$_3$OD) δ −0.11 (3H, s), −0.00 (3H, s), 0.81 (9H, s), 1.13 (3H, s), 1.15 (3H, s), 2.70 (4H, m), 3.96 (3H, s), 4.63 (1H, dd), 6.22 (1H, m), 6.33 (1H, s), 6.34 (1H, s), 7.42 (2H, m), 7.92 (2H, m). LRMS: m/z electrospray 474 [M+H$^+$], 496 [MNa$^+$], 472 [M−H$^−$].

PREPARATION 14

3-{2-[2-(tert-Butyl-dimethyl-silanyloxy)-2-(3,5-di-hydroxy-phenyl)-ethylamino]-2-methylpropyl}-benzoic acid

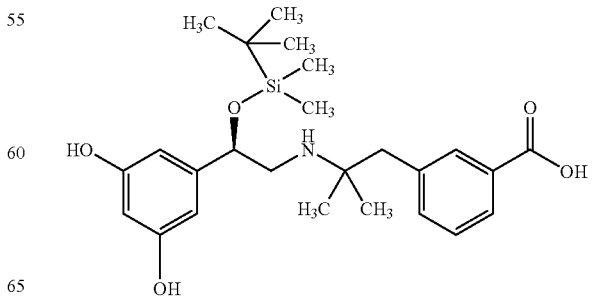

1M aqueous lithium hydroxide (9.00 mL, 9.00 mmol) was added in one portion to a stirred solution of the compound of preparation 13 (1.39 g, 2.93 mmol) in tetrahydrofuran (30 mL) at room temperature. The reaction was stirred at room temperature for 24 hours and 1M aqueous hydrochloric acid (9.00 mL, 9.00 mmol) was added in one portion. The solvent was removed in vacuo to furnish the title compound as a brown foam, 2.06 g.

$^1$H NMR (400 MHz, CD$_3$OD) δ −0.05 (3H, s), 0.07 (3H, s), 0.83 (9H, s), 1.35 (3H, s), 1.37 (3H, s), 3.08 (2H, m), 3.25 (2H, m), 4.93 (1H, m), 6.29 (1H, m), 6.38 (1H, s), 6.39 (1H, s), 7.42 (2H, m), 7.92 (1H, m), 8.00 (1H, m). LRMS: m/z electrospray 460 [M+H$^+$].

PREPARATION 15

3-{2-[2-(tert-Butyl-dimethyl-silanyloxy)-2-(3,5-dihydroxy-phenyl)-ethylamino]-2-methyl-propyl}-N-[2-(4-chloro-phenyl)-ethyl]-benzamide

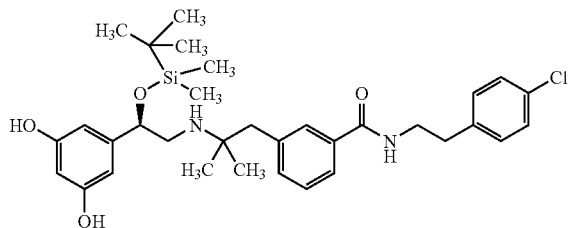

4-Chlorophenethylamine (967 mg, 6.20 mmol), triethylamine (1.00 mL, 7.20 mmol), hydroxybenzotriazole (567 mg, 4.20 mmol) and 1-(3-dimethylaminopropyl)-3-ethylcarbodiimide hydrochloride (910 mg, 4.70 mmol) were added to a stirred solution of the compound of preparation 14 (2.06 g, 3.50 mmol) in N,N-dimethylformamide (35 mL) at room temperature under nitrogen. The reaction was stirred for 12 hours and the solvent removed in vacuo, the residue was then azeotroped with toluene (20 mL) and purified by column chromatography on silica gel eluting with dichloromethane: methanol:880 ammonia (100:0:0 then 95:5:0.5 then 90:10:1) and recolumned eluting with ethyl acetate:pentane:880 ammonia (0:100:0 changing to 80:20:5 in 10% steps) to furnish the title compound as a cream foam, 773 mg.

$^1$H NMR (400 MHz, CD$_3$OD) δ −0.10 (3H, s), 0.01 (3H, s), 0.84 (9H, s), 1.12 (3H, s), 1.14 (3H, s), 2.74 (4H, m), 3.94 (2H, m), 3.62 (2H, m), 4.66 (1H, dd), 6.22 (1H, m), 6.34 (1H, s), 6.35 (1H, s), 7.42 (6H, m), 7.67 (2H, m). LRMS: m/z electrospray 597 [M+H$^+$].

PREPARATION 16

1-(3-Bromophenyl)-2-methylpropan-2-ol)

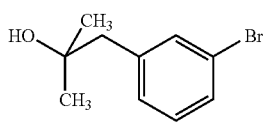

Methylmagnesium bromide (3M solution in diethylether, 51.6 mL, 155 mmol) was slowly added to a solution of 1-(3-bromo-phenyl)propan-2-one (15.0 g, 70 mmol) in dry diethylether (200 mL) at 0° C. The resulting mixture was left for 3 hours, then cooled to 0° C. and slowly quenched with saturated aqueous ammonium chloride solution. The organic phase was washed with brine and dried (sodium sulfate). The yellow oil was then purified by column chromatography on silica gel eluting with dichloromethane:pentane:methanol (90:5:5 by volume to afford a pale yellow oil (13.26 g).

$^1$H NMR (400 MHz, CDCl$_3$) δ=7.40 (2H, m), 7.15 (2H, m), 2.74 (2H, s), 1.42 (1H, bs), 1.22 (6H, s).

PREPARATION 17

N-[2-(3-Bromophenyl)-1,1-dimethylethyl]-2-chloroacetamide

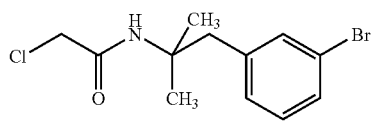

Chloroacetonitrile (6.63 mL, 105 mmol) was added to a stirred solution of 1-(3-bromophenyl)-2-methylpropan-2-ol) (Preparation 16) (12.0 g, 52.0 mmol) in acetic acid (25 mL) at room temperature. The resulting solution was cooled to 0° C. and concentrated sulfuric acid (25 mL) was added keeping the temperature <10° C. The resulting solution was left to stir for 1 hour and then poured onto ice and basified by the addition of solid potassium carbonate. The product was extracted with ethyl acetate (2×500 mL), the organics combined and washed with water (50 mL), dried (sodium sulfate) and the solvent removed in vacuo to afford the title compound as an orange solid (16.08 g).

$^1$H NMR (400 MHz, CDCl$_3$) δ=7.39-7.32 (1H, d), 7.26 (1H, s), 7.1-7.13 (1H, t), 7.08-7.03 (1H, d), 6.17 (1H, bs), 3.94 (2H, s), 3.02 (2H, s), 1.37 (6H, s). CHN for C$_{12}$H$_{15}$BrClNO calc. (found): C 47.32 (47.26), H 4.96 (4.87), N 4.60 (4.65). LRMS (electrospray) m/z 306 [M+H]$^+$

PREPARATION 18

2-(3-Bromophenyl)-1,1-dimethylethylamine

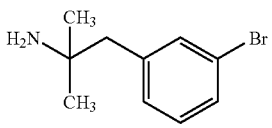

A solution of N-[2-(3-bromophenyl)-1,1-dimethylethyl]-2-chloroacetamide (Preparation 17) (32.0 g, 105 mmol), thiourea (9.60 g, 126 mmol) and acetic acid (50 mL) in ethanol (250 mL) was heated to reflux overnight. The reaction mixture was cooled to room temperature and filtered, the filtrate was concentrated in vacuo and basified using aqueous sodium hydroxide solution (1M, 450 mL). The product was extracted with dichloromethane (2×500 mL) and the combined organics washed with brine (50 mL), dried (sodium sulfate) and the solvent removed in vacuo to afford the title compound as a black oil (23 g).

¹H NMR (400 MHz, CDCl₃) δ=7.36-7.32 (2H, m), 7.16-7.08 (2H, m), 2.62 (2H, s), 1.84 (2H, bs), 1.12 (6H, s). LRMS (electrospray) m/z 228 [M+H]⁺

PREPARATION 19

[2-(3-Bromophenyl)-1,1-dimethylethyl]carbamic acid tert-butyl ester

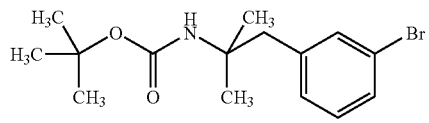

2-(3-Bromophenyl)-1,1-dimethylethylamine (Preparation 18) (5.0 g, 22 mmol) was treated with di-tert-butyl dicarbonate (5.26 g, 24 mmol) in dichloromethane (50 mL) and stirred for 20 hours. The reaction mixture was washed with water (50 mL) and the combined organics dried (sodium sulfate) and the solvent removed in vacuo. The crude material was purified using a cation exchange column (methanol followed by 2M ammonia in methanol), followed by purification by flash column chromatography on silica gel eluting with dichloromethane to afford the title compound as a brown oil (7.23 g).

¹H NMR (400 MHz, CDCl₃) δ=7.35 (1H, d), 7.30 (1H, s), 7.15-7.11 (1H, t), 7.05 (1H, d), 4.24 (1H, bs), 2.97 (2H, s), 1.50 (9H, s), 1.27 (6H, s). LRMS (electrospray) m/z 350 [M+NH₄]⁺

PREPARATION 20

3-(2-tert-Butoxycarbonylamino-2-methylpropyl)benzoic acid methyl ester

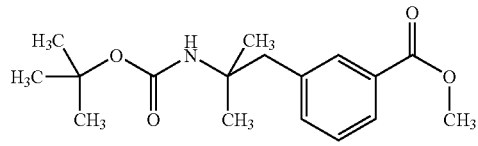

A solution of [2-(3-bromophenyl)-1,1-dimethylethyl]carbamic acid tert-butyl ester (Preparation 19) (7.0 g, 21 mmol), [1,1'-bis(diphenylphosphino)ferrocene]dichloropalladium (II) (1.74 g, 2.1 mmol) and triethylamine (5.94 mL, 43 mmol) in methanol (250 mL) was heated to 100° C. under 100 psi carbon monoxide for 12 hours. The reaction mixture was filtered through Arbocel® and the filtrate concentrated in vacuo and purified by flash column chromatography on silica gel eluting with dichloromethane:pentane (50:50 by volume) to afford the title compound as a yellow solid (3.76 g).

¹H NMR (400 MHz, CDCl₃) δ=7.92-7.90 (1H, m), 7.82 (1H, s), 7.35-7.34 (2H, m), 4.24 (1H, bs), 3.90 (3H, s), 3.05 (2H, s), 1.48 (9H, s), 1.26 (6H, s). LRMS (electrospray) m/z 208 [M+H-BOC]⁺

PREPARATION 21

3-(2-Amino-2-methylpropyl)benzoic acid methyl ester

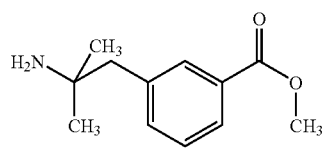

A solution of 3-(2-tert-butoxycarbonylamino-2-methylpropyl)benzoic acid methyl ester (Preparation 20) (1.6 g, 5.2 mmol) in dichloromethane (160 mL) at 0° C. was treated with trifluoroacetic acid (13.6 mL) and left to warm to room temperature over 2 hours. The solvent was removed in vacuo and the product purified by cation exchange chromatography (methanol followed by 2M ammonia in methanol) to yield the title compound as an amber oil (1.06 g).

¹H NMR (400 MHz, CDCl₃) δ=7.90-7.88 (1H, m), 7.84 (1H, s), 7.36-7.35 (2H, m), 3.90 (3H, s), 2.71 (2H, s), 1.67 (2H, bs), 1.12 (6H, s). LRMS (electrospray) m/z 208 [M+H]⁺

PREPARATION 22

Methyl {3-[(2R)-2-aminopropyl]phenyl}acetate

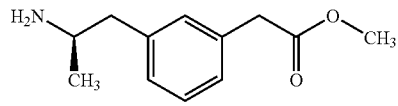

A solution of methyl [3-((2R)-2-{[(1R)-1-phenyl-ethyl]-amino}-propyl)-phenyl]-acetate hydrochloride (Preparation 23) (7.69 g, 22 mmol) and ammonium formate (6.94 g, 110 mmol) was heated to 75° C. in the presence of 20% palladium hydroxide-on-charcoal (Pd(OH)₂/C, 2.00 g). After 90 minutes the reaction mixture was cooled to room temperature, filtered through Arbocel® and the filtrate concentrated in vacuo. The residue was partitioned between dichloromethane (100 mL) and 880 ammonia (100 mL) and the organic phase separated. The aqueous phase was extracted dichloromethane (100 mL) and the combined organic extracts dried (magnesium sulfate) and reduced in vacuo to give the title compound as a colourless oil (4.78 g).

¹H NMR (400 MHz, CD₃OD): δ=7.27-7.23 (1H, t), 7.13-7.09 (3H, m), 3.67 (3H, s), 3.63 (2H, s), 3.12-3.05 (1H, m), 2.67-2.57 (2H, m), 1.06 (3H, d) ppm. LRMS (electrospray): m/z [M+H]⁺ 208, [M+Na]⁺ 230.

PREPARATION 23

Methyl [3-((2R)-2[{(1R)-1-phenyl-ethyl]-amino}-propyl)-phenyl]-acetate hydrochloride

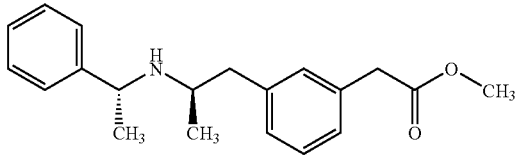

A solution of methyl [3-(2-oxopropyl)phenyl]acetate (Preparation 24) (8.50 g, 41.2 mmol), (R)-α-methyl benzylamine (4.8 mL, 37.2 mmol), sodium triacetoxyborohydride (11.6 g, 56 mmol) and acetic acid (2.2 mL, 38 mmol) in dichloromethane (400 mL) was stirred at room temperature for 48 hours. The reaction mixture was quenched by addition of saturated aqueous sodium bicarbonate (200 mL) and allowed to stir until effervescence ceased. The organic phase was separated and the aqueous phase extracted with dichloromethane (100 mL). The combined organic extracts were dried (magnesium sulfate) and reduced in vacuo. Purification by flash column chromatography eluting with dichloromethane:methanol: ammonia (99:1:0.1 to 95:5:0.5 by volume) gave a 4:1 mixture of diastereomers (R,R major) as a pale yellow oil (8.71 g). Treatment with hydrogen chloride (40 mL of a 1M solution in methanol, 40 mmol) followed by three successive crystallisations (diisopropylether/ methanol) gave the title compound as a white crystalline solid (5.68 g).

$^1$H NMR (400 MHz, CD$_3$OD): δ=7.52-7.48 (5H, m), 7.28-7.25 (1H, m), 7.18-7.16 (1H, m), 7.02-6.99 (2H, m), 4.59 (1H, q), 3.62 (2H, s), 3.30 (3H, s), 3.30-3.25 (1H, m), 3.26-3.15 (1H, m), 2.66-2.60 (1H, m), 1.68 (3H, d), 1.18, (3H, d) ppm. LRMS (electrospray): m/z [M+H]$^+$ 312, [M+Na]$^+$ 334.

PREPARATION 24

Methyl [3-(2-oxopropyl)phenyl]acetate

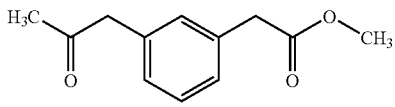

Tributyltin methoxide (28.3 mL, 98 mmol), preparation 25 (15.0 g, 65 mmol), isopropenyl acetate (10.8 mL, 98 mmol), palladium(II)acetate (750 mg, 3.30 mmol) and tri-ortho-tolylphosphine (2.0 g, 6.5 mmol) were stirred together in toluene (75 mL) at 100° C. under nitrogen for 5 hours. After cooling the reaction was diluted with ethyl acetate (150 mL) and 4M aqueous potassium fluoride solution (90 mL) and stirred for 15 minutes. The mixture was filtered through arbocel and the organic phase separated and reduced in vacuo. The residue was purified by flash column chromatography silica gel eluting with a solvent gradient of diethyl ether: pentane (0:100 to 25:75, by volume) changing to dichloromethane to give the title compound as a pale yellow oil (12.6 g).

$^1$H NMR (400 MHz, CDCl$_3$): δ=7.30 (1H, t), 7.19 (1H, d), 7.13-7.10 (2H, m), 3.69 (5H, s), 3.61 (2H, s), 2.15 (3H, s) ppm. LRMS (electrospray): m/z [M+NH$_4$]$^+$ 224, [M+Na]$^+$ 229.

PREPARATION 25

Methyl (3-bromophenyl)acetate

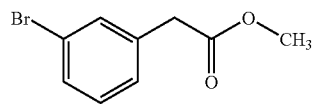

Acetyl chloride (0.7 mL, 9.3 mmol) was slowly added to a solution of (3-bromo-phenyl)-acetic acid (20.0 g, 93 mmol) in methanol (500 mL) at 0° C. under nitrogen and the reaction was allowed to warm gradually to room temperature over a period of 5 hours. The solvent was removed in vacuo and the residual oil was redissolved in dichloromethane, dried (sodium sulfate) and concentrated in vacuo to give the title compound as a colourless oil (20.6 g).

$^1$H NMR (400 MHz, CDCl$_3$): δ=7.37-7.45 (2H, m), 7.24-7.17 (2H, m), 3.70 (3H, s), 3.59 (2H, s) ppm. LRMS (electrospray): m/z [M+Na]$^+$ 253.

PREPARATION 26

[3-((2R)-2-{[(1R)-1-Phenyl-ethyl]-amino}-propyl)-phenyl]-acetic acid

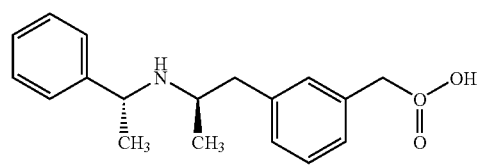

1M aqueous lithium hydroxide (90 mL, 90 mmol) was added in one portion to a stirred solution of the compound of preparation 23 (13.5 g, 43.5 mmol) in methanol (2000 mL) at room temperature. The reaction was stirred at room temperature for 24 hours and 1M aqueous hydrochloric acid (90 mL, 90 mmol) was added in one portion. The solvent was removed in vacuo to reduce the volume to 80 mL and the white precipitate removed by filtration and washed with water (20 mL), 20% ethanol in water (100 mL), dried to furnish the title compound as a white solid, 11.8 g.

$^1$H NMR (400 MHz, CD$_3$OD) δ 1.16 (3H, d), 1.62 (3H, d), 2.64 (1H, m), 3.20 (2H, m), 3.46 (2H, s), 4.42 (1H, q), 6.91 (1H, d), 7.08 (1H, s), 7.19 (1H, s), 7.20 (1H, m), 7.48 (5H, m). LRMS: m/z electrospray 298 [M+H$^+$], 296 [M−H$^−$].

PREPARATION 27

N-Adamantan-1-yl-2-{3-[2-(1-phenyl-ethylamino)-propyl]-phenyl}-acetamide

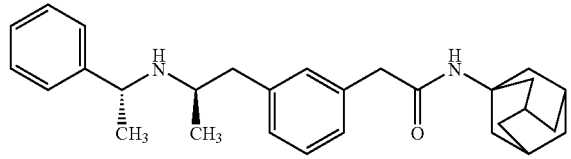

To a stirred suspension of the compound of preparation 26 (297 mg, 1.00 mmol) in dichloromethane (4 mL) at room temperature 1-adamantylamine (151 mg, 1.00 mmol) was added and the suspension stirred for 15 minutes. 2-Chloro-1,3-dimethylimidazolinium hexafluorophosphate (278 mg, 1.00 mmol) was added in one portion and the reaction stirred for 2 hours, after which time the reaction was homogeneous. The reaction was washed with water (5 mL), dried (magnesium sulphate) and the solvent removed in vacuo. The residue was purified by column chromatography on silica gel eluting with dichloromethane:methanol:880 ammonia (98:2:0.2 then 95:5:0.5) to furnish the title compound as a pale yellow foam, 325 mg.

$^1$H NMR (400 MHz, CD$_3$OD) δ 0.89 (3H, d), 1.36 (3H, d), 1.75 (6H, m), 1.98 (6H, s), 2.04 (6H, s), 2.40 (1H, dd), 2.74 (1H, m), 3.00 (1H, dd), 3.36 (2H, s), 4.00 (1H, q), 6.90 (1H, d), 6.98 (1H, s), 7.08 (1H, d), 7.19 (1H, t), 7.22 (1H, m), 7.38 (4H, m). LRMS: m/z electrospray 431 [M+H$^+$].

PREPARATION 28

N-Adamantan-1-yl-2-[3-(2-amino-propyl)-phenyl]-acetamide

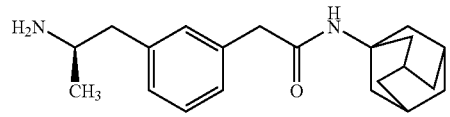

A solution the compound of preparation 27 (17.6 g, 36 mmol) and ammonium formate (22.7 g, 360 mmol) was heated to 70° C. in the presence of 20% palladium hydroxide-on-charcoal (Pd(OH)$_2$/C, 2.00 g). After 60 minutes further catalyst (500 mg) was added and the reaction heated for a further 4 hours. The reaction mixture was cooled to room temperature, filtered through Arbocel® and the filtrate concentrated in vacuo. The residue was partitioned between dichloromethane (300 mL) and 10% 880 ammonia in water (150 mL) and the organic phase separated dried (sodium sulfate) and reduced in vacuo. The residue was purified by column chromatography on silica gel eluting with dichloromethane:methanol:880 ammonia (95:5:0.5 then 90:10:1) to furnish the title compound as a white solid, 10.8 g.

$^1$H NMR (400 MHz, CD$_3$OD): δ 1.09 (3H, d), 1.68 (6H, m), 2.00 (6H, s), 2.03 (3H, s), 2.64 (2H, m), 3.14 (1H, q), 3.40 (2H, s), 7.14 (4H, m). LRMS (electrospray): m/z [M+H]$^+$ 327.

PREPARATION 29

N-Adamantan-1-yl-2-(3-{2-[2-(3,5-bis-benzyloxy-phenyl)-2-(tert-butyl-dimethyl-silanyloxy)-ethylamino]-propyl}-phenyl)-acetamide

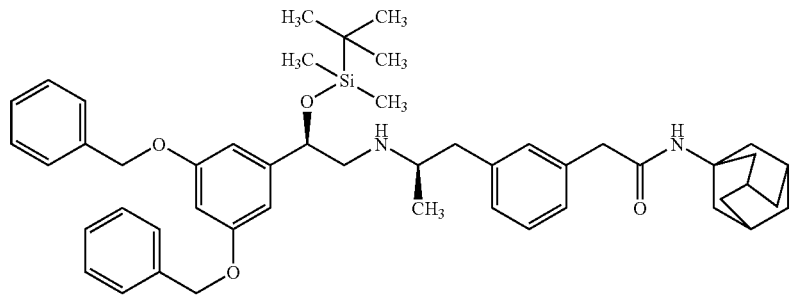

A solution of the compound of preparation 11 (263 mg, 0.50 mmol) and the compound of preparation 28 (326 mg, 1.00 mmol) in dichloromethane (1 mL) was heated to 90° C. and the solvent allowed to evaporate off. The resulting melt was heated at 90° C. for 1 day and then allowed to cool to room temperature. The residue was purified by column chromatography on silica gel eluting with dichloromethane:methanol:880 ammonia (98:2:0.2) to furnish the title compound as a clear oil, 168 mg.

$^1$H NMR (400 MHz, CD$_3$OD) δ −0.09 (3H, s), '0.02 (3H, s), 0.82 (9H, s), 1.03 (3H, d), 1.66 (6H, s), 1.99 (6H, s), 2.02 (3H, s), 2.59 (1H, m), 2.65 (2H, m), 2.85 (2H, m), 3.37 (2H, s), 4.86 (1H, m), 5.06 (4H, m), 6.54 (3H, m), 7.00 (14H, m). LRMS: m/z electrospray 773 [M+H$^+$].

PREPARATION 30

N-Adamantan-1-yl-2-(3-{2-[2-(tert-butyl-dimethyl-silanyloxy)-2-(3,5-dihydroxy-phenyl)-ethylamino]-propyl}-phenyl)-acetamide

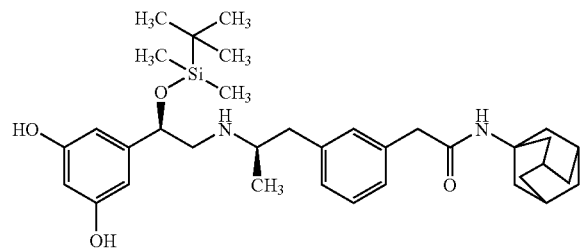

A solution the compound of preparation 29 (160 mg, 0.21 mmol) and ammonium formate (150 mg, 2.10 mmol) was heated to 70° C. in the presence of 20% palladium hydroxide-on-charcoal (Pd(OH)$_2$/C, 20 mg). After 3 hours the reaction mixture was cooled to room temperature, filtered through Arbocel® and the filtrate concentrated in vacuo. The residue was partitioned between ethyl acetate (10 mL) and 10% 880 ammonia in water (10 mL) and the organic phase separated dried. The aqueous was extracted with dichloromethane (2×50 mL) and the combined organics dried (sodium sulfate) and reduced in vacuo to furnish the title compound as a yellow foam, 160 mg.

$^1$H NMR (400 MHz, CD$_3$OD) δ −0.16 (3H, s), 0.01 (3H, s), 0.84 (9H, s), 1.03 (3H, d), 1.69 (6H, m), 2.01 (9H, m), 2.60 (3H, m), 2.91 (2H, m), 3.39 (2H, s), 4.60 (1H, m), 6.13 (1H, m), 6.20 (2H, m), 6.98 (1H, d), 7.05 (1H, s), 7.07 (1H, d), 7.18 (1H, t). LRMS: m/z electrospray 593 [M+H$^+$], 591 [M−H]$^-$

PREPARATION 31

(3-{2-[2-(3,5-Bis-benzyloxy-phenyl)-2-(tert-butyl-dimethyl-silanyloxy)-ethylamino]-2-methyl-propyl}-phenyl)-acetic acid methyl ester

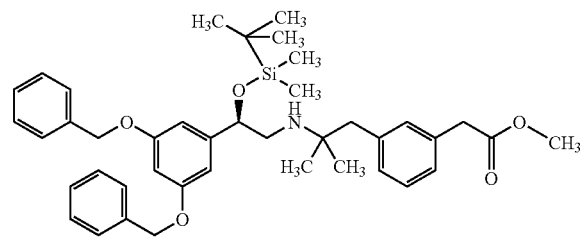

A solution of the compound of preparation 11 (5.30 g, 10.0 mmol) and the compound of preparation 5 (4.42 g, 20.0 mmol) were combined and heated to 92° C. under nitrogen. The resulting melt was heated at 92° C. for 24 hours and then allowed to cool to room temperature. The residue was purified by column chromatography on silica gel eluting with dichloromethane:methanol:880 ammonia (98:2:0.2) to furnish the title compound as a golden oil, 5.38 g.

$^1$H NMR (400 MHz, CD$_3$OD) δ −0.20 (3H, s), −0.03 (3H, s), 0.79 (9H, s), 1.01-1.03 (6H, d), 2.58-2.82 (4H, m), 3.59 (2H, s), 3.63 (3H, s), 4.62-4.66 (1H, m), 4.84 (4H, s), 6.76 (3H, s), 7.15-7.65 (14H, m). LRMS: m/z electrospray 668 [M+H$^+$].

PREPARATION 32

(3-{2-[2-(3,5-Bis-benzyloxy-phenyl)-2-(tert-butyl-dimethyl-silanyloxy)-ethylamino]-2-methyl-propyl}-phenyl)-acetic acid

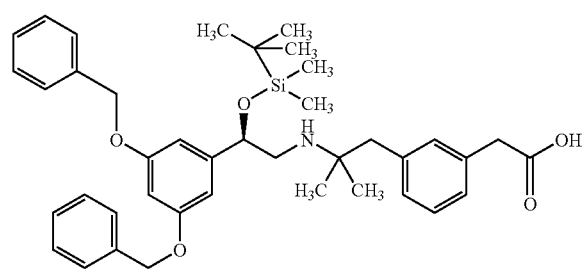

1M aqueous lithium hydroxide (8.80 mL, 8.80 mmol) was added in one portion to a stirred solution of the compound of preparation 31 (5.30 g, 7.95 mmol) in tetrahydrofuran (150 mL) at room temperature under nitrogen. The reaction was stirred at room temperature for 24 hours and 1M aqueous hydrochloric acid (8.80 mL, 8.80 mmol) was added in one portion. The majority of the solvent was removed in vacuo and the resulting mixture was partitioned between dichloromethane (200 mL) and water (200 mL). The organic layer was washed with brine (50 mL), dried (sodium sulfate) and the solvent removed in vacuo to afford the title compound as a colourless foam (5.16 g).

$^1$H NMR (400 MHz, CD$_3$OD) δ −0.17 (3H, s), 0.02 (3H, s), 0.82 (9H, s), 1.26 (6H, s), 2.84-2.96 (2H, q), 3.18-3.19 (2H, d), 3.53 (2H, s), 4.87-4.92 (1H, t), 5.10 (4H, s), 6.60-6.63 (3H, m), 7.03-7.43 (14H, m) LRMS: m/z electrospray 654 [M+H$^+$].

PREPARATION 33

(3-{2-[2-(tert-Butyl-dimethyl-silanyloxy)-2-(3,5-dihydroxy-phenyl)-ethylamino]-2-methyl-propyl}-phenyl)-acetic acid

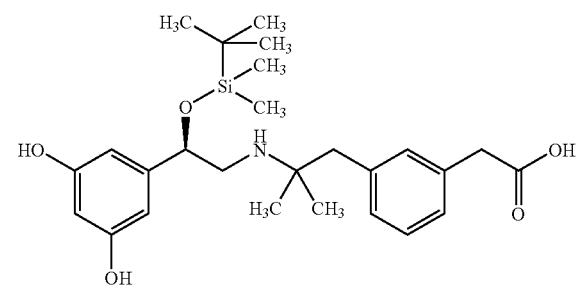

Palladium hydroxide (500 mg) was added in one portion to a stirred solution of the compound of preparation 32 (5.10 g, 7.81 mmol) and ammonium formate (5.00 g, 74.6 mmol) in ethanol (250 mL) at room temperature. The reaction was heated at 70° C. for 3 hours. Further palladium hydroxide was then added (250 mg) and the reaction heated at 70° C. for a further 1.5 hours and allowed to cool to room temperature under nitrogen overnight. The reaction was filtered through Arbocel® and the filtrate concentrated in vacuo. The residue was triturated with water (50 mL) and filtered to furnish the title compound as a white solid, 3.61 g.

$^1$H NMR (400 MHz, CD$_3$OD) δ −0.07 (3H, s), 0.03 (3H, s), 0.83 (9H, s), 1.34 (6H, s), 2.90-2.97 (2H, q), 3.18-3.19 (2H, s), 3.50-3.58 (2H, q), 4.85-4.95 (1H, m), 6.12 (1H, s), 6.35 (2H, s), 7.03-7.35 (4H, m). LRMS: m/z electrospray 474 [M+H$^+$].

PREPARATION 34

2-(3-{2-[2-(tert-Butyl-dimethyl-silanyloxy)-2-(3,5-dihydroxy-phenyl)-ethylamino]-2-methyl-propyl}-phenyl)-N-(3,4-dichloro-benzyl)-acetamide

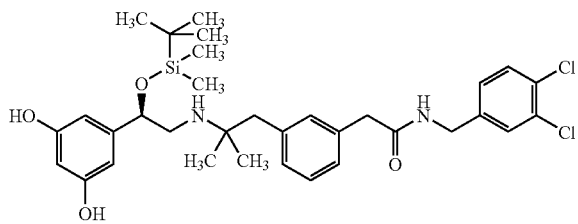

3,4-Dichlorobenzylamine (53 mg, 0.301 mmol), hydroxybenzotriazole (39 mg, 0.289 mmol) and 1-(3-dimethylaminopropyl)-3-ethylcarbodiimide hydrochloride (57 mg, 0.297 mmol) were added to a stirred solution of the compound of preparation 33 (142 mg, 0.300 mmol) in N,N-dimethylformamide (2 mL) at room temperature under nitrogen. The reaction was stirred for 18 hours and the solvent removed in vacuo, the residue was then was partitioned between dichloromethane (50 mL) and saturated aqueous sodium hydrogen carbonate (50 mL). The organic layer was dried (sodium sulfate) and the solvent removed in vacuo and purified by column chromatography on silica gel eluting with dichloromethane:methanol:880 ammonia (95:5:0.5) to furnish the title compound as a cream foam, 125 mg.

$^1$H NMR (400 MHz, CD$_3$OD) δ −0.16 (3H, s), 0.00 (3H, s), 0.82 (9H, s), 1.01-1.03 (6H, d), 2.60-2.86 (4H, m), 3.52 (2H, s), 4.31 (2H, s), 4.78-4.81 (1H, m), 6.18 (1H, s), 6.29 (2H, s), 7.02-7.24 (5H, m), 7.36-7.42 (2H, m). LRMS: m/z electrospray 631 [M+H$^+$].

PREPARATION 35

(3-{2-[2-(3,5-Bis-benzyloxy-phenyl)-2-(tert-butyl-dimethyl-silanyloxy)-ethylamino]-propyl}-phenyl)-acetic acid methyl ester

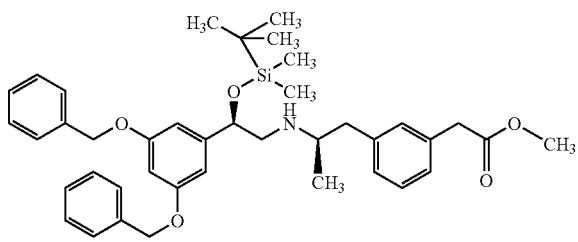

A solution of the compound of preparation 11 (5.00 g, 9.45 mmol) and the compound of preparation 22 (3.92 g, 18.9 mmol) in dichloromethane (50 mL) was heated to 95° C. and the solvent allowed to evaporate off. The resulting melt was heated at 95° C. for 24 hours and then allowed to cool to room temperature. Diethylether (50 mL) was added and the mixture was stirred for 5 minutes. The ether layer was separated from the gum and then the gum was extracted twice more with diethylether (2×50 mL). The ether extracts were combined and the solvent was removed in vacuo. The residue was purified by column chromatography on silica gel eluting with dichloromethane:methanol:880 ammonia (100:0:0 to 95:5: 0.5) to furnish the title compound as a pale yellow gum, 4.50 g.

$^1$H NMR (400 MHz, CD$_3$OD) δ −0.20 (3H, s), −0.05 (3H, s), 0.81 (9H, s), 1.01-1.03 (3H, d), 2.60 (3H, m), 2.86 (2H, m), 3.55 (2H, s), 3.63 (3H, s), 4.66 (1H, m), 4.85 (4H, m), 6.70 (3H, m), 6.73 (1H, m), 6.98 (2H, m), 7.06 (1H, m), 7.17 (1H, m), 7.10 (2H, m), 7:11-7.22 (7H, m). LRMS: m/z electrospray 654 [M+H$^+$].

PREPARATION 36

3-{2-[2-(tert-Butyl-dimethyl-silanyloxy)-2-(3,5-dihydroxy-phenyl)-ethylamino]-2-methyl-propyl}-N-[2-(3-fluoro-phenyl)-ethyl]-benzamide

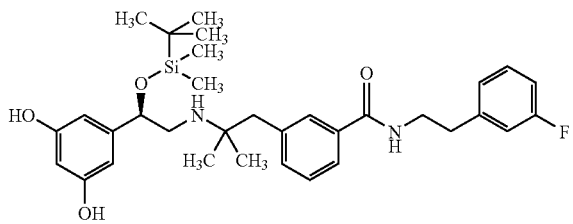

2-Fluorophenylethylamine (95 mg, 0.680 mmol), hydroxybenzotriazole (100 mg, 0.740 mmol), triethylamine (0.10 mL, 0.720 mmol) and 1-(3-dimethylaminopropyl)-3-ethylcarbodiimide hydrochloride (79 mg, 0.410 mmol) were added to a stirred solution of the compound of preparation 14 (151 mg, 0.330 mmol) in N,N-dimethylformamide (1 mL) at room temperature under nitrogen. The reaction was stirred for 18 hours and the solvent removed in vacuo and purified by column chromatography on silica gel eluting with dichloromethane:methanol:880 ammonia (100:0:0 to 95:5:0.5 to 90:10:1) to furnish the title compound as a cream foam, 132 mg.

$^1$H NMR (400 MHz, CD$_3$OD) δ −0.16 (3H, s), −0.02 (3H, s), 0.78 (9H, s), 1.12 (6H, d), 2.65-2.95 (6H, m), 3.61 (2H, s), 4.64 (1H, s), 6.18 (1H, s), 6.29 (2H, s), 6.93 (1H, m), 7.02 (1H, m), 7.06 (1H, m), 7.20-7.39 (3H, m), 7.64 (2H, m). LRMS: m/z electrospray 581 [M+H$^+$].

Preparation 37 to 43 were prepared from compounds of preparation 14 and the appropriate amine using the method disclosed for preparation 36:

Preparations 37 to 43

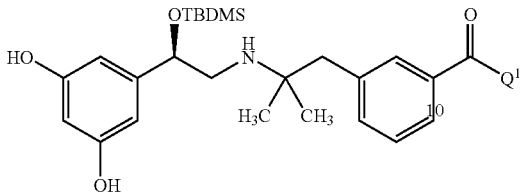

| No | Q¹ | Data |
|----|----|------|
| 37 | 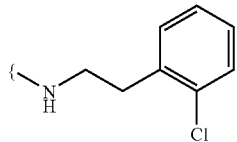 | The compound was isolated as a brown oil<br>$^1$H NMR (400 MHz, CD$_3$OD) δ −0.16 (3H, s), −0.02 (3H, s), 0.78 (9H, s), 1.08 (6H, d), 2.60-2.84 (4H, m), 3.08 (2H, m), 3.64 (2H, m), 4.61 (1H, m), 6.18 (1H, s), 6.29 (2H, s), 7.13-7.39 (6H, m), 7.63 (2H, m).<br>LRMS: m/z electrospray 597 [M + H$^+$]. |
| 38 | 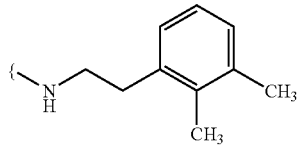 | The compound was isolated as a white foam.<br>$^1$H NMR (400 MHz, CD$_3$OD) δ −0.16 (3H, s), −0.02 (3H, s), 0.80 (9H, s), 1.08 (6H, d), 2.27 (3H, s), 2.29 (3H, s), 2.60-2.89 (4H, m), 2.96 (2H, m), 3.55 (2H, m), 4.61 (1H, m), 6.18 (1H, s), 6.29 (2H, s), 6.93-7.03 (3H, m), 7.30-7.38 (2H, m), 7.65 (2H, m).<br>LRMS: m/z electrospray 591 [M + H$^+$]. |
| 39 | 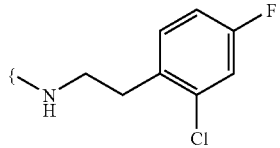 | The compound was isolated as an orange foam.<br>$^1$H NMR (400 MHz, CD$_3$OD) δ −0.16 (3H, s), −0.02 (3H, s), 0.80 (9H, s), 1.10 (6H, d), 2.60-2.89 (4H, m), 3.05 (2H, m), 3.62 (2H, m), 4.61 (1H, m), 6.18 (1H, s), 6.29 (2H, s), 7.00 (1H, m), 7.19 (1H, m), 7.27-7.38 (3H, m), 7.64 (2H, m).<br>LRMS: m/z electrospray 615 [M + H$^+$]. |
| 40 | 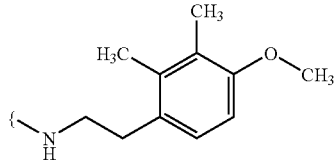 | The compound was isolated as a pale orange solid.<br>$^1$H NMR (400 MHz, CD$_3$OD) δ −0.16 (3H, s), −0.02 (3H, s), 0.80 (9H, s), 1.10 (6H, d), 2.14 (3H, s), 2.27 (3H, s), 2.60-2.93 (6H, m), 3.49 (2H, m), 3.77 (3H, s), 4.61 (1H, m), 6.18 (1H, s), 6.29 (2H, s), 6.69 (1H, m), 6.98 (1H, m), 7.30-7.39 (2H, m), 7.65 (2H, m).<br>LRMS: m/z electrospray 621 [M + H$^+$]. |
| 41 | 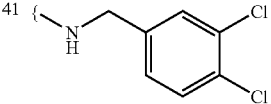 | The compound was isolated as a white solid.<br>$^1$H NMR (400 MHz, CD$_3$OD) δ −0.16 (3H, s), −0.02 (3H, s), 0.80 (9H, s), 1.13 (3H, s), 1.16 (3H, s), 2.68-2.72 (1H, m), 2.78-2.81 (1H, m), 2.85-2.90 (2H, m), 4.59 (2H, s), 4.62-4.65 (1H, m), 6.21 (1H, m), 6.33 (1H, m), 6.34 (1H, m), 7.33-7.35 (1H, m), 7.39-7.46 (2H, m), 7.50-7.53 (1H, m), 7.56 (1 H, m), 7.78 (2H, m).<br>LRMS: m/zelectrospray 619 [M + H$^+$]. |
| 42 | 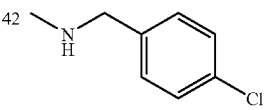 | The compound was isolated as a white solid.<br>$^1$H NMR (400 MHz, CD$_3$OD) δ −0.12 (3H, s), −0.02 (3H, s), 0.80 (9H, s), 1.13 (3H, s), 1.16 (3H, s), 2.68-2.72 (1H, m), 2.78-2.88 (3H, m), 4.59 (2H, s), 4.62-4.65 (1H, m), 6.21 (1H, m), 6.34 (2H, m), 7.35-7.45 (6H, m), 7.77 (2H, m).<br>LRMS: m/z electrospray 583 [M + H$^+$]. |
| 43 | 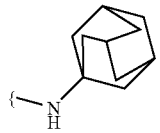 | The compound was isolated as a white solid.<br>$^1$H NMR (400 MHz, CD$_3$OD) δ −0.09 (3H, s), −0.02 (3H, s), 0.85 (9H, s), 1.13 (3H, s), 1.16 (3H, s), 1.81 (6H, s), 2.15 (3H, s), 2.21 (6H, m), 2.68-2.90 (4H, m), 4.64-4.67 (1H, s), 6.21 (1H, m), 6.33 (1H, s), 6.34 (1H, s), 7.30-7.40 (2H, m), 7.64 (2H, m).<br>LRMS: m/z electrospray 594 [M + H$^+$]. |

PREPARATION 44

(3-{2-[2-(3,5-Bis-benzyloxy-phenyl)-2-(tert-butyl-dimethyl-silanyloxy)-ethylamino]-propyl}-phenyl)-acetic acid

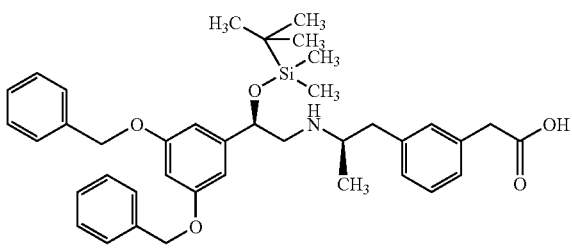

1M aqueous lithium hydroxide (16.0 mL, 16.0 mmol) was added in one portion to a stirred solution of the compound of preparation 35 (4.75 g, 7.26 mmol) in tetrahydrofuran (20 mL) at room temperature. The reaction was stirred at room temperature for 24 hours and 1M aqueous hydrochloric acid was added until pH reached 1-2. Extracted with dichloromethane (1×200 mL then 2×50 mL) and the combined organic layers washed with brine (20 mL), dried (magnesium sulphate) and the solvent removed in vacuo to furnish the title compound hydrochloride salt as an off-white foam, 4.80 g.

$^1$H NMR (400 MHz, CD$_3$OD) δ −0.12 (3H, s), 0.06 (3H, s), 0.86 (9H, s), 1.23 (3H, d), 2.77 (1H, m), 3.03 (1H, m), 3.23 (1H, m), 3.45-3.60 (3H, m), 5.01 (1H, m), 5.10 (4H, s), 6.64 (2H, m), 6.68 (1H, m), 7.10 (1H, m), 7.15 (1H, s), 7.23 (1H, m), 7.27-7.43 (11H, m). LRMS: m/z APCl 640 [M+H$^+$].

PREPARATION 45

(3-{2-[2-(tert-Butyl-dimethyl-silanyloxy)-2-(3,5-dihydroxy-phenyl)-ethylamino]-propyl}-phenyl)-acetic acid

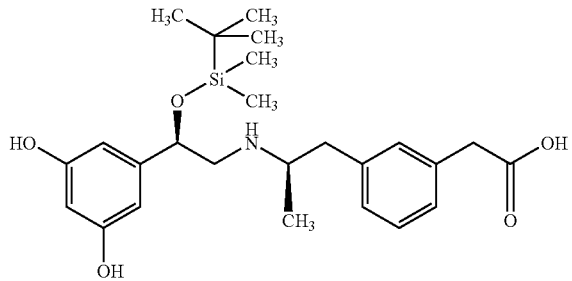

Palladium hydroxide (350 mg) was added in one portion to a stirred solution of the compound of preparation 44 (3.50 g, 5.48 mmol) and ammonium formate (1.80 g, 39.1 mmol) in ethanol (250 mL) at room temperature. The reaction was heated under reflux for 45 minutes and allowed to cool to room temperature. The reaction was filtered through Arbocel® and the filtrate concentrated in vacuo to furnish the title compound as a pale yellow solid, 2.30 g.

$^1$H NMR (400 MHz, CD$_3$OD) δ −0.06 (3H, s), 0.06 (3H, s), 0.86 (9H, s), 1.25 (3H, d), 2.81 (1H, m), 2.96 (1H, m), 3.15 (1H, m), 3.25 (1H, m), 3.43-3.55 (3H, m), 4.89 (1H, m), 6.24 (1H, m), 6.33 (2H, m), 7.06 (1H, m), 7.17 (1H, s), 7.19-7.28 (2H, m). LRMS: m/z APCl 460 [M+H$^+$].

Preparations 46 to 48, 55 to 65 and 73 to 76 were prepared from preparation 33 and the appropriate amine, using the method of preparation 34. These compounds are of generic formula

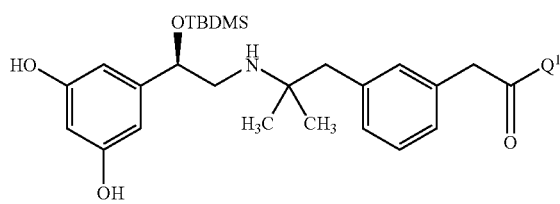

and are listed in the table below.

Preparations 49 to 54, 66 to 72 and 77 to 87 were prepared from preparation 45 and the appropriate amine, using the method of preparation 34. These compounds are of generic formula

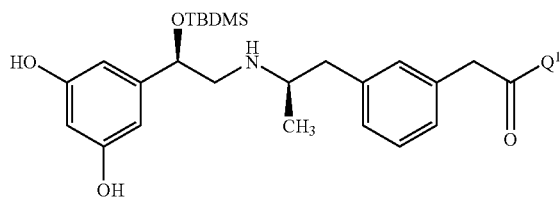

and are listed in the table below.

| No | Q$^1$ | Data |
|---|---|---|
| 46 | <img 4-Cl-benzyl-NH> | The compound was isolated as a white solid.<br>$^1$H NMR (400 MHz, CD$_3$OD) δ −0.14 (3H, s), 0.00 (3H, s), 0.80 (9H, s), 1.01-1.03 (6H, d), 2.62-2.84 (4H, m), 3.53 (2H, s), 4.34 (2H, s), 4.58-4.62 (1H, m), 6.18 (1H, s), 6.26 (2H, s), 7.01-7.27 (8H, m).<br>LRMS: m/z electrospray 597 [M + H$^+$]. |

-continued

| No | Q¹ | Data |
|---|---|---|
| 47 | 4-OCF₃-benzyl-NH- | The compound was isolated as a white solid.<br>¹H NMR (400 MHz, CD₃OD) δ −0.12 (3H, s), 0.00 (3H, s), 0.82 (9H, s), 1.01-1.03 (6H, d), 2.60-2.84 (4H, m), 3.54 (2H, s), 4.37 (2H, s), 4.58-4.62 (1H, m), 6.17 (1H, s), 6.28 (2H, s), 7.03 (1H, d), 7.08 (1H, s), 7.15-7.23 (4H, m), 7.32 (2H, d).<br>LRMS: m/z electrospray 647 [M + H⁺]. |
| 48 | (pyridin-2-yl)methyl-NH- | The compound was isolated as a white solid.<br>¹H NMR (400 MHz, CD₃OD) δ −0.13 (3H, s), 0.00 (3H, s), 0.82 (9H, s), 1.05-1.06 (6H, d), 2.65-2.83 (4H, m), 3.58 (2H, s), 4.47 (2H, s), 4.58-4.63 (1H, m), 6.17 (1H, s), 6.29 (2H, s), 7.06 (1H, d), 7.13 (1H, s), 7.18-7.30 (4H, m), 7.71-7.75 (1H, t), 8.44-8.45 (1H, d).<br>LRMS: m/z electrospray 564 [M + H⁺]. |
| 49 | 3,4-dichlorobenzyl-NH- | The compound was isolated as a white solid.<br>¹H NMR (400 MHz, CD₃OD) δ −0.18 (3H, s), 0.00 (3H, s), 0.81 (9H, s), 1.02 (3H, d), 2.60 (3H, m), 2.83 (2H, m), 3.51 (2H, s), 4.32 (2H, s), 4.58 (1H, m), 6.17 (1H, s), 6.22 (2H, d), 7.20 (6H, m), 7.40 (2H, m).<br>LRMS: m/z APCI 617 [M + H⁺], 615 [M − H⁻]. |
| 50 | benzyl-NH- | ¹H NMR (400 MHz, CD₃OD) δ −0.15 (3H, s), 0.01 (3H, s), 0.85 (9H, s), 1.03 (3H, d), 2.58 (1H, m), 2.65 (2H, m), 2.83 (2H, m), 3.53 (2H, s), 4.36 (2H, s), 4.59 (1H, m), 6.16 (1H, m), 6.22 (2H, s), 6.98 (1H, m), 7.06 (1H, s), 7.13 (1H, m), 7.20 (6H, m).<br>LRMS: m/z APCI 549 [M + H⁺], 547 [M − H⁻]. |
| 51 | cyclohexylmethyl-NH- | The compound was isolated as a white foam.<br>¹H NMR (400 MHz, CD₃OD) δ −0.15 (3H, s), 0.01 (3H, s), 0.85 (11H, m), 1.06 (3H, d), 1.15 (3H, m), 1.42 (1H, m), 1.68 (5H, m), 2.55 (1H, m), 2.65 (2H, m), 2.88 (2H, m), 3.02 (2H, d), 3.46 (2H, s), 4.60 (1H, m), 6.15 (1H, m), 6.22 (2H, s), 6.98 (1H, m), 7.07 (1H, s), 7.10 (1H, m), 7.18 (1H, m).<br>LRMS: m/z APCI 555 [M + H⁺], 553 [M − H⁻]. |
| 52 | 1,2,3,4-tetrahydroisoquinolin-2-yl | The compound was isolated as a pale yellow foam.<br>¹H NMR (400 MHz, CD₃OD) δ −0.15 (3H, s), 0.01 (3H, s), 0.85 (9H, s), 1.03 (3H, m), 2.58 (7H, m), 3.73 (1H, m), 3.82 (3H, m), 4.57 (1H, m), 4.68 (2H, m), 6.16 (1H, m), 6.23 (2H, m), 7.10 (8H, m).<br>LRMS: m/z APCI 575 [M + H⁺], 573 [M − H⁻]. |
| 53 | N-methyl-N-benzyl- | The compound was isolated as a white foam.<br>¹H NMR (400 MHz, CD₃OD) δ −0.15 (3H, s), 0.01 (3H, s), 0.85 (9H, s), 1.02 (3H, m), 2.58 (3H, m), 2.83 (5H, m), 3.77 (2H, m), 4.58 (3H, m), 6.15 (1H, m), 6.22 (2H, s), 6.98 (2H, m), 7.07 (2H, m), 7.20 (5H, m).<br>LRMS: m/z APCI 563 [M + H⁺], 561 [M − H⁻]. |
| 54 | 2-hydroxybenzyl-NH- | The compound was isolated as a white foam.<br>¹H NMR (400 MHz, CD₃OD) δ −0.15 (3H, s), 0.01 (3H, s), 0.86 (9H, s), 1.03 (3H, d), 2.55 (1H, m), 2.64 (2H, m), 2.85 (2H, m), 3.53 (2H, s), 4.35 (2H, s), 4.59 (1H, m), 6.15 (1H, m), 6.22 (2H, s), 6.76 (2H, m), 6.98 (1H, m), 7.06 (4H, m), 7.18 (1H, m).<br>LRMS: m/z APCI 565 [M + H⁺], 563 [M − H⁻]. |
| 55 | 4-cyanobenzyl-NH- | The compound was isolated as a white solid.<br>¹H NMR (400 MHz, CD₃OD) δ −0.08 (3H, s), 0.04 (3H, s), 0.87 (9H, s), 1.10 (3H, s), 1.12 (3H, s), 2.65 (3H, m), 2.90 (1H, m), 3.59 (2H, s), 4.47 (2H, s), 4.64 (1H, m), 6.22 (1H, m), 6.34 (2H, s), 7.09 (1H, m), 7.15 (1H, s), 7.25 (2H, m), 7.42 (2H, d), 7.67 (2H, d).<br>LRMS: m/z electrospray 588 [M + H⁺], 586 [M − H⁻]. |
| 56 | 2,4-dichlorobenzyl-NH- | The compound was isolated as a white solid.<br>¹H NMR (400 MHz, CD₃OD) δ −0.08 (3H, s), 0.04 (3H, s), 0.87 (9H, s), 1.09 (3H, s), 1.11 (3H, s), 2.80 (4H, m), 3.59 (2H, s), 4.46 (2H, s), 4.64 (1H, m), 6.22 (1H, m), 6.34 (2H, s), 7.10 (1H, d), 7.14 (1H, s), 7.22 (1H, m), 7.27 (3H, m), 7.48 (1H, s).<br>LRMS: m/z electrospray 633 [M + H⁺], 629 [M − H⁻]. |

-continued

| No | Q¹ | Data |
|---|---|---|
| 57 | benzylamino- | The compound was isolated as a white foam.<br>$^1$H NMR (400 MHz, CD$_3$OD) δ −0.10 (3H, s), 0.05 (3H, s), 0.83 (9H, s), 1.06 (3H, s), 1.08 (3H, s), 2.65 (3H, m), 2.83 (1H, m), 3.53 (2H, s), 4.37 (2H, s), 4.59 (1H, m), 6.18 (1H, s), 6.28 (2H, s), 7.03 (1H, d), 7.11 (1H, s), 7.16 (1H, m), 7.27 (6H, m).<br>LRMS: m/z electrospray 563 [M + H⁺]. |
| 58 | (2-chlorobenzyl)amino- | The compound was isolated as a white foam.<br>$^1$H NMR (400 MHz, CD$_3$OD) δ −0.10 (3H, s), 0.01 (3H, s), 0.84 (9H, s), 1.06 (3H, s), 1.08 (3H, s), 2.68 (3H, m), 2.84 (1H, m), 3.56 (2H, s), 4.43 (2H, s), 4.59 (1H, m), 6.18 (1H, m), 6.28 (2H, s), 7.07 (1H, d), 7.12 (1H, s), 7.20 (5H, m), 7.37 (1H, d).<br>LRMS: m/z electrospray 597 [M + H⁺]. |
| 59 | (3-methoxybenzyl)amino- | The compound was isolated as a colourless oil.<br>LRMS: m/z electrospray 593 [M + H⁺]. |
| 60 | (cyclohexylmethyl)amino- | The compound was isolated as a white foam.<br>$^1$H NMR (400 MHz, CD$_3$OD) δ −0.08 (3H, s), 0.02 (3H, s), 0.84 (9H, s), 0.90 (2H, m), 1.06 (3H, s), 1.08 (3H, s), 1.18 (3H, m), 1.40 (1H, m), 1.68 (5H, m), 2.68 (3H, m), 2.83 (1H, m), 3.02 (2H, d), 3.47 (2H, s), 4.60 (1H, m), 6.17 (1H, t), 6.27 (2H, s), 7.04 (1H, d), 7.12 (1H, s), 7.15 (1H, d), 7.21 (1H, t).<br>LRMS: m/z electrospray 569 [M + H⁺]. |
| 61 | (2-phenylethyl)amino- | The compound was isolated as a white foam.<br>$^1$H NMR (400 MHz, CD$_3$OD) δ −0.08 (3H, s), 0.01 (3H, s), 0.82 (9H, s), 1.08 (3H, s), 1.08 (3H, s), 2.68 (6H, m), 3.41 (2H, t), 3.44 (2H, s), 4.60 (1H, m), 6.17 (1H, m), 6.27 (2H, s), 7.14 (9H, m).<br>LRMS: m/z electrospray 577 [M + H⁺]. |
| 62 | [2-(4-chlorophenyl)ethyl]amino- | The compound was isolated as a white foam.<br>$^1$H NMR (400 MHz, CD$_3$OD) δ −0.08 (3H, s), 0.01 (3H, s), 0.82 (9H, s), 1.07 (3H, s), 1.08 (3H, s), 2.67 (3H, m), 2.73 (2H, m), 2.83 (1H, m), 3.42 (4H, m), 4.60 (1H, m), 6.08 (1H, s), 6.28 (2H, s), 7.05 (2H, d), 7.11 (3H, m), 7.20 (3H, m).<br>LRMS: m/z electrospray 611 [M + H⁺]. |
| 63 | [2-(4-biphenyl)ethyl]amino- | The compound was isolated as a white foam.<br>$^1$H NMR (400 MHz, CD$_3$OD) δ −0.08 (3H, s), 0.01 (3H, s), 0.81 (9H, s), 1.04 (3H, s), 1.04 (3H, s), 2.64 (3H, m), 2.80 (3H, m), 2.83 (1H, m), 3.42 (4H, m), 4.60 (1H, m), 6.17 (1H, m), 6.28 (2H, s), 7.03 (2H, m), 7.11 (1H, d), 7.20 (3H, m), 7.28 (1H, m), 7.41 (2H, t), 7.48 (1H, d), 7.57 (3H, m).<br>LRMS: m/z electrospray 653 [M + H⁺]. |
| 64 | [3-(4-hydroxyphenyl)benzyl]amino- | The compound was isolated as a white foam.<br>$^1$NMR (400 MHz, CD$_3$OD) δ −0.08 (3H, s), 0.01 (3H, s), 0.82 (9H, s), 1.01 (3H, s), 1.02 (3H, s), 2.60 (3H, m), 2.78 (1H, m), 3.56 (2H, s), 4.42 (2H, s), 4.58 (1H, m), 6.17 (1H, s), 6.27 (2H, s), 6.84 )2H, m), 7.04 (1H, d), 7.09 (1H, s), 7.20 (3H, m), 7.17 (1H, d), 7.30 (7H, m).<br>LRMS: m/z electrospray 655 [M + H⁺], 653 [M − H⁻]. |
| 65 | cycloheptylamino- | The compound was isolated as a white foam.<br>$^1$H NMR (400 MHz, CD$_3$OD) δ −0.08 (3H, s), 0.01 (3H, s), 0.83 (9H, s), 1.07 (3H, s), 1.07 (3H, s), 1.55 (9H, m), 1.84 (2H, m), 2.68 (3H, m), 2.86 (1H, m), 3.43 (2H, s), 3.80 (1H, m), 4.60 (1H, m), 6.17 (1H, m), 6.28 (2H, s), 7.04 (1H, d), 7.09 (1H, s), 7.16 (1H, d), 7.22 (1H, t).<br>LRMS: m/z electrospray 570 [M + H⁺], 568 [M − H⁻]. |

-continued

| No | Q¹ | Data |
|---|---|---|
| 66 | –NH–CH₂CH₂–phenyl | The compound was isolated as a white foam.<br>¹H NMR (400 MHz, CD₃OD) δ −0.14 (3H, s), 0.01 (3H, s), 0.85 (9H, s), 1.05 (3H, d), 2.55 (7H, m), 3.42 (4H, m), 4.59 (1H, m), 6.13 (1H, m), 6.23 (2H, s), 7.18 (9H, m).<br>LRMS: m/z APCI 563 [M + H⁺]. |
| 67 | –NH–CH₂–(2-SMe-phenyl) | ¹H NMR (400 MHz, CD₃OD) δ −0.14 (3H, s), 0.01 (3H, s), 0.85 (9H, s), 1.03 (3H, d), 2.43 (3H, s), 2.60 (5H, m), 3.52 (2H, s), 4.04 (2H, s), 4.59 (1H, m), 6.14 (1H, m), 6.24 (2H, s), 7.18 (8H, m).<br>LRMS: m/z APCI 595 [M + H⁺]. |
| 68 | –NH–CH₂–(2,6-diCl-phenyl) | The compound was isolated as a white foam.<br>¹H NMR (400 MHz, CD₃OD) δ −0.14 (3H, s), 0.01 (3H, s), 0.85 (9H, s), 1.03 (3H, d), 2.52 (1H, m), 2.66 (2H, m), 2.85 (2H, m), 3.48 (2H, s), 4.60 (1H, m), 4.66 (2H, s), 6.14 (1H, m), 6.24 (2H, s), 7.20 (7H, m).<br>LRMS: m/z APCI 615 [M + H⁺]. |
| 69 | –NH–(2-indanyl) | The compound was isolated as a white foam.<br>¹H NMR (400 MHz, CD₃OD) δ −0.14 (3H, s), 0.01 (3H, s), 0.85 (9H, s), 1.04 (3H, d), 2.58 (3H, m), 2.85 (4H, m), 3.25 (2H, m), 3.48 (2H, s), 4.60 (2H, m), 6.15 (1H, m), 6.23 (2H, s), 7.10 (8H, m).<br>LRMS: m/z APCI 575 [M + H⁺]. |
| 70 | –NH–CH₂–(2-F,6-Cl-phenyl) | The compound was isolated as a white foam.<br>¹H NMR (400 MHz, CD₃OD) δ −0.14 (3H, s), 0.01 (3H, s), 0.85 (9H, s), 1.03 (3H, d), 2.52 (1H, m), 2.62 (2H, m), 2.85 (2H, m), 3.48 (2H, s), 4.52 (2H, m), 4.60 (1H, m), 6.18 (1H, s), 6.24 (2H, s), 7.20 (7H, m). |
| 71 | –NH–CH₂–(2-Me,6-Cl-phenyl) | The compound was isolated as a white foam.<br>¹H NMR (400 MHz, CD₃OD) δ −0.14 (3H, s), 0.01 (3H, s), 0.84 (9H, s), 1.03 (3H, d), 2.18 (3H, s), 2.52 (1H, m), 2.62 (2H, m), 2.85 (2H, m), 3.43 (2H, s), 4.52 (2H, m), 4.60 (1H, m), 6.18 (1H, s), 6.24 (2H, s), 7.20 (7H, m).<br>LRMS: m/z APCI 597 [M + H⁺], 595 [M − H⁻]. |
| 72 | –NH–CH₂–(4-Cl-phenyl) | The compound was isolated as a white solid.<br>¹H NMR (400 MHz, CD₃OD) δ −0.18 (3H, s), 0.01 (3H, s), 0.84 (9H, s), 1.03 (3H, d), 2.60 (3H, m), 2.85 (2H, m), 3.48 (2H, s), 4.33 (2H, s), 4.57 (1H, m), 6.18 (1H, s), 6.24 (2H, s), 7.20 (8H, m).<br>LRMS: m/z APCI 583 [M + H⁺], 581 [M − H⁻]. |
| 73 | –NH–CH₂–(2,5-diCl-phenyl) | The compound was isolated as a white solid.<br>¹H NMR (400 MHz, CD₃OD) δ −0.08 (3H, s), 0.05 (3H, s), 0.87 (9H, s), 1.10 (3H, s), 1.12 (3H, s), 2.78 (4H, m), 3.61 (2H, s), 4.47 (2H, s), 4.65 (1H, m), 6.22 (1H, m), 6.34 (2H, s), 7.11 (1H, d), 7.17 (1H, s), 7.28 (4H, m), 7.40 (1H, d).<br>LRMS: m/z electrospray 631 [M + H⁺], 631 [M − H⁻]. |
| 74 | –NH–CH₂–(3,5-diCl-phenyl) | The compound was isolated as a white solid.<br>¹H NMR (400 MHz, CD₃OD) δ −0.08 (3H, s), 0.04 (3H, s), 0.87 (9H, s), 1.09 (3H, s), 1.11 (3H, s), 2.74 (3H, m), 2.88 (1H, m), 3.58 (2H, s), 4.37 (2H, s), 4.65 (1H, m), 6.22 (1H, m), 6.34 (2H, s), 7.11 (1H, m), 7.14 (1H, s), 7.21 (3H, m), 7.28 (1H, m), 7.33 (1H, t).<br>LRMS: m/z electrospray 631 [M + H⁺], 629 [M − H⁻]. |

| No | Q¹ | Data |
|---|---|---|
| 75 | 2,6-dichlorobenzyl-NH- | The compound was isolated as a white solid.<br>¹H NMR (400 MHz, CD₃OD) δ −0.08 (3H, s), 0.04 (3H, s), 0.87 (9H, s), 1.08 (3H, s), 1.10 (3H, s), 2.74 (3H, m), 2.88 (1H, m), 3.53 (2H, s), 4.64 (1H, m), 4.71 (2H, s), 6.22 (1H, m), 6.34 (2H, s), 7.07 (1H, d), 7.13 (1H, s), 7.19 (1H, m), 7.25 (1H, m), 7.33 (1H, m), 7.43 (2H, d).<br>LRMS: m/z electrospray 634 [M + H⁺], 630 [M − H⁻]. |
| 76 | biphenyl-2-ylmethyl-NH- | The compound was isolated as a white solid.<br>¹H NMR (400 MHz, CD₃OD) δ −0.09 (3H, s), 0.04 (3H, s), 0.86 (9H, s), 1.09 (3H, s), 1.11 (3H, s), 2.74 (4H, m), 3.51 (2H, s), 4.32 (2H, s), 4.64 (1H, m), 6.22 (1H, m), 6.34 (2H, s), 7.11 (2H, m), 7.18 (1H, d), 7.30 (10H, m).<br>LRMS: m/z electrospray 639 [M + H⁺], 637 [M − H⁻]. |
| 77 | 2-chlorobenzyl-NH- | The compound was isolated as a white foam.<br>¹H NMR (400 MHz, CD₃OD) δ −0.15 (3H, s), 0.01 (3H, s), 0.85 (9H, s), 1.03 (3H, d), 2.64 (5H, m), 3.54 (2H, s), 4.45 (2H, s), 4.59 (1H, m), 6.15 (1H, m), 6.23 (2H, s), 6.99 (1H, m), 7.08 (1H, m), 7.20 (6H, m).<br>LRMS: m/z APCI 583 [M + H⁺]. |
| 78 | 3-methoxybenzyl-NH- | The compound was isolated as a white foam.<br>¹H NMR (400 MHz, CD₃OD) δ −0.13 (3H, s), 0.01 (3H, s), 0.85 (9H, s), 1.03 (3H, d), 2.64 (5H, m), 3.51 (2H, s), 3.70 (3H, s), 4.33 (2H, s), 4.59 (1H, m), 6.15 (1H, m), 6.23 (2H, s), 6.80 (3H, m), 6.99 (1H, m), 7.06 (1H, m), 7.18 (3H, m).<br>LRMS: m/z APCI 579 [M + H⁺]. |
| 79 | 3-trifluoromethylbenzyl-NH- | The compound was isolated as a pale brown foam.<br>¹H NMR (400 MHz, CD₃OD) δ −0.15 (3H, s), 0.02 (3H, s), 0.85 (9H, s), 1.03 (3H, d), 2.64 (3H, m), 2.86 (2H, m), 3.53 (2H, s), 4.43 (2H, s), 4.59 (1H, m), 6.14 (1H, m), 6.23 (2H, s), 6.91 (1H, m), 7.06 (1H, s), 7.15 (1H, m), 7.19 (1H, m), 7.48 (4H, m).<br>LRMS: m/z APCI 617 [M + H⁺], 615 [M − H⁻]. |
| 80 | 3,4-difluorobenzyl-NH- | The compound was isolated as a pale brown foam.<br>¹H NMR (400 MHz, CD₃OD) δ −0.15 (3H, s), 0.01 (3H, s), 0.85 (9H, s), 1.03 (3H, d), 2.60 (3H, m), 2.86 (2H, m), 3.52 (2H, s), 4.33 (2H, s), 4.58 (1H, m), 6.14 (1H, m), 6.23 (2H, s), 7.18 (7H, m).<br>LRMS: m/z APCI 585 [M + H⁺], 583 [M − H⁻]. |
| 81 | 2-methoxybenzyl-NH- | The compound was isolated as a pale brown foam.<br>¹H NMR (400 MHz, CD₃OD) δ −0.15 (3H, s), 0.01 (3H, s), 0.85 (9H, s), 1.02 (3H, d), 2.53 (1H, m), 2.64 (2H, m), 2.84 (2H, m), 3.50 (2H, s), 3.78 (3H, s), 4.36 (2H, s), 4.59 (1H, m), 6.14 (1H, m), 6.23 (2H, s), 6.86 (1H, m), 6.93 (1H, m), 6.98 (1H, m), 7.06 (1H, s), 7.15 (4H, m).<br>LRMS: m/z APCI 579 [M + H⁺], 577 [M − H⁻]. |
| 82 | 3,4-dimethylbenzyl-NH- | The compound was isolated as a pale brown foam.<br>¹H NMR (400 MHz, CD₃OD) δ −0.15 (3H, s), 0.01 (3H, s), 0.86 (9H, s), 1.03 (3H, d), 2.18 (3H, s), 2.18 (3H, s), 2.55 (3H, m), 2.84 (2H, m), 3.48 (2H, s), 4.27 (2H, s), 4.58 (1H, m), 6.15 (1H, m), 6.23 (2H, s), 6.99 (5H, m), 7.13 (1H, m), 7.17 (1H, m).<br>LRMS: m/z APCI 577 [M + H⁺], 575 [M − H⁻]. |
| 83 | 3,4-dimethoxybenzyl-NH- | The compound was isolated as a pale brown foam.<br>¹H NMR (400 MHz, CD₃OD) δ −0.15 (3H, s), 0.00 (3H, s), 0.85 (9H, s), 1.02 (3H, d), 2.55 (3H, m), 2.84 (2H, m), 3.48 (2H, s), 3.71 (3H, s), 3.77 (3H, s), 4.27 (2H, s), 4.58 (1H, m), 6.15 (1H, m), 6.22 (2H, s), 6.78 (2H, m), 6.85 (1H, m), 6.97 (1H, m), 7.06 (1H, s), 7.16 (2H, m).<br>LRMS: m/z APCI 609 [M + H⁺], 608 [M − H⁻]. |

| No | Q¹ | Data |
|---|---|---|
| 84 | (structure: N-methyl-2-ethoxybenzylamine fragment) | The compound was isolated as a pale brown foam.<br>¹H NMR (400 MHz, CD$_3$OD) δ −0.15 (3H, s), 0.01 (3H, s), 0.85 (9H, s), 1.03 (3H, d), 1.34 (3H, t), 2.53 (1H, m), 2.64 (2H, m), 2.84 (2H, m), 3.52 (2H, s), 4.00 (2H, q), 4.38 (2H, s), 4.58 (1H, m), 6.15 (1H, m), 6.23 (2H, s), 6.83 (1H, m), 6.88 (1H, m), 6.98 (1H, m), 7.05 (1H, s), 7.13 (2H, m), 7.18 (2H, m).<br>LRMS: m/z APCI 593 [M + H⁺], 591 [M − H⁻]. |
| 85 | (structure: N-methyl-2-chlorophenethylamine fragment) | The compound was isolated as a pale brown foam.<br>¹H NMR (400 MHz, CD$_3$OD) δ −0.15 (3H, s), 0.01 (3H, s), 0.86 (9H, s), 1.05 (3H, d), 2.58 (3H, m), 2.88 (5H, m), 3.41 (4H, m), 4.58 (1H, m), 6.14 (1H, m), 6.23 (2H, s), 7.00 (2H, m), 7.06 (1H, m), 7.18 (5H, m).<br>LRMS: m/z APCI 597 [M + H⁺], 595 [M − H⁻]. |
| 86 | (structure: N-methyl-4-carbamoylbenzylamine fragment) | The compound was isolated as a pale brown foam.<br>¹H NMR (400 MHz, CD$_3$OD) δ −0.15 (3H, s), 0.01 (3H, s), 0.83 (9H, s), 1.03 (3H, d), 2.58 (1H, m), 2.69 (2H, m), 2.94 (2H, m), 3.59 (2H, s), 4.38 (2H, s), 4.58 (1H, m), 6.15 (1H, m), 6.23 (2H, s), 7.05 (1H, d), 7.10 (1H, s), 7.15 (1H, d), 7.20 (1H, m), 7.32 (2H, d), 7.80 (2H, d).<br>LRMS: m/z APCI 592 [M + H⁺], 590 [M − H⁻]. |
| 87 | (structure: N-methyl-(1R)-indan-1-ylamine fragment) | The compound was isolated as a pale brown foam.<br>¹H NMR (400 MHz, CD$_3$OD) δ −0.15 (3H, s), 0.01 (3H, s), 0.85 (9H, s), 1.03 (3H, d), 1.85 (1H, m), 2.52 (2H, m), 2.65 (2H, m), 2.83 (3H, m), 3.00 (1H, m), 3.50 (2H, m), 4.58 (1H, m), 5.37 (1H, m), 6.15 (IH, m), 6.23 (2H, s), 7.00 (1H, d), 7.10 (7H, m).<br>LRMS: m/z APCI 575 [M + H⁺], 573 [M − H⁻]. |

PREPARATION 88

Methyl {3-[(2R)-2-aminopropyl]phenyl}acetate

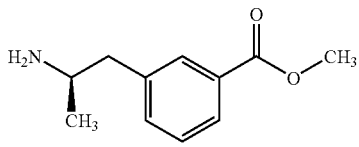

A solution of methyl [3-((2R)-2-{[(1R)-1-phenyl-ethyl]-amino}-propyl)-phenyl]-acetate (Preparation 89) (13.65 g, 40.9 mmol) and ammonium formate (12.9 g, 204 mmol) in ethanol (200 ml) was heated at reflux in the presence of 20% of palladium hydroxide on charcoal (Pd(OH)$_2$/C, 1.36 g). After 3 hours the reaction mixture was cooled to room temperature, filtered through arbocel and the filtrate concentrated in vacuo. The residue was partitioned between dichloromethane (200 ml) and 880 ammonia (100 ml) and the organic phase separated. The aqueous phase was extracted with further dichlorormethane (3×100 ml) and the combined organic extracts washed with brine (100 ml), dried (sodium sulfate) and reduced in vacuo to give the title compound (8.48 g) as a pale yellow oil.

¹H NMR (400 MHz, CDCl$_3$): δ=7.90-7.87 (2H, m), 7.38-7.34 (2H, m), 3.90 (3H, s), 3.26-3.17 (1H, m), 2.78-2.73 (1H, dd), 2.64-2.59 (1H, dd), 1.14-1.12 (3H, d) ppm. LRMS (electrospray): m/z [M+H]⁺ 194.

PREPARATION 89

Methyl [3-((2R)-2-{[(1R)-1-phenyl-ethyl]-amino}-propyl)-phenyl]-acetate hyrdrochloride

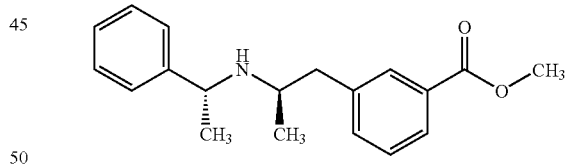

A solution of methyl [3-(2-oxopropyl)phenyl]acetate (Preparation 90) (45.3 g, 236 mmol), (R)-α-methyl benzylamine (27.6 ml, 214 mmol), sodium triacetoxyborohydride (68.1 g, 321 mmol) and acetic acid (14.7 ml, 257 mmol) in dichloromethane (1500 ml) was stirred at room temperature for 18 hours. The reaction mixture was quenched by addition of saturated aqueous sodium bicarbonate (600 ml) and allowed to stir until effervescence ceased. The organic phase was separated and the aqueous phase extracted with further dichloromethane (2×100 ml). The combined organic extracts were washed with brine (100 ml), dried (sodium sulfate), filtered through celite and reduced in vacuo. The oil was dissolved in methanol (200 ml), treated with 1M hydrogen chloride in methanol (300 ml) and reduced in vacuo to give a 4:1 mixture of diastereomers (R,R major) as an off-white, hydrochloride salt. Two successive crystallisations (diisopropylether/methanol) gave the title compound (27.3 g) as a colourless crystalline solid.

¹H NMR (400 MHz, CD₃OD): δ=7.92-7.90 (1H, d), 7.75 (1H, s), 7.55-7.49 (5H, m), 7.45-7.42 (1H, dd), 7.35-7.33 (1H, d), 4.68-4.63 (1H, q), 3.90 (3H, s), 3.43-3.38 (1H, dd), 3.25-3.19 (1H, m), 2.71-2.65 (1H, dd), 1.71-1.69 (3H, d), 1.17-1.16, (3H, d) ppm.

PREPARATION 90

Methyl [3-(2-oxopropyl)phenyl]acetate

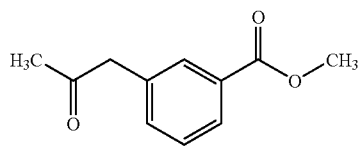

Tributyltin methoxide (80.3 ml, 279 mmol), methyl 3-bromobenzoate (53.5 g, 249 mmol), isopropenyl acetate (39.4 ml, 358 mmol), palladium(II)acetate (2.6 g, 11.6 mmol) and tri-o-tolylphosphine (7.1 g, 23.2 mmol) were stirred together in toluene (350 ml) at 100° C. under nitrogen for 18 hours. After cooling, the reaction was treated with 4M aqueous potassium fluoride solution (560 ml) and stirred for 2 hours. The resulting mixture was diluted with further toluene (200 ml) and filtered through celite, washing the filter pad with ethyl acetate. The organic phase was separated, dried (sodium sulfate) and reduced in vacuo. The residue was purified by flash column chromatography on silica gel eluting with ethylacetate:pentane (10:90, changing to 20:80, by volume) to give the title compound (45.3 g) as an orange oil.

¹H NMR (400 MHz, CDCl₃): δ=7.95-7.93 (1H, d), 7.87 (1H, s), 7.43-7.37 (2H, m), 3.91 (3H, s), 3.75 (2H, s), 2.18 (3H, s) ppm. LRMS (electrospray): m/z [M+Na]⁺ 215, [M−H]⁻ 191.

PREPARATION 91

3-{2-[2-(3,5-Bis-benzyloxy-phenyl)-2-(tert-butyl-dimethyl-sianyloxy)-ethylamino]-propyl}-benzoic acid methyl ester

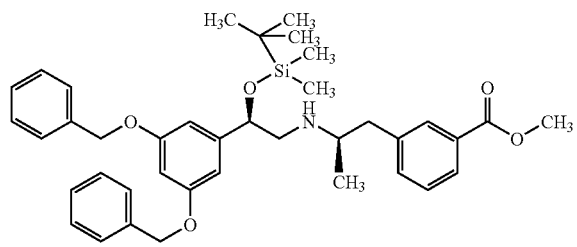

The compound of preparation 11 (7.10 g, 13.5 mmol) was added to a solution of the compound of preparation 88 (5.23 g. 27.0 mmol) in dichloromethane (50 mL) and the solvent removed in vacuo. The mixture was heated at 95° C. for 12 hours and cooled to room temperature. Diethyl ether (150 mL) was added and the reaction stirred for 1 hour, the resulting white precipitate was removed by filtration and the filtrate evaporated to furnish a yellow oil. The residue was purified by column chromatography on silica gel eluting with dichloromethane:methanol:880 ammonia (100:0:0 then 95:5:0.5) to furnish the title compound as a yellow oil, 4.30 g.

¹H NMR (400 MHz, CD₃OD) δ −0.23 (3H, s), −0.06 (3H, s), 0.78 (9H, s), 1.06 (3H, d), 2.57 (1H, m), 2.66 (2H, m), 2.88 (2H, m), 3.83 (3H, s), 4.64 (1H, m), 4.85 (4H, s), 6.46 (2H, s), 6.49 (1H, m), 7.32 (12H, m), 7.78 (1H, s), 7.82 (1H, m). LRMS: m/z APCl 640 [M+H⁺].

PREPARATION 92

3-{2-[2-(3,5-Bis-benzyloxy-phenyl)-2-(tert-butyl-dimethyl-silanyloxy)-ethylamino]-propyl}-benzoic acid hydrochloride

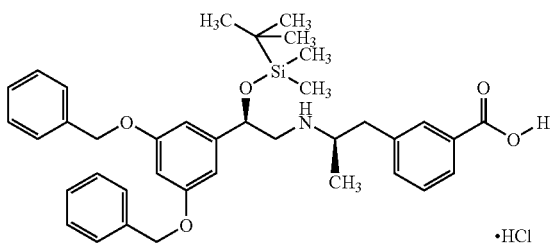

The compound of preparation 91 (5.35 g, 8.37 mmol) was stirred in tetrahydrofuran (20 mL) and 1M aqueous lithium hydroxide (18.4 mL, 18.4 mmol) was added in one portion. The reaction was stirred for 12 hours and then heated at 40° C. for 12 hours. Further 1M aqueous lithium hydroxide (36.8 mL, 36.8 mmol) and tetrahydrofuran (100 mL) added in one portion and reaction heated at 40° C. for 12 hours, reaction cooled and further 1M aqueous lithium hydroxide (36.8 mL, 36.8 mmol) added. The reaction was heated at 60° C. for 5 hours and cooled to room temperature, the tetrahydrofuran was removed under reduced pressure and dioxane (50 mL) added. The reaction was heated at 60° C. for 1 hour, cooled to room temperature and the solvent removed in vacuo. The residue was acidified to pH1 with 1M aqueous hydrochloric acid and extracted with dichloromethane:methanol (97:3; v/v; 3×150 mL), the combined organics were washed with brine (30 mL), dried (magnesium sulphate) and the solvent removed in vacuo to furnish the title compound as a yellow foam, 5.00 g.

¹H NMR (400 MHz, CD₃OD) δ −0.13 (3H, s), 0.07 (3H, s), 0.86 (9H, s), 1.24 (3H, d), 2.83 (1H, m), 3.19 (1H, m), 3.30 (2H, m), 3.59 (1H, m), 5.05 (1H, m), 5.11 (4H, s), 6.64 (3H, m), 7.30 (10H, m), 7.47 (2H, m), 7.92 (1H, s), 7.97 (1H, m). LRMS: m/z APCl 626 [M+H⁺].

PREPARATION 93

3-{2-[2-(tert-Butyl-dimethyl-silanyloxy)-2-(3,5-di-hydroxy-phenyl)-ethylamino]-propyl}-benzoic acid

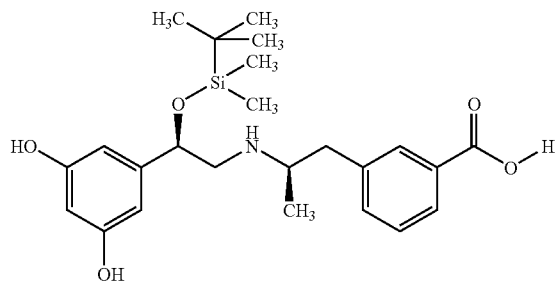

The compound of preparation 92 (4.97 g, 7.95 mmol) was dissolved in ethanol (300 mL) and ammonium formate (2.75 g, 60 mmol) and palladium hydroxide (500 mg) added in one portion. The reaction was heated under reflux for 1 hour, cooled to room temperature, filtered through Arbocel® and washed through with methanol (500 mL). The filtrate was condensed in vacuo to furnish the title compound as an off white solid 3.60 g.

$^1$H NMR (400 MHz, CD$_3$OD) δ −0.06 (3H, s), 0.05 (3H, s), 0.86 (9H, s), 1.23 (3H, d), 2.83 (1H, m), 3.12 (2H, m), 3.25 (1H, m), 3.51 (1H, m), 4.90 (1H, m), 6.24 (1H, m), 6.35 (2H, s), 7.27 (2H, m), 7.83 (1H, m), 7.88 (1H, m). LRMS: m/z APCI 446 [M+H$^+$].

Preparations 100 to 104 and 115 to 124 were prepared from preparation 33 and the appropriate amine, using the method of preparation 34. These compounds are of generic formula

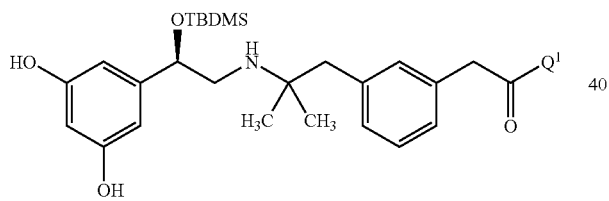

and are listed in the table below.

Preparations 96 to 99 were prepared from preparation 45 and the appropriate amine, using the method of preparation 34. These compounds are of generic formula

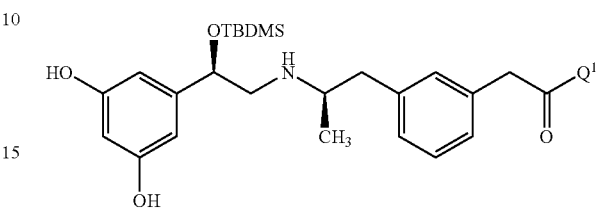

and are listed in the table below.

Preparations 94, 95 and 105 to 114 were prepared from preparation 93 and the appropriate amine, using the method of preparation 34. These compounds are of generic formula

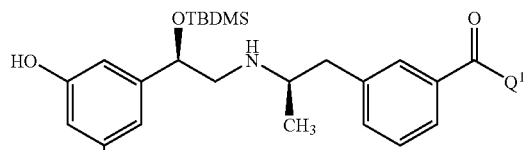

and are listed in the table below.

| No | Q$^1$ | Data |
|---|---|---|
| 94 | ![3-fluorophenethylamine] | The compound was isolated as a pale yellow solid. $^1$H NMR (400 MHz, CD$_3$OD) δ −0.15 (3H, s), −0.01 (3H, s), 0.85 (9H, s), 1.05 (3H, d), 2.73 (7H, m), 3.60 (2H, t), 4.60 (1H, m), 6.16 (1H, m), 6.25 (2H, s), 6.92 (1H, m), 7.05 (2H, m), 7.30 (3H, m), 7.60 (2H, m). LRMS: m/z APCI 567 [M + H$^+$]. |
| 95 | ![2-chlorophenethylamine] | The compound was isolated as a white solid. $^1$H NMR (400 MHz, CD$_3$OD) δ −0.15 (3H, s), −0.01 (3H, s), 0.83 (9H, s), 1.05 (3H, d), 2.73 (5H, m), 3.07 (2H, m), 3.63 (2H, t), 4.60 (1H, m), 6.16 (1H, m), 6.25 (2H, s), 7.20 (6H, m), 7.60 (2H, m). LRMS: m/z APCI 583 [M + H$^+$], 581 [M − H$^-$]. |

| No | Q¹ | Data |
|---|---|---|
| 96 | *N*-CH₂-(naphthalen-1-yl) | The compound was isolated as a pale brown foam.<br>¹H NMR (400 MHz, CD₃OD) δ −0.22 (3H, s), 0.01 (3H, s), 0.90 (9H, s), 1.08 (3H, d), 2.58 (1H, m), 2.71 (2H, m), 2.88 (2H, m), 3.61 (2H, s), 4.65 (2H, s), 6.28 (1H, m), 6.38 (2H, s), 7.10 (2H, m), 7.35 (2H, m), 7.58 (3H, m), 7.91 (1H, d), 7.95 (1H, d), 8.08 (1H, d).<br>LRMS: m/z APCI 599 [M + H⁺]. |
| 97 | *N*-CH₂-(2-fluoro-5-trifluoromethylphenyl) | The compound was isolated as a white foam.<br>¹H NMR (400 MHz, CD₃OD) δ −0.18 (3H, s), 0.00 (3H, s), 0.82 (9H, s), 1.04 (3H, d), 2.58 (1H, m), 2.71 (2H, m), 2.83 (2H, m), 3.51 (2H, s), 4.45 (2H, s), 4.58 (1H, m), 6.18 (1H, s), 6.23 (2H, s), 6.98 (1H, m), 7.05 (1H, s), 7.23 (3H, m), 7.58 (2H, m).<br>LRMS: m/z APCI 635 [M + H⁺], 633 [M − H⁻]. |
| 98 | *N*-CH₂-(3-chlorophenyl) | The compound was isolated as a white foam.<br>¹H NMR (400 MHz, CD₃OD) δ −0.15 (3H, s), 0.03 (3H, s), 0.82 (9H, s), 1.04 (3H, d), 2.58 (1H, m), 2.68 (2H, m), 2.83 (2H, m), 3.51 (2H, s), 4.38 (2H, s), 4.58 (1H, m), 6.18 (1H, s), 6.23 (2H, s), 6.98 (1H, d), 7.05 (1H, s), 7.23 (6H, m).<br>LRMS: m/z APCI 583 [M + H⁺], 581 [M − H⁻]. |
| 99 | *N*-CH₂-(4-fluoro-3-trifluoromethylphenyl) | The compound was isolated as a white foam.<br>¹H NMR (400 MHz, CD₃OD) δ −0.16 (3H, s), −0.03 (3H, s), 0.82 (9H, s), 1.04 (3H, d), 2.60 (3H, m), 2.83 (2H, m), 3.51 (2H, s), 4.38 (2H, s), 4.58 (1H, m), 6.18 (1H, s), 6.23 (2H, s), 6.98 (1H, d), 7.05 (1H, s), 7.09 (1H, d), 7.23 (2H, m), 7.51 (2H, m).<br>LRMS: m/z APCI 635 [M + H⁺], 633 [M − H⁻]. |
| 100 | *N*-CH₂-(2-methylthiophenyl) | The compound was isolated as a white solid.<br>¹H NMR (400 MHz, CD₃OD) δ −0.08 (3H, s), 0.04 (3H, s), 0.87 (9H, s), 1.08 (3H, s), 1.10 (3H, s), 2.48 (3H, s), 2.74 (4H, m), 3.58 (2H, s), 4.47 (2H, s), 4.64 (1H, m), 6.22 (1H, m), 6.34 (2H, s), 7.11 (8H, m).<br>LRMS: m/z electrospray 611 [M + H⁺], 608 [M − H⁻]. |
| 101 | *N*-CH₂-(4-carbamoylphenyl) | The compound was isolated as a white solid.<br>¹H NMR (400 MHz, CD₃OD) δ −0.08 (3H, s), 0.04 (3H, s), 0.86 (9H, s), 1.10 (3H, s), 1.12 (3H, s), 2.76 (4H, m), 3.59 (2H, s), 4.46 (2H, s), 4.64 (1H, m), 6.22 (1H, m), 6.34 (2H, s), 7.10 (1H, d), 7.16 (1H, s), 7.25 (2H, m), 7.34 (2H, d), 7.83 (2H, d).<br>LRMS: m/z electrospray 607 [M + H⁺], 605 [M − H⁻]. |
| 102 | *N*-CH₂-(4-sulfamoylphenyl) | The compound was isolated as a white solid.<br>¹H NMR (400 MHz, CD₃OD) δ −0.08 (3H, s), 0.05 (3H, s), 0.87 (9H, s), 1.10 (3H, s), 1.12 (3H, s), 2.69 (3H, m), 2.90 (1H, m), 3.59 (2H, s), 4.47 (2H, s), 4.67 (1H, m), 6.22 (1H, m), 6.34 (2H, s), 7.10 (1H, d), 7.15 (1H, s), 7.22 (1H, m), 7.27 (1H, m), 7.41 (2H, d), 7.84 (2H, d).<br>LRMS: m/z electrospray 643 [M + H⁺], 640 [M − H⁻]. |
| 103 | *N*-CH₂-(4-methoxycarbonylphenyl) | The compound was isolated as a white solid.<br>¹H NMR (400 MHz, CD₃OD) δ −0.08 (3H, s), 0.04 (3H, s), 0.86 (9H, s), 1.08 (3H, s), 1.11 (3H, s), 2.86 (4H, m), 3.59 (2H, s), 3.92 (3H, s), 4.47 (2H, s), 4.63 (1H, m), 6.22 (1H, m), 6.34 (2H, s), 7.10 (1H, d), 7.15 (1H, s), 7.22 (2H, m), 7.36 (2H, d), 7.96 (2H, d).<br>LRMS: m/z electrospray 623 [M + H⁺], 620 [M − H⁻]. |
| 104 | *N*-(1-benzylpiperidin-4-yl) | The compound was isolated as a white solid.<br>¹H NMR (400 MHz, CD₃OD) δ −0.09 (3H, s), 0.04 (3H, s), 0.86 (9H, s), 1.10 (3H, s), 1.12 (3H, s), 1.55 (2H, m), 1.87 (2H, m), 2.15 (2H, m), 2.75 (3H, m), 2.86 (3H, m), 3.49 (2H, s), 3.56 (2H, s), 3.68 (1H, m), 4.63 (1H, m), 6.22 (1H, m), 6.34 (2H, s), 7.06 (1H, m), 7.14 (1H, s), 7.19 (1H, m), 7.25 (1H, m), 7.30 (1H, m), 7.35 (4H, m).<br>LRMS: m/z electrospray 647 [M + H⁺], 645 [M − H⁻]. |

| No | Q¹ | Data |
|---|---|---|
| 105 | phenethylamino group (–NH–CH₂CH₂–C₆H₅) | The compound was isolated as a pale brown foam.<br>¹H NMR (400 MHz, CD₃OD) δ −0.15 (3H, s), −0.01 (3H, s), 0.84 (9H, s), 1.06 (3H, d), 2.63 (2H, m), 2.76 (1H, m), 2.85 (1H, m), 2.90 (3H, m), 3.59 (2H, t), 4.61 (1H, m), 6.17 (1H, m), 6.25 (2H, s), 7.18 (1H, m), 7.25 (5H, m), 7.35 (1H, m), 7.60 (2H, m).<br>LRMS: m/z APCI 549 [M + H⁺], 547 [M − H⁻]. |
| 106 | 2-(4-fluoro-2-methylphenyl)ethylamino | The compound was isolated as a pale brown foam.<br>¹H NMR (400 MHz, CD₃OD) δ −0.15 (3H, s), −0.01 (3H, s), 0.82 (9H, s), 1.05 (3H, d), 2.32 (3H, s), 2.63 (2H, m), 2.76 (1H, m), 2.85 (1H, m), 2.90 (3H, m), 3.57 (2H, t), 4.61 (1H, m), 6.17 (1H, m), 6.25 (2H, s), 6.81 (1H, m), 6.92 (1H, m), 7.13 (1H, m), 7.27 (1H, m), 7.36 (1H, m), 7.60 (2H, m).<br>LRMS: m/z APCI 581 [M + H⁺], 579 [M − H⁻]. |
| 107 | 2-(2-trifluoromethylphenyl)ethylamino | The compound was isolated as a pale brown foam.<br>¹H NMR (400 MHz, CD₃OD) δ −0.15 (3H, s), −0.01 (3H, s), 0.85 (9H, s), 1.06 (3H, d), 2.63 (2H, m), 2.77 (1H, m), 2.85 (1H, m), 2.95 (1H, m), 3.13 (2H, t), 3.63 (2H, t), 4.61 (1H, m), 6.16 (1H, m), 6.24 (2H, s), 7.28 (1H, m), 7.36 (2H, m), 7.51 (2H, m), 7.65 (3H, m). |
| 108 | 2-(naphthalen-1-yl)ethylamino | The compound was isolated as a pale brown foam.<br>¹H NMR (400 MHz, CD₃OD) δ −0.15 (3H, s), −0.01 (3H, s), 0.85 (9H, s), 1.05 (3H, d), 2.63 (2H, m), 2.75 (1H, m), 2.85 (2H, m), 3.41 (2H, t), 3.52 (2H, t), 4.61 (1H, m), 6.17 (1H, m), 6.25 (2H, s), 7.27 (1H, m), 7.36 (3H, m), 7.48 (3H, m), 7.62 (1H, m), 7.75 (1H, m), 7.85 (1H, m), 8.26 (1H, m).<br>LRMS: m/z APCI 599 [M + H⁺], 597 [M − H⁻]. |
| 109 | 2-(2,4,5-trimethylphenyl)ethylamino | The compound was isolated as a pale brown foam.<br>¹H NMR (400 MHz, CD₃OD) δ −0.15 (3H, s), −0.01 (3H, s), 0.84 (9H, s), 1.05 (3H, d), 2.17 (6H, s), 2.28 (3H, s), 2.63 (2H, m), 2.75 (4H, m), 2.95 (1H, m), 3.50 (2H, t), 4.61 (1H, m), 6.17 (1H, m), 6.24 (2H, s), 6.88 (1H, s), 6.93 (1H, s), 7.27 (1H, m), 7.36 (1H, m), 7.59 (1H, s), 7.62 (1H, m).<br>LRMS: m/z APCI 591 [M + H⁺], 590 [M − H⁻]. |
| 110 | 2-(2,3-dimethylphenyl)ethylamino | The compound was isolated as a pale brown foam.<br>¹H NMR (400 MHz, CD₃OD) δ −0.15 (3H, s), −0.01 (3H, s), 0.84 (9H, s), 1.05 (3H, d), 2.27 (3H, s), 2.28 (3H, s), 2.63 (2H, m), 2.77 (1H, m), 2.84 (1H, m), 2.93 (3H, m), 3.53 (2H, t), 4.61 (1H, m), 6.17 (1H, m), 6.24 (2H, s), 7.00 (3H, m), 7.27 (1H, m), 7.36 (1H, m), 7.62 (2H, m).<br>LRMS: m/z APCI 577 [M + H⁺], 575 [M − H⁻]. |
| 111 | 2-(3-chloro-2-hydroxyphenyl)ethylamino | The compound was isolated as a pale brown foam.<br>¹H NMR (400 MHz, CD₃OD) δ −0.15 (3H, s), −0.01 (3H, s), 0.84 (9H, s), 1.06 (3H, d), 2.63 (2H, m), 2.77 (1H, m), 2.84 (1H, m), 2.93 (3H, m), 3.61 (2H, t), 4.61 (1H, m), 6.17 (1H, m), 6.23 (2H, s), 6.76 (1H, t), 7.07 (1H, m), 7.17 (1H, m), 7.27 (1H, m), 7.35 (1H, m), 7.58 (2H, m).<br>LRMS: m/z APCI 599 [M + H⁺], 597 [M − H⁻]. |
| 112 | 2-(4-chlorophenyl)ethylamino | The compound was isolated as a pale brown foam.<br>¹H NMR (400 MHz, CD₃OD) δ −0.15 (3H, s), −0.01 (3H, s), 0.84 (9H, s), 1.05 (3H, d), 2.63 (2H, m), 2.76 (1H, m), 2.84 (4H, m), 3.58 (2H, t), 4.60 (1H, m), 6.16 (1H, m), 6.24 (2H, s), 7.27 (5H, m), 7.35 (1H, m), 7.56 (1H, s), 7.60 (1H, m).<br>LRMS: m/z APCI 583 [M + H⁺], 581 [M − H⁻]. |

| No | Q¹ | Data |
|---|---|---|
| 113 | 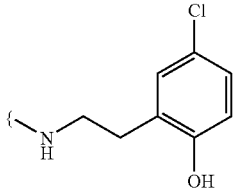 | The compound was isolated as a pale brown foam.<br>¹H NMR (400 MHz, CD₃OD) δ −0.15 (3H, s), −0.01 (3H, s), 0.83 (9H, s), 1.06 (3H, d), 2.63 (2H, m), 2.77 (1H, m), 2.84 (4H, m), 3.58 (2H, t), 4.60 (1H, m), 6.17 (1H, m), 6.24 (2H, s), 6.74 (1H, m), 7.00 (1H, m), 7.10 (1H, m), 7.26 (1H, m), 7.35 (1H, m), 7.57 (1H, s), 7.61 (1H, m).<br>LRMS: m/z APCI 599 [M + H⁺], 597 [M − H⁻]. |
| 114 | 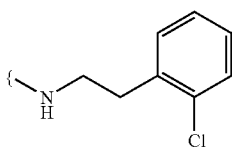 | The compound was isolated as a pale brown foam.<br>¹H NMR (400 MHz, CD₃OD) δ −0.15 (3H, s), −0.02 (3H, s), 0.82 (9H, s), 1.04 (3H, d), 2.63 (2H, m), 2.77 (1H, m), 2.85 (1H, m), 2.94 (1H, m), 3.04 (2H, t), 3.62 (2H, t), 4.60 (1H, m), 6.17 (1H, m), 6.24 (2H, s), 6.98 (1H, m), 7.18 (1H, m), 7.27 (1H, m), 7.35 (2H, m), 7.59 (1H, m).<br>LRMS: m/z APCI 601 [M + H⁺], 599 [M − H⁻]. |
| 115 | 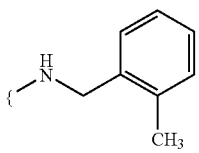 | The compound was isolated as a white foam.<br>¹H NMR (400 MHz, CD₃OD) δ −0.09 (3H, s), 0.04 (3H, s), 0.78 (9H, s), 1.04 (3H, s), 1.05 (3H, s), 2.22 (3H, s), 2.74 (3H, m), 2.83 (1H, m), 3.56 (2H, s), 4.37 (2H, s), 4.55 (1H, m), 6.18 (1H, m), 6.36 (2H, s), 7.04 (1H, d), 7.12 (6H, m), 7.21 (1H, m).<br>LRMS: m/z electrospray 577 [M + H⁺]. |
| 116 | 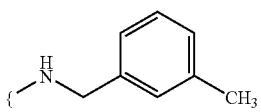 | The compound was isolated as a white foam.<br>LRMS: m/z electrospray 577 [M + H⁺]. |
| 117 | 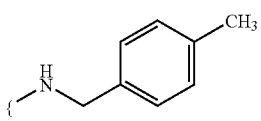 | The compound was isolated as a white foam.<br>LRMS: m/z electrospray 577 [M + H⁺]. |
| 118 | 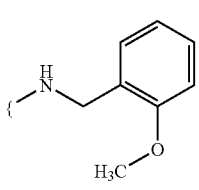 | The compound was isolated as a white foam.<br>¹H NMR (400 MHz, CD₃OD) δ −0.09 (3H, s), 0.04 (3H, s), 0.98 (9H, s), 1.04 (3H, s), 1.05 (3H, s), 2.68 (2H, t), 2.77 (1H, m), 2.83 (1H, m), 3.56 (2H, s), 3.79 (3H, s), 4.37 (2H, s), 4.55 (1H, m), 6.18 (1H, m), 6.37 (2H, s), 6.82 (1H, t), 6.92 (1H, d), 7.03 (1H, d), 7.12 (3H, m), 7.22 (2H, m).<br>LRMS: m/z electrospray 593 [M + H⁺], 591 [M − H⁻]. |
| 119 | 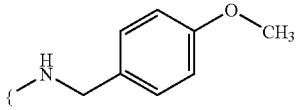 | The compound was isolated as a white foam.<br>LRMS: m/z electrospray 594 [M + H⁺], 591 [M − H⁻]. |
| 120 | 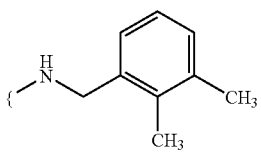 | The compound was isolated as a white foam.<br>LRMS: m/z electrospray 591 [M + H⁺], 589 [M − H⁻]. |
| 121 | 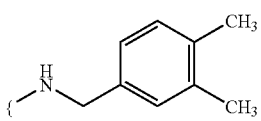 | The compound was isolated as a white foam.<br>LRMS: m/z electrospray 591 [M + H⁺], 589 [M − H⁻]. |
| 122 | 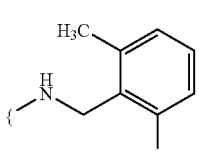 | The compound was isolated as a white foam.<br>¹H NMR (400 MHz, CD₃OD) δ −0.09 (3H, s), 0.04 (3H, s), 0.94 (9H, s), 1.04 (3H, s), 1.05 (3H, s), 2.37 (3H, s), 2.68 (3H, m), 2.83 (1H, m), 3.47 (2H, s), 4.53 (2H, s), 4.55 (1H, m), 6.18 (1H, m), 6.36 (2H, s), 7.04 (1H, d), 7.09 (1H, d), 7.18 (4H, m), 7.21 (1H, m).<br>LRMS: m/z electrospray 611 [M + H⁺], 609 [M − H⁻]. |

| No | Q¹ | Data |
|---|---|---|
| 123 | 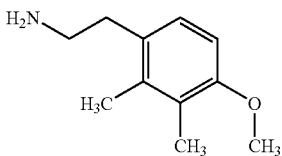 | The compound was isolated as a white foam.<br>LRMS: m/z electrospray 611 [M + H⁺], 609 [M − H⁻]. |
| 124 | 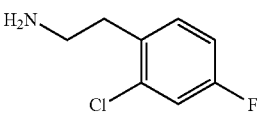 | The compound was isolated as a white foam.<br>LRMS: m/z electrospray 658 [M + H⁺]. |

PREPARATION 125

2-(4-Methoxy-2,3-dimethyl-phenyl)-ethylamine

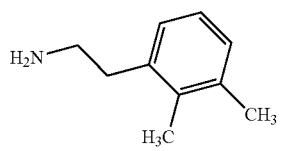

A mixture of (4-methoxy-2,3-dimethyl-phenyl)-acetonitrile (200 mg, 1.14 mmol) and Raney® nickel (50 mg) in 2M methanolic ammonia (10 mL) was stirred under 60 psi of hydrogen gas at room temperature for 18 hours. Tlc analysis showed that not all of the starting material had been consumed and so further Raney® nickel (50 mg) in 2M methanolic ammonia (10 mL) was added. The reaction mixture was stirred under 60 psi of hydrogen gas for an additional 18 hours at room temperature and was then filtered through Arbocel®. The filtrate was concentrated in vacuo and the residue was purified by column chromatography on silica gel, eluting with dichloromethane:methanol:0.88 ammonia, 100:0:0 to 90:10:1 to afford the title product as a pale brown solid, 233 mg.

$^1$H NMR (400 MHz, CDCl$_3$) δ: 6.96 (1H, d), 6.66 (1H, d), 3.80 (3H, s), 2.96-2.84 (2H, m), 2.81-2.73 (2H, m), 2.22 (3H, s), 2.17 (3H, s), 1.63 (2H, s) ppm LRMS APCl m/z 180 [M+H]⁺

PREPARATION 126

2-(2,3-Dimethyl-phenyl)-ethylamine

A mixture of 2,3-dimethylphenylacetonitrile (*J. Org Chem*, 51(26), 5157-60; 1986), (190 mg, 1.31 mmol) and Raney® nickel (100 mg) in 2M methanolic ammonia (5 mL) was stirred under 50 psi of hydrogen gas for 4 days. The mixture was then filtered through Arbocel® and concentrated in vacuo to afford the title compound as a solid, 130 mg.

$^1$H NMR (400 MHz, CDCl$_3$) δ: 7.02-6.94 (3H, m), 2.26-2.13 (10H, m) ppm LRMS ESI m/z 150 [M+H]⁺

PREPARATION 127

2-(2-Chloro-4-fluoro-phenyl)-ethylamine

Sodium borohydride (1.73 g, 45.51 mmol) was added portionwise to a solution of 2-chloro-4-fluorophenylacetonitrile (1.04 g, 6.15 mmol) and cobalt (II) chloride hexahydrate (2.18 g, 9.22 mmol) in methanol (30 mL) and the mixture was stirred at room temperature for 3 hours. The suspension was then filtered though Celite®, concentrated in vacuo and the residue was partitioned between 1M hydrochloric acid (40 mL) and dichloromethane (40 mL). The aqueous phase was separated, basified to pH 11 with 1M ammonia solution and extracted with dichloromethane (2×40 mL). The combined organic solution was washed with brine (30 mL), dried over magnesium sulfate and concentrated in vacuo. The residue was purified by column chromatography on silica gel, eluting with dichloromethane:methanol:0.88 ammonia, 100:0:0 to 98:2:0.2, to afford the title compound as a yellow oil, 350 mg.

¹H NMR (400 MHz, CDCl₃) δ: 7.30 (1H, dd), 7.17 (1H, dd), 6.99 (1H, m), 2.86 (4H, m) ppm LRMS APCl m/z 174 [M+H]⁺

PREPARATION 128

2-(5-Chloro-2-methoxy-phenyl)-ethylamine

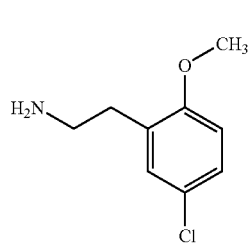

Chlorotrimethylsilane (2 mL, 16 mmol) was added dropwise to lithium borohydride (2M in tetrahydrofuran, 4 mL, 8 mmol). A solution of 2-methoxy-5-chlorophenylacetonitrile (312 mg, 4 mmol) in tetrahydrofuran (2 mL) was then added at 0° C. and the mixture was allowed to stir for 24 hours, whilst warming to room temperature. The mixture was then diluted with methanol (20 mL) and concentrated in vacuo. The residue was taken up in 20% potassium hydroxide solution (20 mL), extracted with dichloromethane (3×20 mL) and the combined organic solution was dried over magnesium sulfate and concentrated in vacuo. The residue was purified by column chromatography using an Isolute® SCX-2 cartridge, eluting with methanol followed by 1M ammonia in methanol, to give an oily residue. The oil was triturated with diethyl ether to afford the title compound, 485 mg.

¹H NMR (400 MHz, CDCl₃) δ: 7.11-7.00 (2H, m), 6.75-6.65 (1H, m) 3.72 (3H, s), 2.90-2.80 (2H, m), 2.70-2.60 (2H, m) ppm

PREPARATION 129

2-(5-Chloro-2-hydroxy-phenyl)-ethylamine

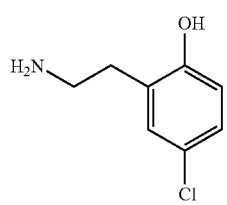

The amine of preparation 128 (66 mg, 0.36 mmol) was dissolved in 48% aqueous HBr and heated at 80° C. with stirring for 12 hours. The reaction was cooled to room temperature and the solvent removed in vacuo to give a brown gum. This was dissolved in methanol (5 mL) and purified by ion exchange column to furnish the title compound as a brown gum, 26 mg.

¹H NMR (400 MHz, CDCl₃) δ: 2.70 (2H, t), 2.90 (2H, t), 6.70 (1H, d), 6.98 (1H, m), 7.02 (1H, s) ppm LRMS APCl m/z 172 [M+H]⁺

PREPARATION 130

2-(5-Fluoro-2-methyl-phenyl)-ethylamine

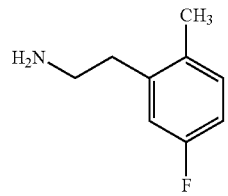

This compound was prepared using the method of preparation 128 and the appropriate nitrile.

¹H NMR (400 MHz, CDCl₃) δ: 7.07 (1H, m), 6.83 (2H, m), 2.97 (2H, t), 2.78 (2H, m) 2.27 (3H, s) ppm LRMS APCl m/z 154 [M+H]⁺

PREPARATION 131 tert-butyl (3-iodobenzyl)carbamate

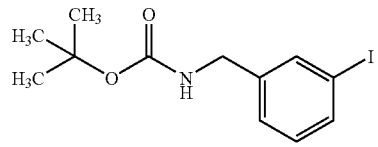

A suspension of 3-iodobenzylamine hydrochloride (4.95 g, 18.4 mmol) in dichloromethane (100 ml) was treated with triethylamine (3.1 ml, 22 mmol) and di-t-butyl dicarbonate (4.40 g, 20 mmol) and the resulting solution left to stir at room temperature under a nitrogen atmosphere for 1.5 hours. The reaction mixture was washed with 2M hydrochloric acid (30 ml), water (30 ml), dried (sodium sulfate), and the solvent removed in vacuo to give the title compound as a colourless solid (6.43 g).

¹HNMR (400 MHz, CDCl₃) δ: 1.46 (s, 9H), 4.21-4.30 (m, 2H), 4.79-4.89 (bs, 1H), 7.06 (dd, 1H), 7.25 (d, 1H), 7.60 (d, 1H), 7.63 (s, 1H) ppm. MS (electrospray) m/z 332 [M–H]⁻, 356 [M+Na]⁺

PREPARATION 132 tert-butyl [(4'-hydroxybiphenyl-3-yl)methyl]carbamate

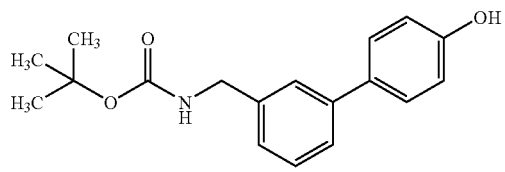

A solution of the iodide from preparation 131 (0.75 g, 2.25 mmol), 4-hydroxy phenylboronic acid (0.62 g, 4.50 mmol), 1,1′-Bis(diphenylphosphino)ferrocenyl palladium(II)chloride (0.11 g, 0.14 mmol), in N,N-dimethylformamide (14 ml) was treated with 2M aq. sodium carbonate (4 ml) and the resulting mixture heated at 80° C. under a nitrogen atmosphere for 16 hours. The solvent was removed under reduced pressure and the residue purified by column chromatography on silica gel eluting with ethyl acetate:pentane (1:3) to give the title compound as a pale pink crystalline solid (0.73 g).

$^1$HNMR (400 MHz, CDCl$_3$) δ: 1.47 (s, 9H), 4.33-4.41 (m), 4.87-4.94 (bs, 1H), 6.89 (d, 2H), 7.21 (d, 1H), 7.37 (dd, 1H), 7.43-7.45 (m, 4H) ppm. MS (electrospray) m/z 298 [M−H]$^-$, 322 [M+Na]$^+$

PREPARATION 133

3′-(aminomethyl)biphenyl-4-ol hydrochloride

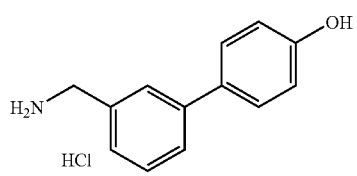

The phenol from preparation 132 (0.73 g, 2.43 mmol) was treated with 4M HCl in dioxan (6 ml, 24.3 mmol) and the resulting solution allowed to stir at room temperature for 3 hours. The solvent was removed in vacuo to give the title compound as a colourless solid.

$^1$HNMR (400 MHz, CD$_3$OD) δ: 4.17 (s, 2H), 6.87 (d, 2H), 7.34 (d, 1H), 7.45-7.50 (m, 3H), 7.61 (d, 1H), 7.65 (s, 1H) ppm. MS (electrospray) m/z 198 [M−H]$^-$, 200 [M+H]$^+$

PREPARATION 134

2-(3-Chloro-2-hydroxy-phenyl)-ethylamine

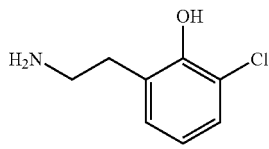

Prepared according to the procedure described in DE1959898.

PREPARATION 135

Methyl-3-[(2R)-2-aminopropyl)phenyl]propanoate

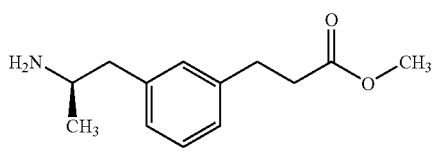

Prepared according to the procedure used for preparation 22, using methyl-[3-((2R)-2-{[(1R)-1-phenylethyl]amino}propyl)phenyl]propanoate hydrochloride (Preparation 136) to give the title compound as a brown oil.

$^1$H NMR (400 MHz, CD$_3$OD): δ=7.21-7.17 (1H, t), 7.03-7.01 (3H, m), 3.61 (3H, s), 3.11-3.03 (1H, m), 2.91-2.87 (2H, t), 2.64-2.54 (4H, m), 1.07-1.05 (3H, d) ppm. LRMS (electrospray) : m/z [M+H]$^+$ 222.

PREPARATION 136

Methyl [3-((2R)-2-{[(1R)-1-phenylethyl]amino}propyl)phenyl]propanoate hydrochloride

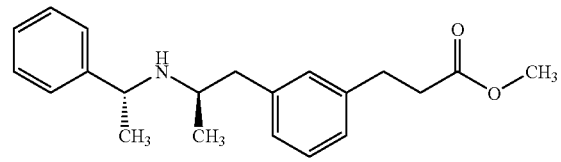

Prepared according to the procedure used for preparation 23, using methyl-3-[3-(2-oxopropyl)phenyl]propanoate (Preparation 137) to give the title compound as a white crystalline solid.

$^1$H NMR (400 MHz, CD$_3$OD): δ=7.54-7.47 (5H, m), 7.23-7.19 (1H, t), 7.12-7.10 (1H, d), 6.92-6.91 (2H, d), 4.64-4.59 (1H, q), 3.61 (3H, s), 3.34-3.29 (1H, m), 3.20-3.12 (1H, m), 2.89-2.85 (2H, t), 2.62-2.56 (3H, m), 1.71-1.69 (3H, d), 1.18-1.16 (3H, d) ppm. LRMS (electrospray): m/z [M+H]$^+$ 326.

PREPARATION 137

Methyl-3-[3-(2-oxopropyl)phenyl]propanoate

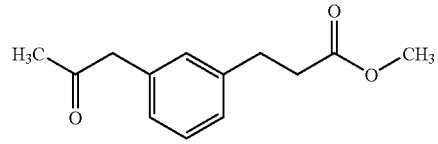

A suspension of methyl (2E)-3-[3-(2-oxopropyl)phenyl]acrylate (5.00 g, Preparation 138) and 10% palladium on carbon (500 mg) in ethanol (50 ml) was stirred under an atmosphere of hydrogen (60 psi) at room temperature for 16 hours. The catalyst was filtered off through arbocel and the filtrate concentrated in vacuo to give the title compound as a pale yellow oil which was used without further purification.

$^1$H NMR (400 MHz, CD$_3$OD): δ=7.27-7.23 (1H, q), 7.11-7.09 (1H, d), 7.05-7.04 (2H, d), 3.66 (5H, s), 2.96-2.92 (2H, t), 2.64-2.60 (2H, t), 2.14 (3H, s) ppm. LRMS (electrospray): m/z [M+Na]+ 243, [M–H]− 219.

PREPARATION 138

Methyl (2E)-3-[3-(2-oxopropyl)phenyl]acrylate

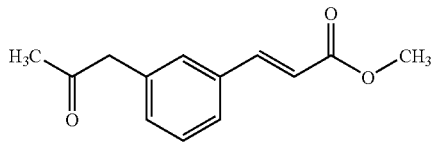

A solution of 3-bromophenylacetone (50.0 g, 235 mmol), methyl acrylate (40.4 g, 469 mmol), palladium(II)acetate (7.9 g, 35.2 mmol), tri-ortho-tolylphosphine (21.4 g, 70.4 mmol) and triethylamine (82 ml) in acetonitrile (900 ml) was heated at reflux under a nitrogen atmosphere for a period of 16 hours. The reaction mixture was cooled to room temperature and the solvent removed in vacuo. Purification by flash column chromatography eluting with pentane:ethyl acetate (90:10 changing to 70:30 by volume) gave the title compound as an orange oil (54.3 g).

$^1$H NMR (400 MHz, CD$_3$OD): δ=7.66-7.62 (1H, d), 7.41-7.39 (1H, d), 7.34-7.31 (2H, t), 7.20-7.18 (1H, d), 6.43-6.39 (1H, d), 3.77 (3H, s), 3.70 (2H, s), 2.15 (3H, s) ppm. LRMS (electrospray) : m/z [M+Na]+ 241, [M–H]− 217.

PREPARATION 139

3-(3-{2-[2-(3,5-Bis-benzyloxy-phenyl)-2-(tert-butyl-dimethyl-silanyloxy)-ethylamino]-propyl}-phenyl)-propionic acid methyl ester

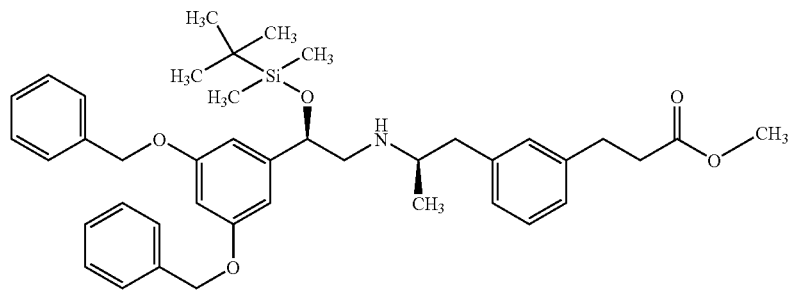

The bromide of preparation 11 (3.46 g, 6.56 mmol) and the amine of preparation 135 (2.90 g, 13.1 mmol) were combined in dichloromethane (50 mL) and the solvent removed in vacuo. The resulting oil was heated at 90° C. for 12 hours and cooled to room temperature, the orange oil was stirred in ether (200 mL) for 5 minutes and the ethereal layer decanted off carefully. The remaining orange oil was stirred with ether (2×200 mL) a further two times and the ether layers were combined and the solvent removed in vacuo. The resulting orange oil was purified by flash column chromatography eluting with dichloromethane:methanol:ammonia (100:0:0 then 96:4:0.4) to furnish the title compound as a golden oil (3.40 g).

$^1$H NMR (400 MHz, CD$_3$OD) δ: −0.20 (3H, s), −0.05 (3H, s), 0.82 (9H, s), 1.03 (3H, d), 2.52-2.65 (5H, m), 2.79-2.94 (4H, m), 3.60 (3H, s), 4.66 (1H, m), 5.04 (4H, m), 6.49 (2H, s), 6.53 (1H, m), 6.89-6.96 (2H, m), 6.99 (1H, m), 7.15 (1H, m), 7.23-7.44 (10H, m); LRMS APCl m/z 668 [M+H]+

PREPARATION 140

3-(3-{2-[2-(3,5-Bis-benzyloxy-phenyl)-2-(tert-butyl-dimethyl-sianyloxy)-ethylamino]-propyl}-phenyl)-propionic acid hydrochloride

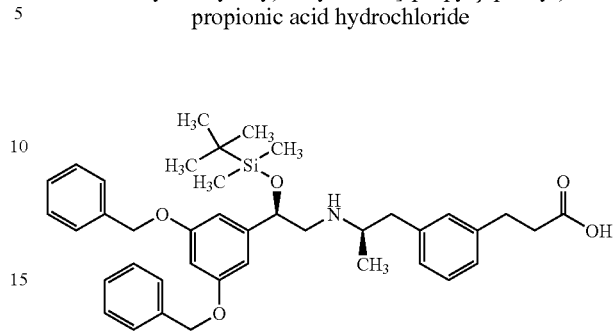

The ester of preparation 139 (3.40 g, 5.10 mmol) in tetrahydrofuran (15 mL) was treated with lithium hydroxide (1M, 11.2 mL, 11.21 mmol). Dioxane (50 mL) and water (10 mL) were added and the resulting solution stirred for 20 h. The solution was acidified to pH 1 with hydrochloric acid (1N) and extracted with dichloromethane (3×150 mL). The organics were washed with brine (50 mL) and dried (magnesium sulfate). Filtration and evaporation of the solvent left a white foam (3.5 g, 91%)

$^1$H NMR (400 MHz, CD$_3$OD) δ: −0.13 (3H, s), 0.06 (3H, s), 0.86 (9H, s), 1.03 (3H, d), 2.58 (2H, t), 2.75 (1H, m), 2.88 (2H, t), 3.06 (1H, m), 3.23 (1H, m), 3.34 (1H, m), 3.55 (1H, m), 5.04-5.16 (5H, m), 6.66 (3H, m), 7.06 (1H, m), 7.12 (1H, s), 7.18 (1H, m), 7.23-7.47 (11H, m); LRMS APCl m/z 655 [M+H]+

PREPARATION 141

3-(3-{2-[2-(tert-Butyldimethylsilanyloxy)-2-(3,5-dihydroxyphenyl)ethylamino]propyl}phenyl)propionic acid

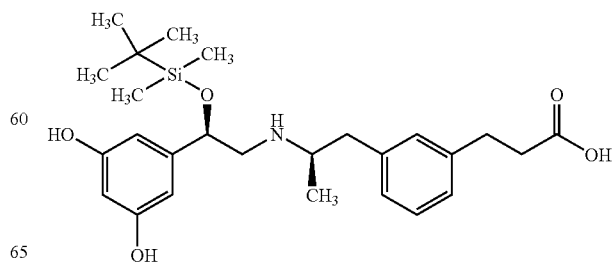

Prepared according to the procedure used for preparation 13, using 3-(3-{2-[2-(3,5-Bis-benzyloxy-phenyl)-2-(tert-butyl-dimethyl-silanyloxy)-ethylamino]-propyl}-phenyl)-propionic acid hydrochloride (Preparation 140) to give the title compound as a yellow solid.

¹H NMR (400 MHz, CD₃OD) δ: 0.06 (3H, s), 0.08 (3H, s), 0.86 (9H, s), 1.22 (3H, d), 2.54 (2H, t), 2.74 (1H, m), 2.90 (2H, t), 3.15 (1H, m), 3.26 (1H, m), 3.45 (1H, m), 4.90 (1H, m), 6.26 (1H, m), 6.35 (2H, s), 7.02 (1H, m), 7.08 (1H, s), 7.16 (1H, m), 7.24 (1H, m) ; LRMS APCl m/z 474 [M+H]⁺

PREPARATION 142

3-(3-{2-[2-(tert-Butyldimethylsilanyloxy)-2-(3,5-dihydroxyphenyl)ethyl amino]propyl}phenyl)-N-(2-chlorobenzyl)propionamide

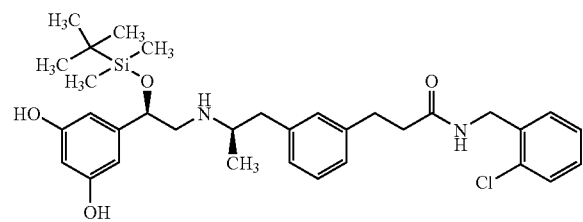

Prepared according to the procedure used for preparation 34, using PREPARATION 141, 2-chlorobenzylamine and N,N-dimethylacetamide replacing N,N-dimethylformamide.

¹H NMR (400 MHz, CD₃OD) δ: −0.15 (3H, s), 0.01 (3H, s), 0.84 (9H, s), 1.03 (3H, d), 2.47-2.58 (3H, m), 2.60-2.70 (2H, m), 2.80-2.95 (4H, m), 4.41 (2H, m), 4.59 (1H, m), 6.16 (1H, m), 6.24 (2H, s), 6.95 (2H, m), 7.02-7.08 (2H, m), 7.13-7.25 (3H, m), 7.36 (1H, m); LRMS APCl m/z 598 [M+H]⁺

PREPARATION 143

3-(3-{2-[2-(tert-Butyldimethylsilanyloxy)-2-(3,5-dihydroxyphenyl) ethylamino]propyl}phenyl)-N-(2,6-dichlorobenzyl)propionamide

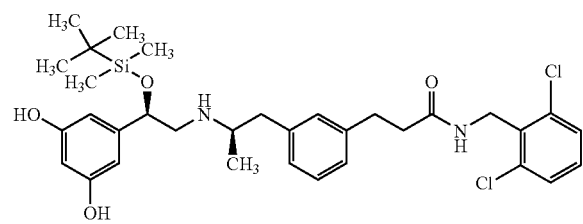

Prepared according to the procedure used for preparation 34, using Preparation 141, 2,6-dichlorobenzylamine and N,N-dimethylacetamide replacing N,N-dimethylformamide.

¹H NMR (400 MHz, CD₃OD) δ: −0.15 (3H, s), 0.00 (3H, s), 0.85 (9H, s), 1.03 (3H, d), 2.44-2.57 (3H, m), 2.60-2.68 (2H, m), 2.80-2.90 (4H, m), 4.55-4.65 (3H, m), 6.16 (1H, m), 6.24 (2H, s), 6.91 (1H, m), 6.94 (1H, m), 7.01 (1H, m), 7.12 (1H, m), 7.26 (1H, m), 7.37-7.41 (2H, m); LRMS APCl m/z 631 [M+H]⁺

PREPARATION 144

3-(3-{2-[2-(tert-Butyldimethylsilanyloxy)-2-(3,5-dihydroxy-phenyl)ethylamino]propyl}phenyl)-1-(3,4-dihydro-1H-isoquinolin-2-yl)-propan-1-one

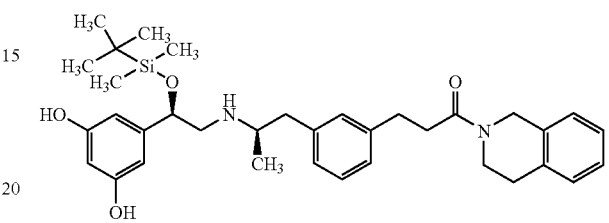

Prepared according to the procedure used for preparation 34, using Preparation 141, 1,2,3,4-tetrahydroisoquinoline and N,N-dimethylacetamide replacing N,N-dimethylformamide.

¹H NMR (400 MHz, CD₃OD) δ: −0.15 (3H, s), −0.01 (3H, s), 0.85 (9H, s), 0.99 (3H, m), 2.42-2.64 (3H, m), 2.68-2.96 (8H, m), 3.63-3.76 (2H, m), 4.55-4.67 (3H, m), 6.16 (1H, m), 6.23 (2H, s), 6.81-7.21 (8H, m); LRMS APCl m/z 590 [M+H]⁺

PREPARATION 145

2-(3-{2-[2-(tert-Butyldimethylsilanyloxy)-2-(3,5-dihydroxy-phenyl)ethylamino]propyl}phenyl)-N-(2-chloro-4-fluorobenzyl)acetamide

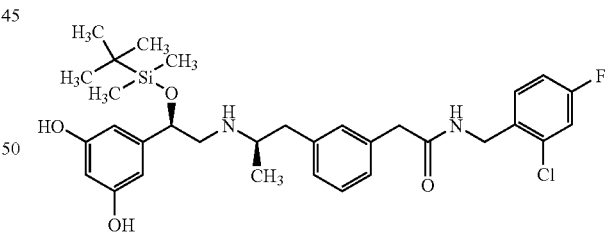

Prepared according to the procedure used for preparations 142, using the acid from Preparation 33 and 2-chloro-4-fluorobenzylamine.

¹H NMR (400 MHz, CD₃OD) δ: −0.02 (3H, d), 0.00 (3H, s), 0.84 (9H, s), 1.04 (3H, d), 2.54-2.70 (3H, m), 2.86-2.93 (2H, m), 3.53 (2H, s), 4.41 (1H, s), 4.46 (1H, s), 4.60-4.63 (1H, m), 6.14-6.15 (1H, m), 6.22 (2H, d), 6.97-7.50 (7H, m), 7.64-7.69 (1H, m); LRMS APCl m/z 601 [M+H]⁺.

PREPARATION 146

N-(4-Bromobenzyl)-2-(3-{2-[2-(tert-butyldimethyl-silanyloxy)-2-(3,5-dihydroxyphenyl)ethylamino]-2-methylpropyl}phenyl)acetamide

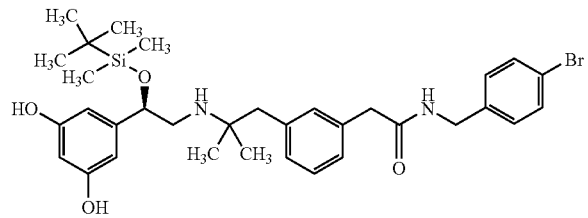

Prepared according to the procedure used for preparations 34, using the acid from Preparation 33 and 4-bromobenzylamine.

$^1$H NMR (400 MHz, CD$_3$OD) δ: −0.23 (s, 3H), −0.04 (s, 3H), 0.82 (s, 9H), 1.07 (d, 6H), 2.63-2.77 (m, 3H), 2.84 (t, 1H), 3.56 (s, 2H), 4.31 (s, 2H), 4.57-4.63 (m, 1H), 6.18 (t, 1H), 6.36 (s, 2H), 7.08 (t, 2H), 7.12-7.18 (m, 3H), 7.21 (t, 1H), 7.42 (d, 2H).; LRMS ESI m/z 643 [M+H]$^+$.

PREPARATION 147

2-(3-{2-[2-(tert-Butyldimethylsilanyloxy)-2-(3,5-dihydroxyphenyl)ethylamino]-2-methylpropyl}phenyl)-N-(3,4-dimethylphenyl)acetamide

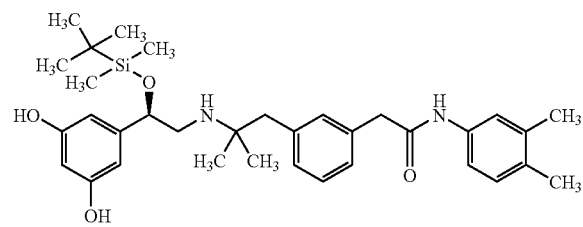

Prepared according to the procedure used for preparations 34, using the acid from Preparation 33 and 3,4-dimethylaniline.

$^1$H NMR (400 MHz, CD$_3$OD) δ: −0.17 (s, 3H), −0.03 (s, 3H), 0.81 (s, 9H), 1.07 (d, 6H), 2.22 (d, 6H), 2.61-2.77 (m, 3H), 2.83 (t, 1H), 3.61 (s, 2H), 4.57-4.61 (m, 1H), 6.18 (s, 1H), 6.29 (s, 2H), 7.06 (t, 2H), 7.18 (s, 1H), 7.21-7.25 (m, 3H), 7.31 (s, 1H); LRMS ESI m/z 643 [M+H]$^+$.

PREPARATION 148

2-(3-{2-[2-(tert-Butyldimethylsilanyloxy)-2-(3,5-dihydroxyphenyl)ethylamino]propyl}phenyl)-N-(2,3-dimethylbenzyl)acetamide

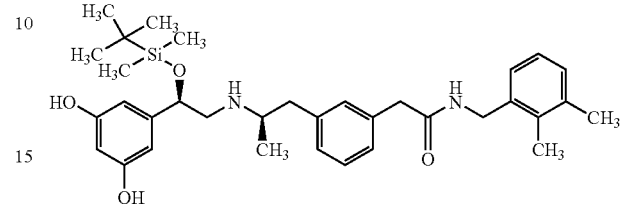

Prepared according to the procedure used for preparations 34, using the acid from Preparation 45 and 2,3-dimethylbenzylamine and N,N-dimethylacetamide replacing N,N-dimethylformamide.

$^1$H NMR (400 MHz, CD$_3$OD) δ: −0.17 (3H, s), −0.04 (3H, s), 0.80 (9H, s), 0.97 (3H, d), 2.09 (3H, s), 2.21 (2.46-2.51 (1H, dd), 2.56-2.65 (2H, m), 2.76-2.84 (2H, m), 3.45 (2H, s), 4.32 (2H, s), 4.53 (1H, dd), 5.44 (2H, s), 6.09 (1H, t), 6.17 (1H, 1), 6.18 (1H, s), 6.93-7.17 (7H, m); LRMS APCl m/z 578 [M+H]$^+$.

PREPARATION 149

2-(3-{2-[2-(tert-Butyldimethylsilanyloxy)-2-(3,5-dihydroxyphenyl) ethylamino]propyl}phenyl)-N-(4-fluorobenzyl)acetamide

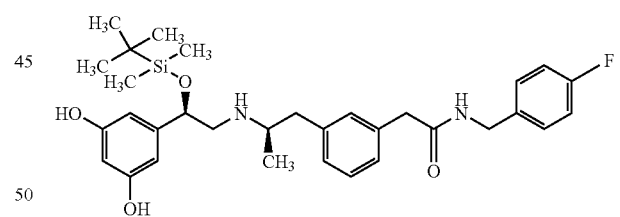

Prepared according to the procedure used for preparations 34, using the acid from Preparation 45 and 4-fluorobenzylamine and N,N-dimethylacetamide replacing N,N-dimethylformamide.

$^1$H NMR (400 MHz, CD$_3$OD) δ: −0.17 (3H, s), −0.04 (3H, s), 0.80 (9H, s), 0.98 (3H, d), 2.47 (1H, dd), 2.55-2.64 (H, m), 2.77-2.84 (2H, m), 3.46 (2H, s), 4.28 (2H, s), 4.53 (1H, dd), 6.09-6.11 (1H, m), 6.17 (1H, s), 6.18 (1H, s), 6.91-7.02 (4H, m), 7.05-7.08 (1H, m), 7.13 (1H, t), 7.17-7.23 (2H, m); LRMS APCl m/z 567 [M+H]$^+$.

PREPARATION 150

2-(3-{2-[2-(tert-Butyldimethylsilanyloxy)-2-(3,5-dihydroxyphenyl)ethylamino]propyl}phenyl)-1-(4-pyridin-2-yl-piperazin-1-yl)ethanone

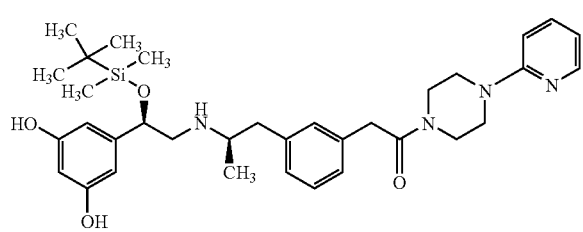

Prepared according to the procedure used for preparations 34, using the acid from Preparation 45 and 1-pyridin-2-ylpiperazine, and N,N-dimethylacetamide replacing N,N-dimethylformamide.

$^1$H NMR (400 MHz, CD$_3$OD) δ: −0.12 (3H, s), 0.00 (3H, s), 0.80 (9H, s), 1.12 (3H, d), 2.66 (1H, dd), 2.88-2.93 (2H, m), 3.04-3.10 (1H, m), 3.15 (1H, dd), 3.32-3.43 (4H, m), 3.60-3.66 (4H, m), 3.73-3.79 (2H, m), 4.81-4.85 (1H, m), 6.18 (1H, t), 6.25 (1H, s), 6.26 (1H, s), 6.60-6.63 (1H, m), 6.72 (1H, d), 7.04-7.07 (2H, m), 7.12 (1H, d), 7.23 (1H, t), 7.46 (1H, dt), 8.00 (1H, d); LRMS APCl m/z 606 [M+H]$^+$d.

PREPARATION 151

2-(3-{2-[2-(tert-Butyldimethylsilanyloxy)-2-(3,5-dihydroxyphenyl) ethylamino]-2-methylpropyl}phenyl)-N-(2-phenylpropyl)acetamide

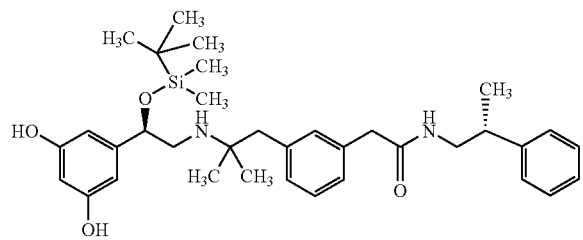

The title compound was prepared from the compound of preparation 33 and the appropriate amine using the method described for preparation 34 and was isolated as a white foam.

$^1$H NMR (400 MHz, CD$_3$OD) δ −0.20 (3H, s), −0.07 (3H, s), 0.74 (9H, s), 1.02 (3H, d), 1.09 (3H, d), 2.62 (1H, dd), 2.79 (1H, dd), 2.88-2.97 (2H, m), 3.04 (1H, dd), 3.16-3.24 (1H, m), 3.27-3.88 (2H, m), 3.41 (2H, s), 4.74 (1H, dd), 6.19 (1H, t), 6.27 (1H, s), 6.28 (1H, s), 7.01-7.07 (2H, m), 7.13-7.27 (4H, m). LRMS APCl m/z 578 [M+H$^+$].

EXAMPLE 1

N-Benzyl-2-[3-(2-{[2-(3,5-dihydroxyphenyl)-2-hydroxyethyl]amino}-2-methylpropyl)phenyl]acetamide

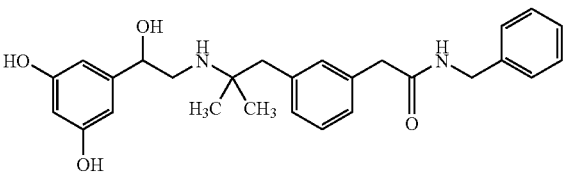

To a solution of the acid of preparation 9 (50 mg, 0.10 mmol) and benzylamine (14 mg, 0.13 mmol) in N,N-dimethylformamide (1 mL) O-(1H-benzotriazol-1-yl)-N,N,N',N'-tetramethyluronium hexafluorophosphate (50 mg, 0.13 mmol) in N,N-dimethylformamide (3 mL) was added and the reaction stirred for 12 hours. The solvent was removed in vacuo to give the crude residue. Purification by column chromatography on silica gel using dichloromethane:methanol: 0.88 ammonia (97.5:2.5:0.25-90:10:1) gave the desired product, 17 mg (37%).

$^1$H NMR (400 MHz, CD$_3$OD) δ 1.02 (3H, s), 1.04 (3H, s), 2.84-2.64 (4H, m), 3.52 (2H, s), 4.35 (2H, s), 4.53-4.57 (1H, q), 6.18 (1H, s), 6.33 (2H, s), 7.02-7.04 (2H, d), 7.12-7.28 (7H, m). LRMS: m/z APCl$^+$ 449 [MH$^+$].

EXAMPLES 2-11

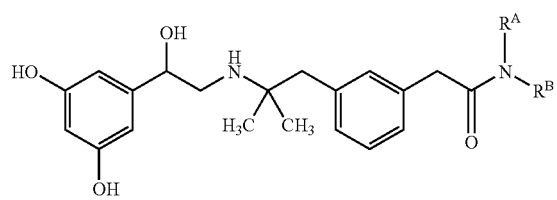

A solution of the acid from preparation 9 (30 µmol) in N,N-dimethylformamide (100 µL) was added to the appropriate amine (HNR$^A$R$^B$) (30 µmol) in N,N-dimethylformamide (100 µL) and the reaction mixture was sealed and shaken. A solution of O-benzotriazol-1-yl-N,N,N',N'-tetramethyluronium hexafluorophosphate (11.38 mg, 30µmol) in N,N-dimethylformamide (200 µL) was added, the reaction mixture sealed and shaken and allowed to stand at room temperature for 4 days. The reaction mixture was purified directly by HPLC using a Phenomenex Luna C18 column (150×10 mm, 10 µm), at a flow rate of 8 mL/min and detection at 225 nm, using the following gradient system.

A-0.05% aqueous diethylamine
B-acetonitrile

| Time (min) | % B |
|---|---|
| 0-0.2 | 5 |
| 0.2-8 | 5-95 |
| 8-9.6 | 95 |

Each product was analysed using a Phenomenex Luna C18 (30×4.6mm, 5 μm) column at a 15 flow rate of 2.5 mL/min using the gradient described in the table below.
A-5% 6.5 mM ammonium acetate in water:acetonitrile (95:5)
B-acetonitrile

| Time (min) | % B |
|---|---|
| 0 | 0 |
| 3 | 95 |
| 3.5 | 95 |

| Example | -NR$^A$R$^B$ | M$^+$ | Retention time (min) |
|---|---|---|---|
| 2 | 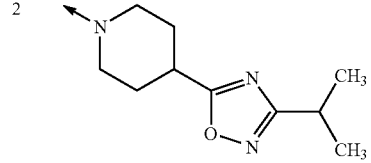 | 536.3 | 1.67 |
| 3 | 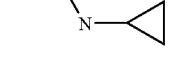 | 398.22 | 1.21 |
| 4 |  | 478.25 | 1.56 |
| 5 | 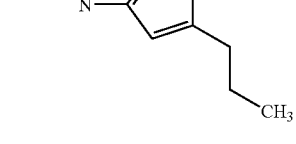 | 466.26 | 1.51 |
| 6 | 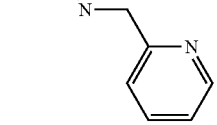 | 449.23 | 1.32 |
| 7 | 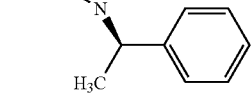 | 462.25 | 1.57 |
| 8 | 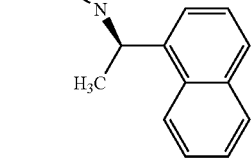 | 512.27 | 1.82 |
| 9 | 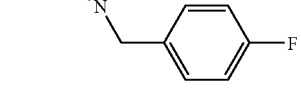 | 466.23 | 1.64 |// -continued
| 10 | 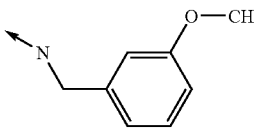 | 478.28 | 1.6 |
| 11 |  | 466.23 | 1.6 |

$^A$= 3-amino-5-ethyl-1H-pyrazole prepared as described in WO 03/048133

EXAMPLE 12

N-[2-(4-Chloro-phenyl)-ethyl]-3-{2-[2-(3,5-dihydroxy-phenyl)-2-hydroxy-ethylamino]-2-methyl-propyl}-benzamide

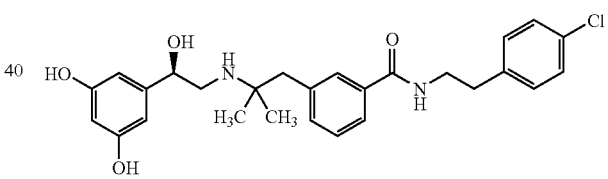

Ammonium fluoride (1.08 g, 29.2 mmol) was added in one portion to a stirred solution of the compound of preparation 15 (1.56 g, 2.61 mmol) in methanol (25 mL) and water (18 mL) at room temperature. The reaction was heated to 40° C. for 48 hours, cooled to room temperature and the solvent removed in vacuo. The residue was purified by column chromatography on silica gel eluting with dichloromethane: methanol:880 ammonia (100:0:0 then 95:5:0.5 then 90:10:1) to furnish the title compound as a brown solid, 885 mg.

$^1$H NMR (400 MHz, CD$_3$OD) δ 1.10 (3H, s), 1.16 (3H, s), 2.75 (6H, m), 3.62 (2H, m), 4.66 (1H, dd), 6.23 (1H, m), 6.40 (1H, s), 6.41 (1H, s), 7.33 (6H, m), 7.67 (2H, m). LRMS: m/z APCl 484 [M+H$^+$].

EXAMPLE 13

N-Adamantan-1-yl-2-(3-{2-[2-(3,5-dihydroxy-phenyl)-2-hydroxy-ethylamino]-propyl}-phenyl)-acetamide

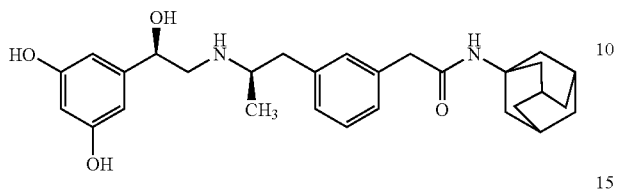

Ammonium fluoride (100 mg, 2.70 mmol) was added in one portion to a stirred solution of the compound of preparation 30 (160 mg, 0.27 mmol) in methanol (2 mL) and water (1 mL) at room temperature. The reaction was heated to 40° C. for 12 hours, cooled to room temperature and the solvent removed in vacuo. The residue was purified by column chromatography on silica gel eluting with dichloromethane:methanol:880 ammonia (93:7:0.7) to furnish the title compound as a white foam, 78 mg.

$^1$H NMR (400 MHz, CD$_3$OD) δ 1.07 (3H, d), 1.68 (6H, s), 2.01 (9H, m), 2.60 (4H, m), 2.91 (1H, m), 3.40 (2H, s), 4.50 (1H, m), 6.13 (1H, m), 6.23 (2H, s), 6.99 (1H, d), 7.08 (1H, s), 7.10 (1H, d), 7.18 (1H, t). LRMS: m/z electrospray 479 [M+H$^+$], 477 [M−H]$^-$.

EXAMPLE 14

3-{2-[2-(3,5-Dihydroxy-phenyl)-2-hydroxy-ethylamino]-2-methyl-propyl}-N-[2-(3-fluoro-phenyl)-ethyl]-benzamide

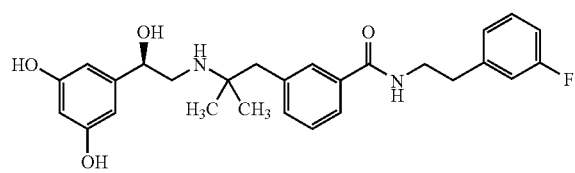

The title compound was prepared from the compound of preparation 36 using the method described for example 12 and was isolated as a white solid.

$^1$H NMR (400 MHz, CD$_3$OD) δ 1.11 (3H, s), 1.15 (3H, s), 2.74-2.82 (2H, m), 2.90-3.00 (4H, m), 3.62-3.66 (2H, m), 4.61-4.66 (1H, m), 6.23-6.24 (1H, m), 6.39 (1H, s), 6.40 (1H, s), 6.94-6.98 (1H, m), 7.03-7.07 (1H, m), 7.10-7.12 (1H, m), 7.29-7.43 (3H, m), 7.65-7.69 (2H, m). LRMS: m/z APCl 467 [M+H$^+$].

EXAMPLE 15

N-[2-(2-Chloro-phenyl)-ethyl]-3-{2-[2-(3,5-dihydroxy-phenyl)-2-hydroxy-ethylamino]-2-methyl-propyl}-benzamide

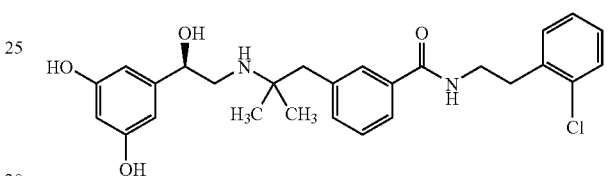

The title compound was prepared from the compound of preparation 37 using the method described for example 12 and was isolated as a white solid.

$^1$H NMR (400 MHz, CD$_3$OD) δ 1.10 (3H, s), 1.15 (3H, s), 2.76-2.84 (2H, m), 2.88-2.96 (2H, m), 3.10-3.14 (2H, m), 3.66-3.70 (2H, m), 4.61-4.64 (1H, m), 6.22-6.24 (1H, m), 6.39 (1H, s), 6.40 (1H, s), 7.21-7.28 (2H, m), 7.35-7.42 (4H, m), 7.66-7.69 (2H, m). LRMS: m/z APCl 483 [M+H$^+$].

EXAMPLE 16

3-{2-[2-(3,5-Dihydroxy-phenyl)-2-hydroxy-ethylamino]-2-methyl-propyl}-N-[2-(2,3-dimethyl-phenyl)-ethyl]-benzamide

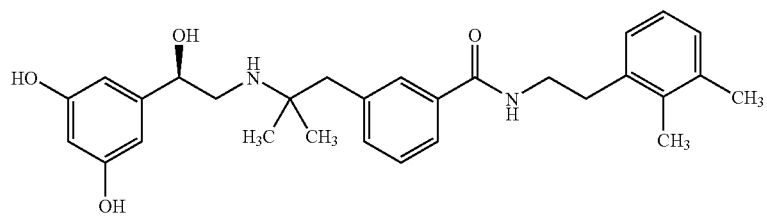

The title compound was prepared from the compound of preparation 38 using the method described for example 12 and was isolated as a white solid.

¹H NMR (400 MHz, CD₃OD) δ 1.14 (3H, s), 1.19 (3H, s), 2.30 (3H, s), 2.31 (3H, s), 2.80-3.02 (6H, m), 3.56-3.59 (2H, m), 4.63-4.67 (1H, m), 6.24-6.25 (1H, m), 6.40 (1H, s), 6.41 (1H, s), 6.99-7.07 (3H, m), 7.38-7.45 (2H, m), 7.68-7.72 (2H, m). LRMS: m/z APCl 477 [M+H⁺].

EXAMPLE 17

N-[2-(2-Chloro-4-fluoro-phenyl)-ethyl]-3-{2-[2-(3,5-dihydroxy-phenyl)-2-hydroxy-ethylamino]-2-methyl-propyl}-benzamide

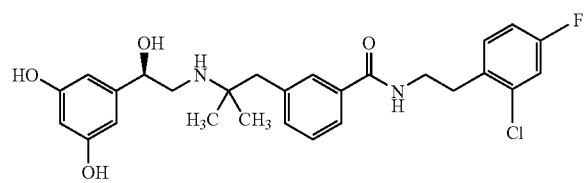

The title compound was prepared from the compound of preparation 39 using the method described for example 12 and was isolated as a white solid.

¹H NMR (400 MHz, CD₃OD) δ 1.09 (3H, s), 1.15 (3H, s), 2.75-2.83 (2H, m), 2.88-2.96 (2H, m), 3.08-3.11 (2H, m), 3.64-3.68 (2H, m), 4.61-4.64 (1H, m), 6.22-6.23 (1H, m), 6.39 (1H, s), 6.40 (1H, s), 7.01-7.06 (1H, m), 7.21-7.24 (1H, m), 7.35-7.42 (3H, m), 7.65-7.68 (2H, m). LRMS: m/z APCl 501 [M+H⁺].

EXAMPLE 18

3-{2-[2-(3,5-Dihydroxy-phenyl)-2-hydroxy-ethylamino]-2-methyl-propyl}-N-[2-(4-methoxy-2,3-dimethyl-phenyl)-ethyl]-benzamide

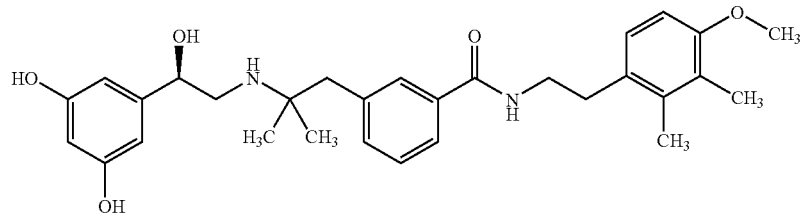

The title compound was prepared from the compound of preparation 40 using the method described for example 12 and was isolated as a white solid.

¹H NMR (400 MHz, CD₃OD) δ 1.12 (3H, s), 1.18 (3H, s), 2.16 (3H, s), 2.30 (3H, s), 2.77-3.00 (6H, m), 3.52-3.56 (2H, m), 3.80 (3H, s), 4.62-4.65 (1H, m), 6.23-6.24 (1H, m), 6.40 (1H, s), 6.41 (1H, s), 6.72-6.74 (1H, d), 7.01-7.03 (1H, d), 7.37-7.44 (2H, m), 7.67 (1H, s), 7.70-7.72 (1H, m). LRMS: m/z APCl 507 [M+H⁺].

EXAMPLE 19

N-(3,4-Dichloro-benzyl)-2-(3-{2-[2-(3,5-dihydroxy-phenyl)-2-hydroxy-ethylamino]-2-methyl-propyl}-phenyl)-acetamide

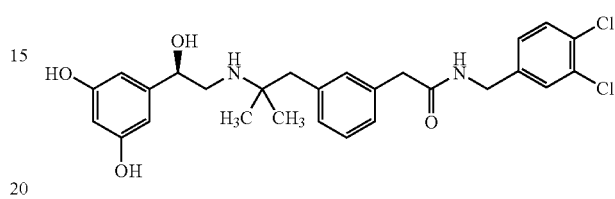

The title compound was prepared from the compound of preparation 34 using the method described for example 12 and was isolated as a white foam.

¹H NMR (400 MHz, CD₃OD) δ 1.02 (3H, s), 1.04 (3H, s), 2.74 (4H, m), 3.56 (2H, s), 4.32 (2H, s), 4.54 (1H, m), 6.17 (1H, s), 6.36 (2H, s), 7.03 (1H, d), 7.15 (3H, m), 7.22 (1H, t), 7.36 (1H, d), 7.43 (1H, d). LRMS: m/z electrospray 517 [M+H⁺].

EXAMPLE 20

N-(3,4-Dichloro-benzyl)-3-{2-[2-(3,5-dihydroxy-phenyl)-2-hydroxy-ethylamino]-2-methyl-propyl}-benzamide

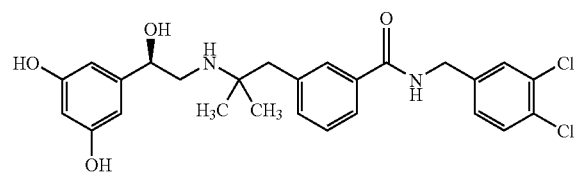

The title compound was prepared from the compound of preparation 41 using the method described for example 12 and was isolated as a white solid.

¹H NMR (400 MHz, CD₃OD) δ 1.16 (3H, s), 1.20 (3H, s), 2.83-3.01 (4H, m), 4.59 (2H, s), 4.64-4.67 (1H, m), 6.23 (1H, m), 6.38 (1H, s), 6.39 (1H, s), 7.31-7.34 (1H, m), 7.41-7.55 (4H, s), 7.76-7.80 (2H, s). LRMS: m/z APCl 503 [M+H⁺].

EXAMPLE 21

N-(4-Chloro-benzyl)-3-{2-[2-(3,5-dihydroxy-phenyl)-2-hydroxy-ethylamino]-2-methyl-propyl}-benzamide

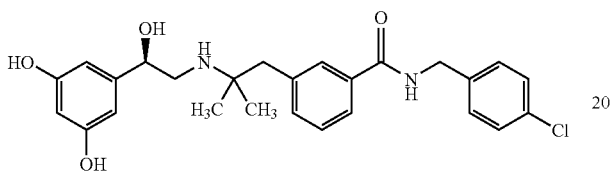

The title compound was prepared from the compound of preparation 42 using the method described for example 12 and was isolated as a white solid.

$^1$H NMR (400 MHz, CD$_3$OD) δ 1.10 (3H, s), 1.15 (3H, s), 2.76-2.82 (2H, m), 2.90-2.96 (2H, m), 4.59 (2H, s), 4.60-4.63 (1H, m), 6.23 (1H, m), 6.37 (1H, s), 6.38 (1H, s), 7.34-7.45 (6H, m), 7.74-7.77 (2H, m). LRMS: m/z APCl 469 [M+H$^+$].

EXAMPLE 22

N-Adamantan-1-yl-3-{2-[2-(3,5-dihydroxy-phenyl)-2-hydroxy-ethylamino]-2-methyl-propyl}-benzamide

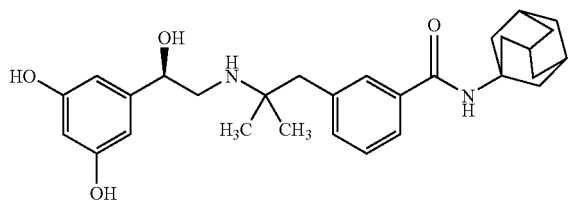

The title compound was prepared from the compound of preparation 43 using the method described for example 12 and was isolated as a white solid.

$^1$H NMR (400 MHz, CD$_3$OD) δ 1.27 (3H, s), 1.28 (3H, s), 1.79-1.81 (6H, m), 2.14 (3H, m), 2.21-2.22 (6H, m), 2.95-3.09 (4H, m), 4.71-4.74 (1H, m), 6.26 (1H, m), 6.42 (1H, s), 6.42 (1H, s), 7.40-7.46 (2H, m), 7.65 (1H, s), 7.68-7.70 (1H, m). LRMS: m/z APCl 480 [M+H$^+$].

EXAMPLE 23

N-(4-Chloro-benzyl)-2-(3-{2-[2-(3,5-dihydroxy-phenyl)-2-hydroxy-ethylamino]-2-methyl-propyl}-phenyl)-acetamide

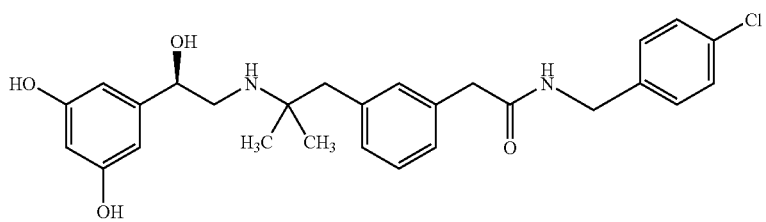

The title compound was prepared from the compound of preparation 46 using the method described for example 12 and was isolated as a white foam.

$^1$H NMR (400 MHz, CD$_3$OD) δ 1.01 (3H, s), 1.04 (3H, s), 2.74 (4H, m), 3.53 (2H, s), 4.34 (2H, s), 4.54 (1H, m), 6.18 (1H, s), 6.34 (2H, s), 7.03 (1H, d), 7.11 (1H, s), 7.20 (6H, m). LRMS: m/z electrospray 483 [M+H$^+$].

EXAMPLE 24

N-(4-Trifluoromethoxybenzyl)-2-(3-{2-[2-(3,5-dihydroxy-phenyl)-2-hydroxy-ethylamino]-2-methyl-propyl}-phenyl)-acetamide

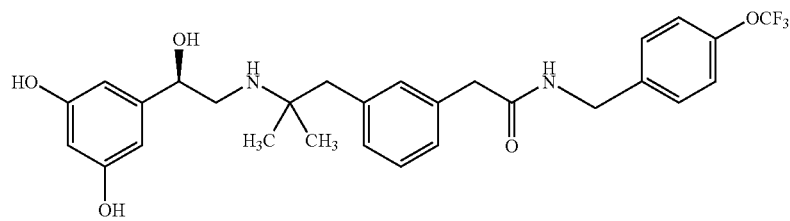

The title compound was prepared from the compound of preparation 47 using the method described for example 12 and was isolated as a white foam.

$^1$H NMR (400 MHz, CD$_3$OD) δ 1.01 (3H, s), 1.03 (3H, s), 2.74 (4H, m), 3.53 (2H, s), 4.37 (2H, s), 4.54 (1H, m), 6.18 (1H, s), 6.34 (2H, s), 7.03 (1H, d), 7.20 (7H, m). LRMS: m/z electrospray 533 [M+H$^+$].

EXAMPLE 25

2-(3-{2-[2-(3,5-Dihydroxy-phenyl)-2-hydroxy-ethylamino]-2-methyl-propyl}-phenyl)-N-pyridin-2-ylmethyl-acetamide

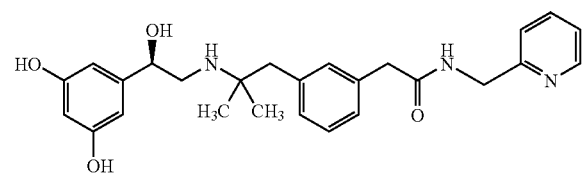

The title compound was prepared from the compound of preparation 48 using the method described for example 12 and was isolated as a white foam.

$^1$H NMR (400 MHz, CD$_3$OD) δ 1.01 (3H, s), 1.03 (3H, s), 2.74 (4H, m), 3.59 (2H, s), 4.45 (2H, s), 4.54 (1H, m), 6.16 (1H, s), 6.35 (2H, s), 7.05 (1H, d), 7.20 (5H, m), 7.72 (1H, t), 8.42 (1H, d). LRMS: m/z electrospray 450 [M+H$^+$].

EXAMPLE 26

N-(3,4-Dichloro-benzyl)-2-(3-{2-[2-(3,5-dihydroxy-phenyl)-2-hydroxy-ethylamino]-propyl}-phenyl)-acetamide

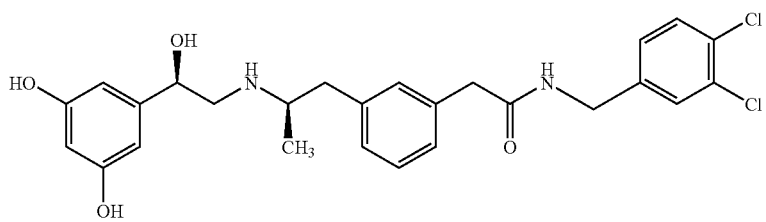

The title compound was prepared from the compound of preparation 49 using the method described for example 12 and was isolated as a white foam.

$^1$H NMR (400 MHz, CD$_3$OD) δ 1.01 (3H, d), 2.58 (1H, m), 2.64 (2H, m), 2.78 (1H, m), 2.90 (1H, m), 3.56 (2H, s), 4.37 (2H, s), 4.54 (1H, m), 6.18 (1H, s), 6.25 (2H, s), 7.03 (5H, m), 7.38 (2H, m). LRMS: m/z electrospray 503 [M+H$^+$].

EXAMPLE 27

N-(Benzyl)-2-(3-{2-[2-(3,5-dihydroxy-phenyl)-2-hydroxy-ethylamino]-propyl}-phenyl)-acetamide

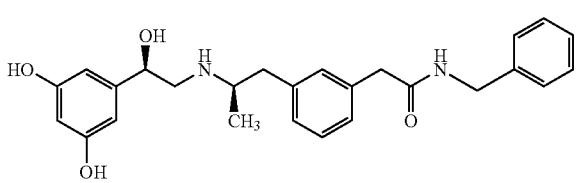

The title compound was prepared from the compound of preparation 50 using the method described for example 12 and was isolated as a brown foam.

$^1$H NMR (400 MHz, CD$_3$OD) δ 1.06 (3H, d), 2.57 (1H, m), 2.68 (2H, m), 2.81 (1H, m), 2.90 (1H, m), 3.53 (2H, s), 4.35

(2H, s), 4.52 (1H, m), 6.16 (1H, m), 6.25 (2H, s), 7.01 (1H, m), 7.08 (1H, s), 7.13 (1H, m), 7.20 (6H, m). LRMS: m/z APCl 435 [M+H⁺], 433 [M−H⁻].

EXAMPLE 28

N-Cyclohexylmethyl-2-(3-{2-[2-(3,5-dihydroxy-phenyl)-2-hydroxy-ethylamino]-propyl}-phenyl)-acetamide

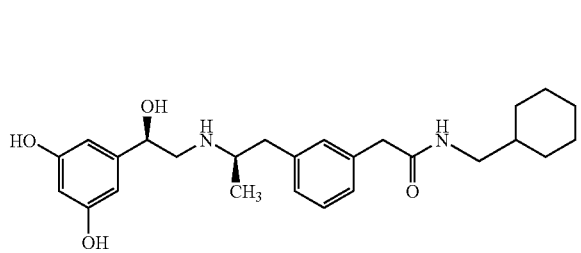

The title compound was prepared from the compound of preparation 51 using the method described for example 12 and was isolated as a brown foam.

¹H NMR (400 MHz, CD₃OD) δ 0.88 (2H, m), 1.06 (3H, d), 1.18 (3H, m), 1.42 (1H, m), 1.68 (5H, m), 2.58 (1H, m), 2.70 (2H, m), 2.81 (1H, m), 2.92 (1H, m), 2.99 (2H, d), 3.46 (2H, s), 4.53 (1H, m), 6.15 (1H, m), 6.25 (2H, s), 7.00 (1H, m), 7.08 (2H, m), 7.19 (1H, m). LRMS: m/z APCl 441 [M+H⁺], 439 [M−H⁻].

EXAMPLE 29

1-(3,4-Dihydro-1H-isoquinolin-2-yl)-2-(3-{2-[2-(3,5-dihydroxy-phenyl)-2-hydroxy-ethylamino]-propyl}-phenyl)-ethanone

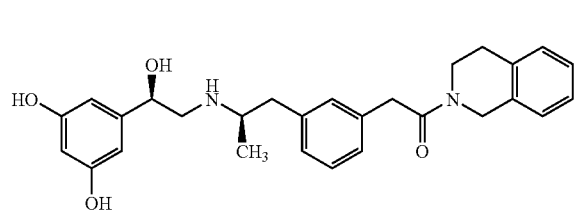

The title compound was prepared from the compound of preparation 52 using the method described for example 12 and was isolated as a brown foam.

¹H NMR (400 MHz, CD₃OD) δ 1.00 (3H, m), 2.57 (7H, m), 3.70 (1H, m), 3.80 (3H, m), 4.50 (1H, m), 4.68 (2H, d), 6.16 (1H, m), 6.26 (2H, s), 7.01 (7H, m). LRMS: m/z APCl 461 [M+H⁺], 459 [M−H⁻].

EXAMPLE 30

N-Benzyl-2-(3-{2-[2-(3,5-dihydroxy-phenyl)-2-hydroxy-ethylamino]-propyl}-phenyl)-N-methyl-acetamide

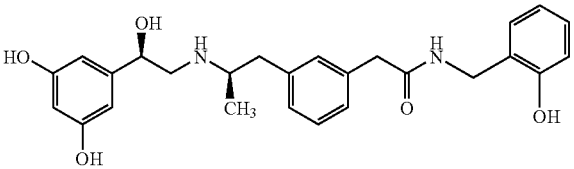

The title compound was prepared from the compound of preparation 53 using the method described for example 12 and was isolated as a brown foam.

¹H NMR (400 MHz, CD₃OD) δ 1.05 (3H, d), 2.62 (3H, m), 2.88 (5H, m), 3.78 (2H, m), 4.50 (1H, m), 4.58 (2H, m), 6.16 (1H, m), 6.26 (2H, s), 7.01 (2H, m), 7.07 (2H, m), 7.20 (5H, m). LRMS: m/z APCl 449 [M+H⁺], 447 [M−H⁻].

EXAMPLE 31

2-(3-{2-[2-(3,5-Dihydroxy-phenyl)-2-hydroxy-ethylamino]-propyl}-phenyl)-N-(2-hydroxy-benzyl)-acetamide The title compound was prepared from the compound of preparation 54 using the method described for example 12 and was isolated as a brown foam.

¹H NMR (400 MHz, CD₃OD) δ 1.05 (3H, d), 2.56 (1H, m), 2.68 (2H, m), 2.81 (2H, m), 3.52 (2H, s), 4.34 (2H, s), 4.53 (1H, m), 6.16 (1H, m), 6.25 (2H, s), 6.76 (2H, m), 7.00 (1H, m), 7.08 (4H, m), 7.18(1H, m). LRMS: m/z APCl 451 [M+H⁺], 449 [M−H⁻].

EXAMPLE 32

N-(4-Cyano-benzyl)-2-(3-{2-[2-(3,5-dihydroxy-phenyl)-2-hydroxy-ethylamino]-2-methyl-propyl}-phenyl)-acetamide

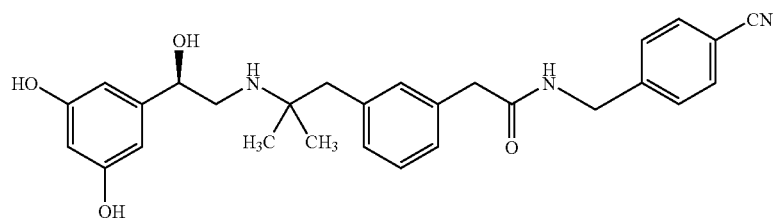

The title compound was prepared from the compound of preparation 55 using the method described for example 12 and was isolated as a white solid.

$^1$H NMR (400 MHz, CD$_3$OD) δ 1.13 (3H, s), 1.15 (3H, s), 2.85 (4H, m), 3.61 (2H, s), 4.47 (2H, s), 4.62 (1H, m), 6.23 (1H, m), 6.38 (2H, s), 7.11 (1H, d), 7.21 (2H, s), 7.28 (1H, m), 7.42 (2H, d), 7.67 (2H, d). LRMS: m/z electrospray 474 [M+H$^+$], 472 [M−H$^-$].

EXAMPLE 33

N-(2,4-Dichloro-benzyl)-2-(3-{2-[2-(3,5-dihydroxyphenyl)-2-hydroxy-ethylamino]-2-methyl-propyl}-phenyl)-acetamide

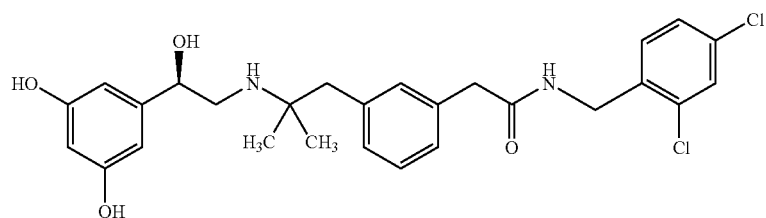

The title compound was prepared from the compound of preparation 56 using the method described for example 12 and was isolated as a white solid.

$^1$H NMR (400 MHz, CD$_3$OD) δ 1.12 (3H, s), 1.13 (3H, s), 2.85 (4H, m), 3.60 (2H, s), 4.46 (2H, s), 4.62 (1H, m), 6.23 (1H, m), 6.38 (2H, s), 7.11 (1H, d), 7.20 (2H, m), 7.28 (3H, m), 7.47 (1H, s). LRMS: m/z electrospray 517 [M+H$^+$], 515 [M−H$^-$].

EXAMPLE 34

N-(Benzyl)-2-(3-{2-[2-(3,5-dihydroxy-phenyl)-2-hydroxy-ethylamino]-2-methyl-propyl}-phenyl)-acetamide

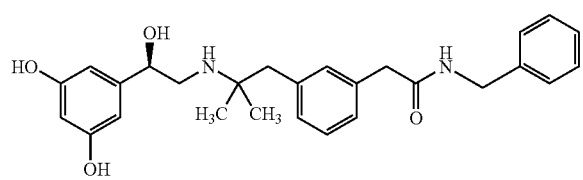

Triethylamine trihydrofluoride (42 uL, 0.25 mmol) was added in one portion to a stirred solution of the compound of preparation 57 (130 mg, 0.23 mmol) in methanol (4 mL) at room temperature. The reaction was stirred for 12 hours and then the pH adjusted to pH 7 using trifluoroacetic acid. The solvent was removed in vacuo and the residue purified by column chromatography on silica gel eluting with dichloromethane:methanol:880 ammonia (95:5:0.5 then 90:10:1) to furnish the title compound as a white foam, 80 mg.

$^1$H NMR (400 MHz, CD$_3$OD) δ 1.09 (3H, s), 1.10 (3H, s), 2.79 (4H, m), 3.53 (2H, s), 4.37 (2H, s), 4.55 (1H, m), 6.18 (1H, t), 6.33 (2H, s), 7.04 (1H, d), 7.13 (1H, s), 7.16 (1H, d), 7.25 (6H, m). LRMS: m/z electrospray 449 [M+H$^+$].

EXAMPLE 35

N-(2-Chlorobenzyl)-2-(3-{2-[2-(3,5-dihydroxy-phenyl)-2-hydroxy-ethylamino]-2-methyl-propyl}-phenyl)-acetamide

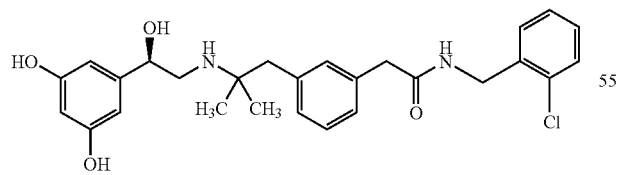

The title compound was prepared from the compound of preparation 58 using the method described for example 34 and was isolated as a white foam.

$^1$H NMR (400 MHz, CD$_3$OD) δ 1.06 (3H, s), 1.08 (3H, s), 2.70 (3H, m), 2.83 (1H, m), 3.57 (2H, s), 4.43 (2H, s), 4.56 (1H, m), 6.18 (1H, s), 6.34 (2H, s), 7.04 (1H, d), 7.18 (6H, m), 7.17 (1H, d). LRMS: m/z electrospray 483 [M+H$^+$].

EXAMPLE 36

N-(3-Methoxybenzyl)-2-(3-{2-[2-(3,5-dihydroxy-phenyl)-2-hydroxy-ethylamino]-2-methyl-propyl}-phenyl)-acetamide

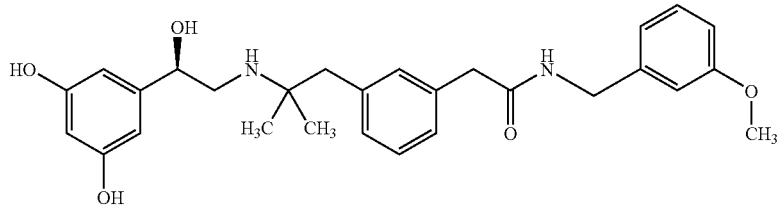

The title compound was prepared from the compound of preparation 59 using the method described for example 34 and was isolated as a white foam.

$^1$H NMR (400 MHz, CD$_3$OD) δ 1.06 (3H, s), 1.08 (3H, s), 2.72 (4H, m), 3.53 (2H, s), 3.68 (3H, s), 4.33 (2H, s), 4.56 (1H, m), 6.18 (1H, m), 6.32 (2H, s), 6.78 (2H, m), 7.03 (1H, d), 7.18 (5H, m). LRMS: m/z electrospray 479 [M+H$^+$].

EXAMPLE 37

N-(Cyclohexylmethyl)-2-(3-{2-[2-(3,5-dihydroxy-phenyl)-2-hydroxy-ethylamino]-2-methyl-propyl}-phenyl)-acetamide

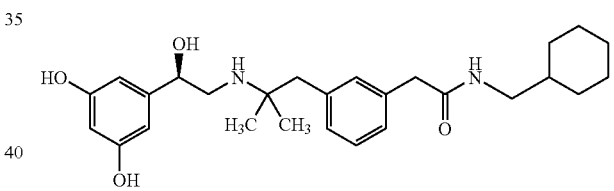

The title compound was prepared from the compound of preparation 60 using the method described for example 34 and was isolated as a white foam.

$^1$H NMR (400 MHz, CD$_3$OD) δ 0.91 (2H, m), 1.06 (3H, s), 1.08 (3H, s), 1.18 (3H, m), 1.44 (1H, m), 1.70 (5H, m), 2.70 (3H, m), 2.84 (1H, m), 3.02 (2H, d), 3.46 (2H, s), 4.58 (1H, m), 6.17 (1H, t), 6.34 (2H, s), 7.07 (1H, d), 7.17 (2H, d), 7.22 (1H, t). LRMS: m/z APCl 455 [M+H$^+$].

EXAMPLE 38

2-(3-{2-[2-(3,5-Dihydroxy-phenyl)-2-hydroxy-ethylamino]-2-methyl-propyl}-phenyl)-N-phenethyl-acetamide

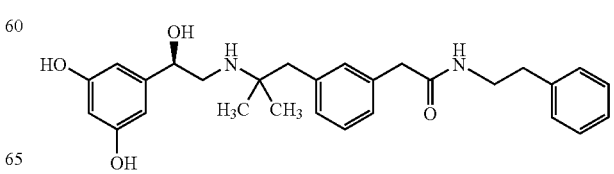

The title compound was prepared from the compound of preparation 61 using the method described for example 34 and was isolated as a white foam.

$^1$H NMR (400 MHz, CD$_3$OD) δ 1.07 (3H, s), 1.08 (3H, s), 2.73 (6H, m), 3.42 (2H, m), 3.47 (2H, s), 4.55 (1H, m), 6.17 (1H, s), 6.33 (2H, s), 7.15 (8H, m). LRMS: m/z electrospray 463 [M+H$^+$], 461 [M–H$^-$].

EXAMPLE 39

2-(3-{2-[2-(3,5-Dihydroxy-phenyl)-2-hydroxy-ethylamino]-2-methyl-propyl}-phenyl)-N-(4-chlorophenethyl)-acetamide

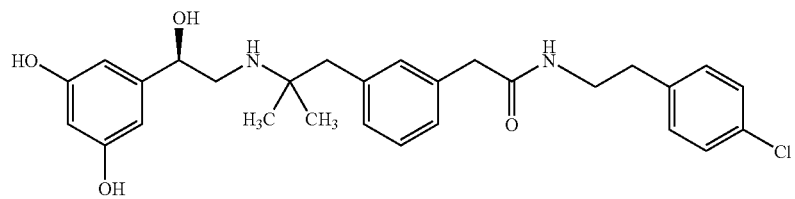

The title compound was prepared from the compound of preparation 62 using the method described for example 34 and was isolated as a white foam.

$^1$H NMR (400 MHz, CD$_3$OD) δ 1.07 (3H, s), 1.08 (3H, s), 2.73 (6H, m), 3.43 (2H, m), 3.42 (2H, s), 4.55 (1H, m), 6.17 (1H, s), 6.36 (2H, s), 7.08 (5H, m), 7.21 (3H, m). LRMS: m/z electrospray 497 [M+H$^+$], 495 [M–H$^-$].

EXAMPLE 40

2-(3-{2-[2-(3,5-Dihydroxy-phenyl)-2-hydroxy-ethylamino]-2-methyl-propyl}-phenyl)-N-(4-phenylphenethyl)-acetamide

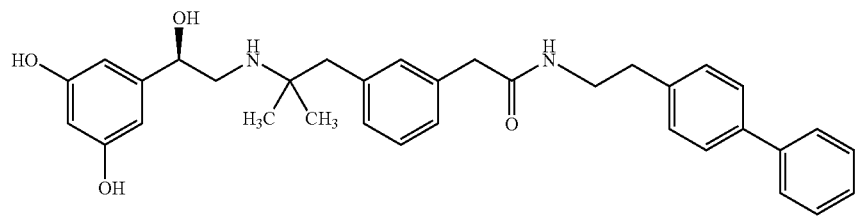

The title compound was prepared from the compound of preparation 63 using the method described for example 34 and was isolated as a white foam.

$^1$H NMR (400 MHz, CD$_3$OD) δ 1.04 (3H, s), 1.05 (3H, s), 2.73 (6H, m), 3.43 (4H, m), 4.55 (1H, m), 6.18 (1H, m), 6.33 (2H, s), 7.08 (3H, m), 7.21 (3H, m), 7.31 (1H, t), 7.42 (2H, m), 7.51 (2H, d), 7.56 (2H, d). LRMS: m/z electrospray 540 [M+H$^+$].

EXAMPLE 41

2-(3-{2-[2-(3,5-Dihydroxy-phenyl)-2-hydroxy-ethylamino]-2-methyl-propyl}-phenyl)-N-(4'-hydroxy-biphenyl-3-ylmethyl)-acetamide

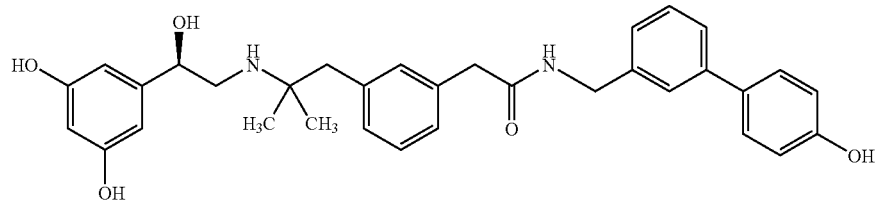

The title compound was prepared from the compound of preparation 64 using the method described for example 34 and was isolated as a white foam.

$^1$H NMR (400 MHz, CD$_3$OD) δ 1.07 (3H, s), 1.08 (3H, s), 2.73 (2H, m), 2.85 (2H, m), 3.57 (2H, s), 4.42 (2H, s), 4.58 (1H, m), 6.19 (1H, m), 6.33 (2H, s), 6.83 (2H, d), 7.07 (1H, d), 7.13 (2H, d), 7.23 (2H, m), 7.38 (5H, m). LRMS: m/z electrospray 541 [M+H$^+$], 539 [M−H$^-$].

EXAMPLE 42

N-Cycloheptyl-2-(3-{2-[2-(3,5-dihydroxy-phenyl)-2-hydroxy-ethylamino]-2-methyl-propyl}-phenyl)-acetamide

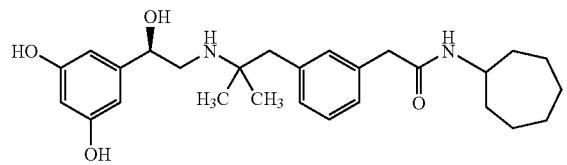

The title compound was prepared from the compound of preparation 65 using the method described for example 34 and was isolated as a white foam.

$^1$H NMR (400 MHz, CD$_3$OD) δ 1.07 (3H, s), 1.08 (3H, s), 1.58 (10H, m), 1.86 (2H, m), 2.73 (4H, m), 3.44 (2H, s), 3.80 (1H, m), 4.58 (1H, m), 6.18 (1H, m), 6.32 (2H, s), 7.05 (1H, d), 7.15 (2H, d), 7.23 (1H, t). LRMS: m/z electrospray 455 [M+H$^+$], 453 [M−H$^-$].

EXAMPLE 43

2-(3-{2-[2-(3,5-Dihydroxy-phenyl)-2-hydroxy-ethylamino]-propyl}-phenyl)-N-phenethyl-acetamide

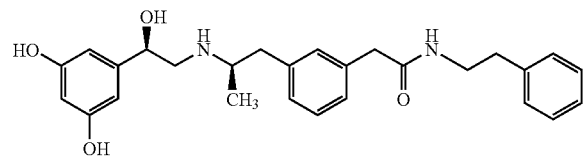

The title compound was prepared from the compound of preparation 66 using the method described for example 12 and was isolated as a white foam.

$^1$H NMR (400 MHz, CD$_3$OD) δ 1.05 (3H, d), 2.78 (7H, m), 3.40 (4H, m), 4.52 (1H, m), 6.13 (1H, m), 6.24 (2H, s), 7.08 (9H, m). LRMS: m/z APCl 447 [M−H$^-$].

EXAMPLE 44

2-(3-{2-[2-(3,5-Dihydroxy-phenyl)-2-hydroxy-ethylamino]-propyl}-phenyl)-N-(2-methylsulfanyl-benzyl)-acetamide

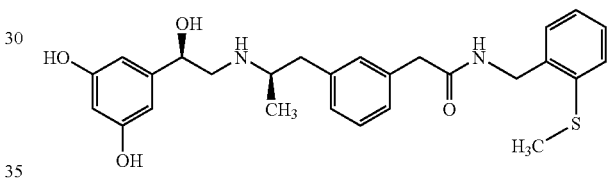

The title compound was prepared from the compound of preparation 67 using the method described for example 12 and was isolated as a white foam.

$^1$H NMR (400 MHz, CD$_3$OD) δ 1.05 (3H, d), 2.44 (3H, s), 2.56 (1H, m), 2.75 (4H, m), 3.53 (2H, s), 4.44 (2H, s), 4.52 (1H, m), 6.13 (1H, m), 6.24 (2H, s), 7.10 (8H, m).

EXAMPLE 45

N-(2,6-Dichloro-benzyl)-2-(3-{2-[2-(3,5-dihydroxy-phenyl)-2-hydroxy-ethylamino]-propyl}-phenyl)-acetamide

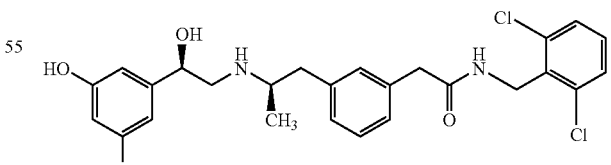

The title compound was prepared from the compound of preparation 68 using the method described for example 12 and was isolated as a white foam.

$^1$H NMR (400 MHz, CD$_3$OD) δ 1.05 (3H, d), 2.54 (1H, m), 2.78 (5H, m), 3.48 (2H, s), 4.52 (1H, m), 4.66 (2H, s), 6.15

(1H, m), 6.25 (2H, s), 7.00 (1H, m), 7.08 (2H, m), 7.18 (1H, m), 7.27 (1H, m), 7.38 (2H, m). LRMS: m/z APCl 503 [M+H⁺].

EXAMPLE 46

2-(3-{2-[2-(3,5-Dihydroxy-phenyl)-2-hydroxy-ethylamino]-propyl}-phenyl)-N-indan-2-yl-acetamide

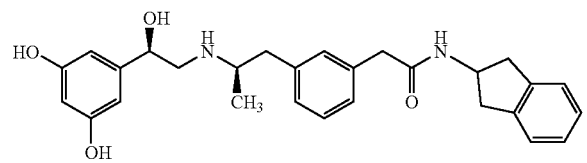

The title compound was prepared from the compound of preparation 69 using the method described for example 12 and was isolated as a white foam.

¹H NMR (400 MHz, CD₃OD) δ 1.05 (3H, d), 2.58 (1H, m), 2.78 (6H, m), 3.22 (2H, m), 3.45 (2H, s), 4.56 (2H, m), 6.15 (1H, m), 6.25 (2H, s), 7.00 (8H, m). LRMS: m/z APCl 461 [M+H⁺].

EXAMPLE 47

N-(2-Chloro-6-fluorobenzyl)-2-(3-{2-[2-(3,5-dihydroxy-phenyl)-2-hydroxy-ethylamino]-propyl}-phenyl)-acetamide

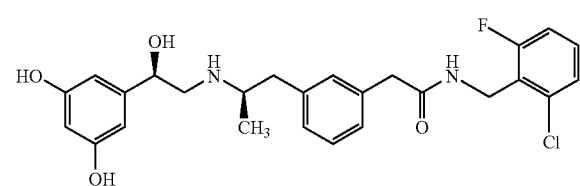

The title compound was prepared from the compound of preparation 70 using the method described for example 12 and was isolated as a white foam.

¹H NMR (400 MHz, CD₃OD) δ 1.05 (3H, d), 2.54 (1H, m), 2.71 (2H, m), 2.83 (2H, m), 3.48 (2H, s), 4.57 (3H, m), 6.15 (1H, s), 6.25 (2H, s), 7.27 (7H, m). LRMS: m/z APCl 487 [M+H⁺], 485 [M–H⁻].

EXAMPLE 49

N-(4-Chlorobenzyl)-2-(3-{2-[2-(3,5-dihydroxy-phenyl)-2-hydroxy-ethylamino]-propyl}-phenyl)-acetamide

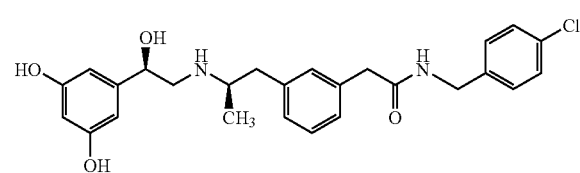

The title compound was prepared from the compound of preparation 72 using the method described for example 12 and was isolated as a white foam.

¹H NMR (400 MHz, CD₃OD) δ 1.05 (3H, d), 2.58 (1H, m), 2.71 (2H, m), 2.83 (1H, m), 2.90 (1H, m), 3.48 (2H, s), 4.38 (2H, s), 4.57 (1H,m), 6.16 (1H, s), 6.25 (2H, s), 7.02 (1H, d), 7.09 (1H, s), 7.11 (1H, m), 7.20 (3H, m), 7.28 (2H, m). LRMS: m/z APCl 469 [M+H⁺], 467 [M–H⁻].

EXAMPLE 50

N-(2,5-Dichloro-benzyl)-2-(3-{2-[2-(3,5-dihydroxy-phenyl)-2-hydroxy-ethylamino]-2-methyl-propyl}-phenyl)-acetamide

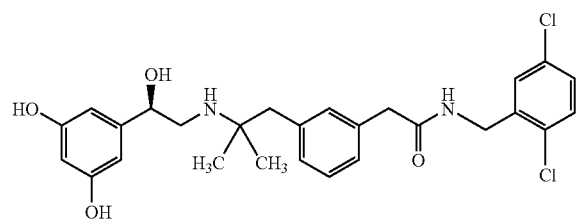

The title compound was prepared from the compound of preparation 73 using the method described for example 12 and was isolated as a white solid.

¹H NMR (400 MHz, CD₃OD) δ 1.12 (3H, s), 1.13 (3H, s), 2.85 (4H, m), 3.62 (2H, s), 4.46 (2H, s), 4.62 (1H, m), 6.23 (1H, m), 6.38 (2H, s), 7.20 (6H, m), 7.39 (1H, d). LRMS: m/z electrospray 517 [M+H⁺], 515 [M–H⁻].

EXAMPLE 51

N-(3,5-Dichloro-benzyl)-2-(3-{2-[2-(3,5-dihydroxy-phenyl)-2-hydroxy-ethylamino]-2-methyl-propyl}-phenyl)-acetamide

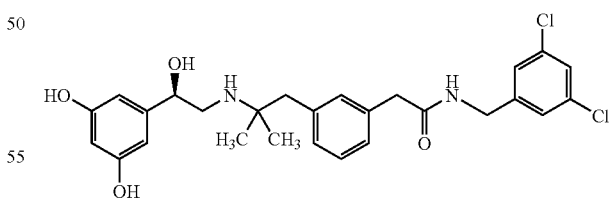

The title compound was prepared from the compound of preparation 74 using the method described for example 12 and was isolated as a white solid.

¹H NMR (400 MHz, CD₃OD) δ 1.11 (3H, s), 1.13 (3H, s), 2.85 (4H, m), 3.59 (2H, s), 4.37 (2H, s), 4.62 (1H, m), 6.23 (1H, m), 6.38 (2H, s), 7.01 (1H, m), 7.12 (1H, m), 7.17 (3H, m), 7.28 (1H, d), 7.32 (1H, m). LRMS: m/z electrospray 517 [M+H⁺], 515 [M–H⁻].

EXAMPLE 52

N-(2,6-Dichloro-benzyl)-2-(3-{2-[2-(3,5-dihydroxy-phenyl)-2-hydroxy-ethylamino]-2-methyl-propyl}-phenyl)-acetamide

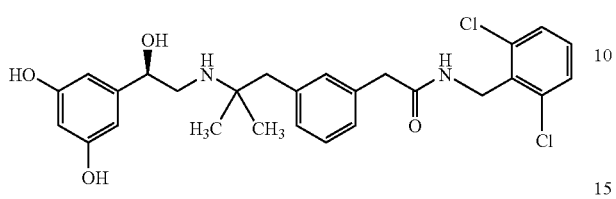

The title compound was prepared from the compound of preparation 75 using the method described for example 12 and was isolated as a white solid.

$^1$H NMR (400 MHz, CD$_3$OD) δ 1.10 (3H, s), 1.11 (3H, s), 2.82 (4H, m), 3.54 (2H, s), 4.60 (1H, m), 4.71 (2H, s), 6.22 (1H, m), 6.38 (2H, s), 7.07 (1H, m), 7.18 (2H, m), 7.26 (1H, m), 7.31 (1H, m), 7.43 (1H, s), 7.45 (1H, m). LRMS: m/z electrospray 520 [M+H$^+$], 518 [M−H$^-$].

EXAMPLE 53

N-Biphenyl-2-ylmethyl-2-(3-{2-[2-(3,5-dihydroxy-phenyl)-2-hydroxy-ethylamino]-2-methyl-propyl}-phenyl)-acetamide

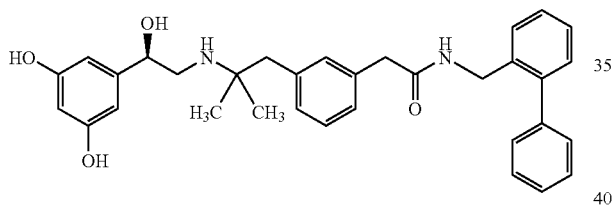

The title compound was prepared from the compound of preparation 76 using the method described for example 12 and was isolated as a white solid.

$^1$H NMR (400 MHz, CD$_3$OD) δ 1.14 (3H, s), 1.15 (3H, s), 2.82 (2H, m), 2.93 (2H, m), 3.52 (2H, s), 4.32 (2H, s), 4.62 (1H, m), 6.23 (1H, m), 6.38 (2H, s), 7.11 (13H, m). LRMS: m/z electrospray 527 [M+H$^+$], 525 [M−H$^-$].

EXAMPLE 54

N-(2-Chlorobenzyl)-2-(3-{2-[2-(3,5-d i hydroxy-phenyl)-2-hydroxy-ethylamino]-propyl}-phenyl)-acetamide

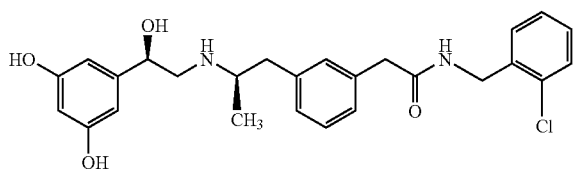

The title compound was prepared from the compound of preparation 77 using the method described for example 12 and was isolated as a white foam.

$^1$H NMR (400 MHz, CD$_3$OD) δ 1.05 (3H, d), 2.56 (1H, m), 2.80 (4H, m), 3.55 (2H, s), 4.45 (2H, s), 4.52 (1H, m), 6.14 (1H, m), 6.25 (2H, s), 7.19 (8H, m). LRMS: m/z APCl 469 [M+H$^+$].

EXAMPLE 55

N-(3-Methoxybenzyl)-2-(3-{2-[2-(3,5-dihydroxy-phenyl)-2-hydroxy-ethylamino]-propyl}-phenyl)-acetamide

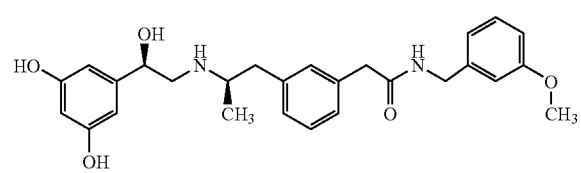

The title compound was prepared from the compound of preparation 78 using the method described for example 12 and was isolated as a white foam.

$^1$H NMR (400 MHz, CD$_3$OD) δ 1.05 (3H, d), 2.60 (5H, m), 3.51 (2H, s), 3.69 (3H, s), 4.32 (2H, s), 4.51 (1H, m), 6.15 (1H, m), 6.25 (2H, s), 6.75 (3H, m), 7.02 (1H, m), 7.21 (4H, m). LRMS: m/z APCl 465 [M+H$^+$].

EXAMPLE 56

N-(3-Trifluoromethylbenzyl)-2-(3-{2-[2-(3,5-dihydroxy-phenyl)-2-hydroxy-ethylamino]-propyl}-phenyl)-acetamide

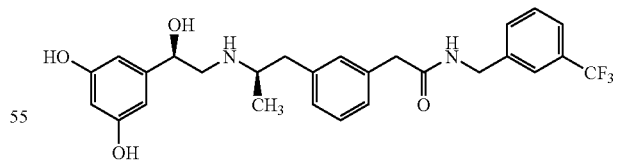

The title compound was prepared from the compound of preparation 79 using the method described for example 12 and was isolated as a pale brown foam.

$^1$H NMR (400 MHz, CD$_3$OD) δ 1.05 (3H, d), 2.57 (1H, m), 2.66 (2H, m), 2.80 (1H, m), 2.90 (1H, m), 3.55 (2H, s), 4.43 (2H, s), 4.51 (1H, m), 6.16 (1H, m), 6.25 (2H, s), 7.03 (1H, m), 7.07 (1H, s), 7.14 (1H, m), 7.21 (1H, m), 7.47 (2H, m), 7.53 (2H, m). LRMS: m/z APCl 503 [M+H$^+$], 501 [M−H$^-$].

EXAMPLE 57

N-(3,4-Difluorobenzyl)-2-(3-{2-[2-(3,5-dihydroxy-phenyl)-2-hydroxy-ethylamino]-propyl}-phenyl)-acetamide

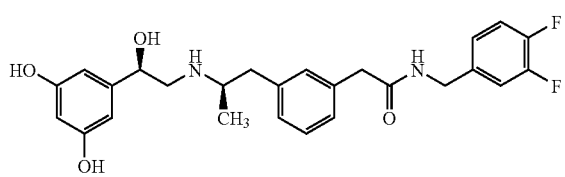

The title compound was prepared from the compound of preparation 80 using the method described for example 12 and was isolated as a pale brown foam.

$^1$H NMR (400 MHz, CD$_3$OD) δ 1.05 (3H, d), 2.58 (1H, m), 2.66 (2H, m), 2.80 (1H, m), 2.90 (1H, m), 3.53 (2H, s), 4.30 (2H, s), 4.52 (1H, m), 6.16 (1H, m), 6.24 (2H, s), 7.01 (2H, m), 7.15 (5H, m). LRMS: m/z APCl 471 [M+H$^+$], 469 [M−H$^−$].

EXAMPLE 58

N-(2-Methoxybenzyl)-2-(3-{2-[2-(3,5-dihydroxy-phenyl)-2-hydroxy-ethylamino]-propyl}-phenyl)-acetamide

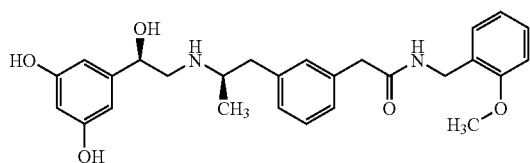

The title compound was prepared from the compound of preparation 81 using the method described for example 12 and was isolated as a pale brown foam.

$^1$H NMR (400 MHz, CD$_3$OD) δ 1.05 (3H, d), 2.57 (1H, m), 2.68 (2H, m), 2.80 (1H, m), 2.87 (1H, m), 3.53 (2H, s), 3.78 (3H, s), 4.35 (2H, s), 4.52 (1H, m), 6.16 (1H, m), 6.23 (2H, s), 6.84 (1H, m), 6.91 (1H, m), 7.01 (1H, m), 7.07 (1H, s), 7.15 (2H, m), 7.21 (2H, m). LRMS: m/z APCl 465 [M+H$^+$], 463 [M−H$^−$].

EXAMPLE 59

N-(3,4-Dimethylbenzyl)-2-(3-{2-[2-(3,5-dihydroxy-phenyl)-2-hydroxy-ethylamino]-propyl}-phenyl)-acetamide

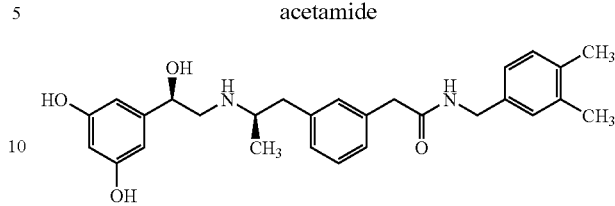

The title compound was prepared from the compound of preparation 82 using the method described for example 12 and was isolated as a pale brown foam.

$^1$H NMR (400 MHz, CD$_3$OD) δ 1.04 (3H, d), 2.19 (3H, s), 2.19 (3H, s), 2.57 (1H, m), 2.66 (2H, m), 2.78 (1H, m), 2.88 (1H, m), 3.49 (2H, s), 4.26 (2H, s), 4.49 (1H, m), 6.16 (1H, m), 6.24 (2H, s), 6.93 (1H, m), 6.97 (1H, s), 7.01 (2H, m), 7.06 (1H, s), 7.13 (1H, m), 7.19 (1H, m). LRMS: m/z APCl 463 [M+H$^+$], 461 [M−H$^−$].

EXAMPLE 60

N-(3,4-Dimethoxybenzyl)-2-(3-{2-[2-(3,5-dihydroxy-phenyl)-2-hydroxy-ethylamino]-propyl}-phenyl)-acetamide

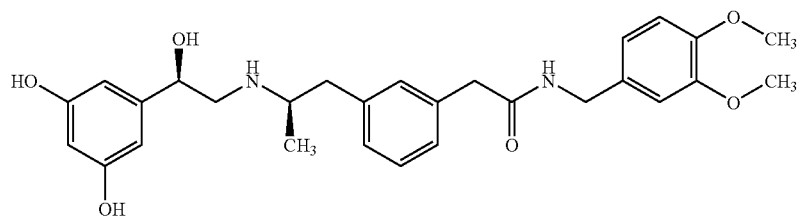

The title compound was prepared from the compound of preparation 83 using the method described for example 12 and was isolated as a pale brown foam.

$^1$H NMR (400 MHz, CD$_3$OD) δ 1.04 (3H, d), 2.57 (1H, m), 2.66 (2H, m), 2.79 (1H, m), 2.88 (1H, m), 3.50 (2H, s), 3.72 (3H, s), 3.78 (3H, s), 4.28 (2H, s), 4.50 (1H, m), 6.16 (1H, m), 6.24 (2H, s), 6.78 (2H, m), 6.85 (1H, m), 7.01 (1H, m), 7.07 (1H, s), 7.14 (1H, m), 7.19 (1H, m). LRMS: m/z APCl 495 [M+H$^+$], 493 [M−H$^−$].

EXAMPLE 61

N-(2-Ethoxybenzyl)-2-(3-{2-[2-(3,5-dihydroxy-phenyl)-2-hydroxy-ethylamino]-propyl}-phenyl)-acetamide

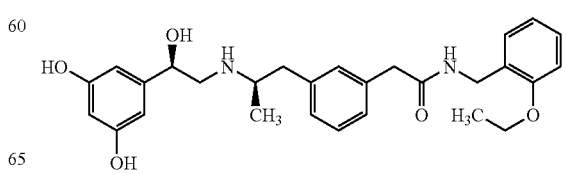

The title compound was prepared from the compound of preparation 84 using the method described for example 12 and was isolated as a pale brown foam.
$^1$H NMR (400 MHz, CD$_3$OD) δ 1.04 (3H, d), 1.35 (3H, t), 2.57 (1H, m), 2.68 (2H, m), 2.80 (1H, m), 2.88 (1H, m), 3.53 (2H, s), 4.00 (2H, q), 4.36 (2H, s), 4.50 (1H, m), 6.15 (1H, m), 6.25 (2H, s), 6.83 (1H, m), 6.88 (1H, m), 7.01 (1H, m), 7.07 (1H, s), 7.15 (2H, m), 7.19 (2H, m). LRMS: m/z APCl 479 [M+H$^+$], 477 [M−H$^−$].

EXAMPLE 62

N-[2-(2-Chloro-phenyl)-ethyl]-2-(3-{2-[2-(3,5-dihydroxy-phenyl)-2-hydroxy-ethylamino]-propyl}-phenyl)-acetamide

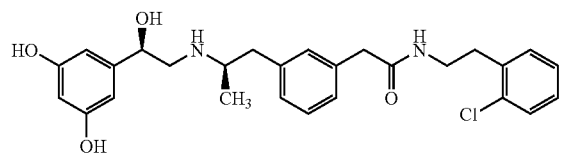

The title compound was prepared from the compound of preparation 85 using the method described for example 12 and was isolated as a pale brown foam.
$^1$H NMR (400 MHz, CD$_3$OD) δ 1.06 (3H, d), 2.58 (1H, m), 2.67 (2H, m), 2.81 (1H, m), 2.88 (3H, m), 3.43 (4H, m), 4.53 (1H, m), 6.16 (1H, m), 6.24 (2H, s), 7.04 (3H, m), 7.20 (6H, m). LRMS: m/z APCl 483 [M+H$^+$], 481 [M−H$^−$].

EXAMPLE 63

4-{[2-(3-{2-[2-(3,5-Dihydroxy-phenyl)-2-hydroxy-ethylamino]-propyl}-phenyl)-acetylamino]-methyl}-benzamide The title compound was prepared from the compound of preparation 86 using the method described for example 12 and was isolated as a white foam.
$^1$H NMR (400 MHz, CD$_3$OD) δ 1.04 (3H, d), 2.57 (1H, m), 2.68 (2H, m), 2.80 (1H, m), 2.87 (1H, m), 3.58 (2H, s), 4.38 (2H, s), 4.51 (1H, m), 6.17 (1H, m), 6.25 (2H, s), 7.01 (1H, d), 7.07 (2H, m), 7.20 (1H, m), 7.29 (2H, d), 7.80 (2H, d). LRMS: m/z APCl 478 [M+H$^+$], 476 [M−H$^−$].

EXAMPLE 64

2-(3-{2-[2-(3,5-Dihydroxy-phenyl)-2-hydroxy-ethylamino]-propyl}-phenyl)-N-indan-1-yl-acetamide

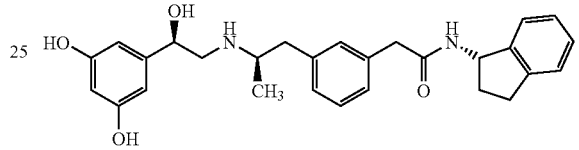

The title compound was prepared from the compound of preparation 87 using the method described for example 12 and was isolated as a pale brown foam.
$^1$H NMR (400 MHz, CD$_3$OD) δ 1.05 (3H, d), 1.81 (1H, m), 2.46 (1H, m), 2.57 (1H, m), 2.72 (2H, m), 2.87 (4H, m), 3.52 (2H, m), 4.53 (1H, m), 5.36 (1H, m), 6.16 (1H, m), 6.25 (2H, s), 7.01 (1H, m), 7.14 (7H, m). LRMS: m/z APCl 461 [M+H$^+$], 459 [M−H$^−$].

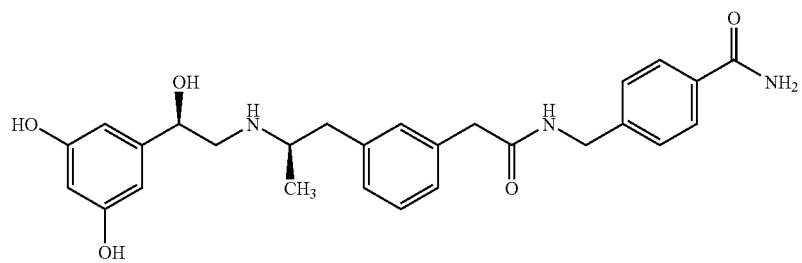

EXAMPLE 65

3-{2-[2-(3,5-Dihydroxy-phenyl)-2-hydroxy-ethylamino]-propyl}-N-[2-(3-fluoro-phenyl)-ethyl]-benzamide

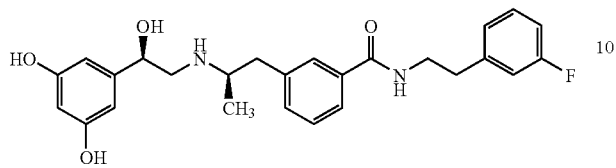

The title compound was prepared from the compound of preparation 94 using the method described for example 12 and was isolated as a white foam.

$^1$H NMR (400 MHz, CD$_3$OD) δ 1.06 (3H, d), 2.80 (7H, m), 3.59 (2H, m), 4.55 (1H, m), 6.15 (1H, m), 6.26 (2H, s), 7.01 (3H, m), 7.30 (3H, m), 7.58 (2H, m). LRMS: m/z APCl 453 [M+H$^+$].

EXAMPLE 66

3-{2-[2-(3,5-Dihydroxy-phenyl)-2-hydroxy-ethylamino]-propyl}-N-[2-(2-chloro-phenyl)-ethyl]-benzamide

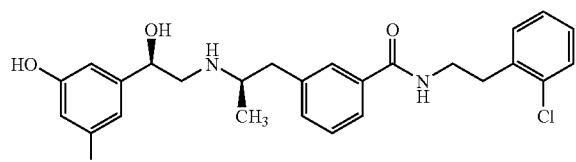

The title compound was prepared from the compound of preparation 95 using the method described for example 12 and was isolated as a white foam.

$^1$H NMR (400 MHz, CD$_3$OD) δ 1.05 (3H, d), 2.81 (5H, m), 3.07 (2H, t), 3.63 (2H, t), 4.53 (1H, m), 6.15 (1H, m), 6.26 (2H, s), 7.20 (6H, m), 7.55 (2H, m). LRMS: m/z APCl 469 [M+H$^+$].

EXAMPLE 67

2-(3-{2-[2-(3,5-Dihydroxy-phenyl)-2-hydroxy-ethylamino]-propyl}-phenyl)-N-naphthalen-1-ylmethyl-acetamide

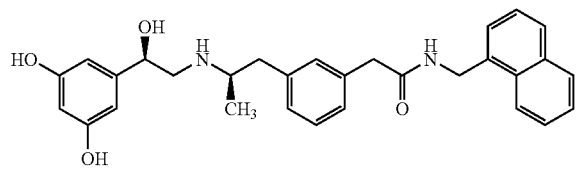

The title compound was prepared from the compound of preparation 96 using the method described for example 12 and was isolated as a white foam.

$^1$H NMR (400 MHz, CD$_3$OD) δ 0.98 (3H, d), 2.47 (1H, m), 2.54 (2H, m), 2.78 (2H, m), 3.54 (2H, s), 4.51 (1H, m), 4.80 (2H, s), 6.17 (1H, s), 6.25 (2H, s), 6.98 (2H, m), 7.07 (2H, m), 7.40 (4H, m), 7.78 (1H, d), 7.84 (1H, d), 7.90 (1H, d). LRMS: m/z APCl 485 [M+H$^+$], 483 [M−H$^-$].

EXAMPLE 68

2-(3-{2-[2-(3,5-Dihydroxy-phenyl)-2-hydroxy-ethylamino]-propyl}-phenyl)-N-(2-fluoro-5-trifluoromethyl-benzyl)-acetamide

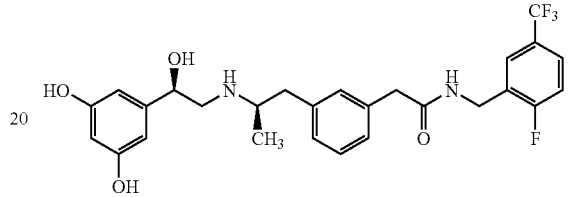

The title compound was prepared from the compound of preparation 97 using the method described for example 12 and was isolated as a white foam.

$^1$H NMR (400 MHz, CD$_3$OD) δ 1.03 (3H, d), 2.47 (1H, m), 2.63 (2H, m), 2.78 (1H, m), 2.89 (1H, m), 3.54 (2H, s), 4.46 (2H, s), 4.58 (1H, m), 6.17 (1H, s), 6.22 (2H, s), 7.01 (1H, d), 7.08 (2H, m), 7.20 (2H, m), 7.58 (2H, m). LRMS: m/z APCl 521 [M+H$^+$], 519 [M−H$^-$].

EXAMPLE 69

2-(3-{2-[2-(3,5-Dihydroxy-phenyl)-2-hydroxy-ethylamino]-propyl}-phenyl)-N-(3-chlorobenzyl)-acetamide

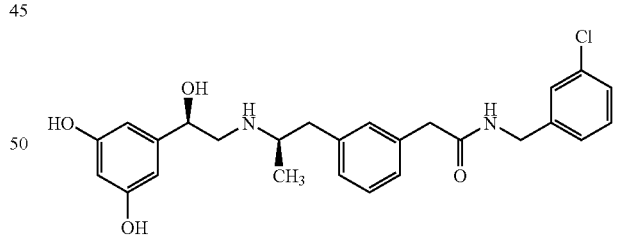

The title compound was prepared from the compound of preparation 98 using the method described for example 12 and was isolated as a white foam.

$^1$H NMR (400 MHz, CD$_3$OD) δ 1.03 (3H, d), 2.58 (1H, m), 2.63 (2H, m), 2.78 (1H, m), 2.85 (1H, m), 3.57 (2H, s), 4.38 (2H, s), 4.52 (1H, m), 6.17 (1H, s), 6.26 (2H, s), 7.01 (1H, d), 7.08 (1H, s), 7.20 (6H, m). LRMS: m/z APCl 469 [M+H$^+$], 467 [M−H$^-$].

EXAMPLE 70

2-(3-{2-[2-(3,5-Dihydroxy-phenyl)-2-hydroxy-ethylamino]-propyl}-phenyl)-N-(4-fluoro-3-trifluoromethyl-benzyl)-acetamide

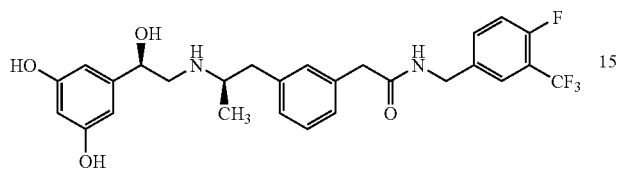

The title compound was prepared from the compound of preparation 99 using the method described for example 12 and was isolated as a white foam.

$^1$H NMR (400 MHz, CD$_3$OD) δ 1.03 (3H, d), 2.58 (1H, m), 2.63 (2H, m), 2.78 (1H, m), 2.89 (1H, m), 3.52 (2H, s), 4.38 (2H, s), 4.52 (1H, m), 6.17 (1H, s), 6.26 (2H, s), 7.03 (1H, d), 7.08 (2H, m), 7.20 (2H, m), 7.51 (2H, m). LRMS: m/z APCl 521 [M+H$^+$], 519 [M−H$^−$].

EXAMPLE 71

2-(3-{2-[2-(3,5-Dihydroxy-phenyl)-2-hydroxy-ethylamino]-2-methyl-propyl}-phenyl)-N-(2-methylsulfanyl-benzyl)-acetamide

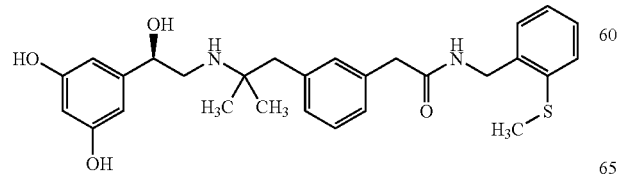

The title compound was prepared from the compound of preparation 100 using the method described for example 12 and was isolated as a white solid.

$^1$H NMR (400 MHz, CD$_3$OD) δ 1.11 (3H, s), 1.12 (3H, s), 2.48 (3H, s), 2.85 (4H, m), 3.59 (2H, s), 4.47 (2H, s), 4.61 (1H, m), 6.23 (1H, m), 6.38 (2H, s), 7.07 (2H, m), 7.26 (6H, m). LRMS: m/z electrospray 497 [M+H$^+$], 494 [M−H$^−$].

EXAMPLE 72

4-{[2-(3-{2-[2-(3,5-Dihydroxy-phenyl)-2-hydroxyethylamino]-2-methyl-propyl}-phenyl)-acetylamino]-methyl}-benzamide

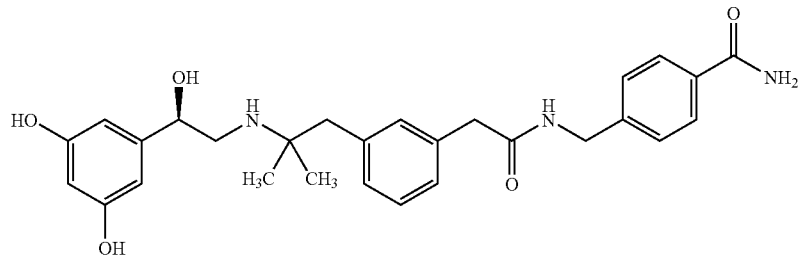

The title compound was prepared from the compound of preparation 101 using the method described for example 12 and was isolated as a white solid.

$^1$H NMR (400 MHz, CD$_3$OD) δ 1.11 (3H, s), 1.12 (3H, s), 2.85 (4H, m), 3.60 (2H, s), 4.46 (2H, s), 4.61 (1H, m), 6.23 (1H, m), 6.38 (2H, s), 7.10 (1H, d), 7.22 (2H, m), 7.28 (1H, m), 7.34 (2H, d), 7.82 (2H, d). LRMS: m/z electrospray 493 [M+H$^+$], 491 [M−H$^−$].

EXAMPLE 73

2-(3-{2-[2-(3,5-Dihydroxy-phenyl)-2-hydroxy-ethylamino]-2-methyl-propyl}-phenyl)-N-(4-sulfamoyl-benzyl)-acetamide

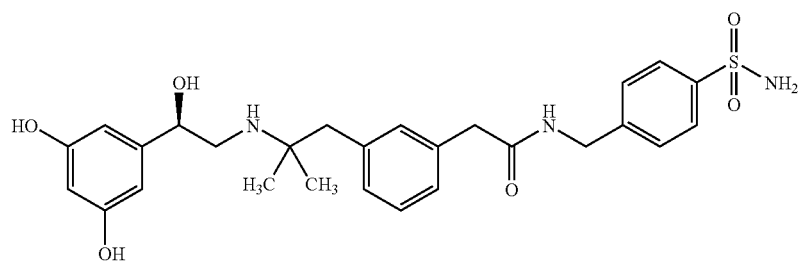

The title compound was prepared from the compound of preparation 102 using the method described for example 12 and was isolated as a white solid.

$^1$H NMR (400 MHz, CD$_3$OD) δ 1.12 (3H, s), 1.13 (3H, s), 2.85 (4H, m), 3.60 (2H, s), 4.47 (2H, s), 4.61 (1H, m), 6.23 (1H, m), 6.38 (2H, s), 7.10 (1H, d), 7.22 (2H, m), 7.28 (1H, m), 7.40 (2H, d), 7.84 (2H, d). LRMS: m/z electrospray 529 [M+H$^+$], 527 [M−H$^-$].

EXAMPLE 74

4-{[2-(3-{2-[2-(3,5-Dihydroxy-phenyl)-2-hydroxy-ethylamino]-2-methyl-propyl}-phenyl)-acetylamino]-methyl}-benzoic acid methyl ester

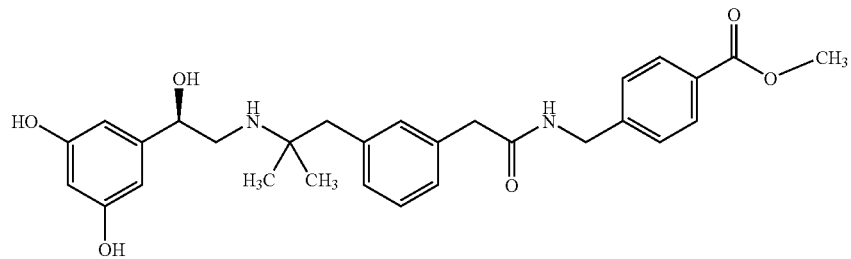

The title compound was prepared from the compound of preparation 103 using the method described for example 12 and was isolated as a white solid.

$^1$H NMR (400 MHz, CD$_3$OD) δ 1.08 (3H, s), 1.10 (3H, s), 2.85 (4H, m), 3.60 (2H, s), 3.92 (3H, s), 4.47 (2H, s), 4.61 (1H, m), 6.22 (1H, m), 6.38 (2H, s), 7.09 (1H, d), 7.20 (2H, m), 7.28 (1H, m), 7.37 (2H, d), 7.95 (2H, d). LRMS: m/z electrospray 508 [M+H$^+$], 506 [M−H$^-$].

EXAMPLE 75

N-(1-Benzyl-piperidin-4-yl)-2-(3-{2-[2-(3,5-dihydroxy-phenyl)-2-hydroxy-ethylamino]-2-methyl-propyl}-phenyl)-acetamide

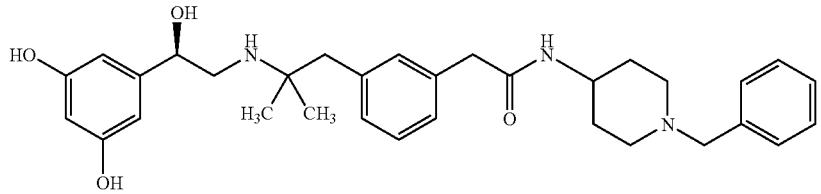

The title compound was prepared from the compound of preparation 104 using the method described for example 12 and was isolated as a white solid.

$^1$H NMR (400 MHz, CD$_3$OD) δ 1.12 (3H, s), 1.13 (3H, s), 1.55 (2H, m), 1.87 (2H, m), 2.15 (2H, m), 2.80 (6H, m), 3.50 (2H, s), 3.55 (2H, s), 3.68 (1H, m), 4.61 (1H, m), 6.22 (1H, m), 6.37 (2H, s), 7.08 (1H, d), 7.18 (2H, m), 7.26 (2H, m), 7.35 (2H, s), 7.36 (2H, s). LRMS: m/z electrospray 533 [M+H$^+$], 531 [M−H$^−$].

EXAMPLE 76

3-{2-[2-(3,5-Dihydroxy-phenyl)-2-hydroxy-ethylamino]-propyl}-N-[2-phenethyl]-benzamide

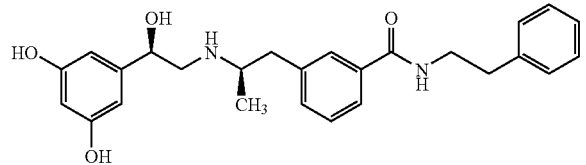

The title compound was prepared from the compound of preparation 105 using the method described for example 12 and was isolated as a white foam.

$^1$H NMR (400 MHz, CD$_3$OD) δ 1.06 (3H, d), 2.62 (1H, m), 2.75 (1H, m), 2.80 (2H, m), 2.94 (3H, m), 3.58 (2H, t), 4.56 (1H, m), 6.16 (1H, m), 6.27 (2H, s), 7.18 (1H, m), 7.26 (6H, m), 7.57 (1H, s), 7.59 (1H, m). LRMS: m/z APCl 435 [M+H$^+$], 433 [M−H$^−$].

EXAMPLE 77

3-{2-[2-(3,5-Dihydroxy-phenyl)-2-hydroxy-ethylamino]-propyl}-N-[2-(5-fluoro-2-methyl-phenyl)-ethyl]-benzamide

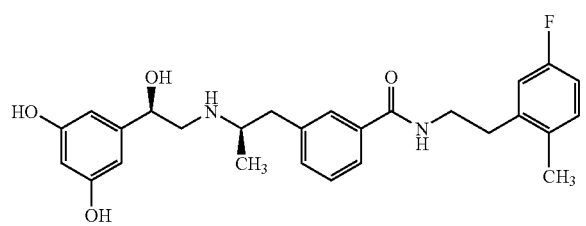

The title compound was prepared from the compound of preparation 106 using the method described for example 12 and was isolated as a white foam.

$^1$H NMR (400 MHz, CD$_3$OD) δ 1.06 (3H, d), 2.33 (3H, s), 2.62 (1H, m), 2.76 (1H, m), 2.80 (2H, m), 2.94 (3H, m), 3.58 (2H, t), 4.55 (1H, m), 6.17 (1H, m), 6.26 (2H, s), 6.82 (1H, m), 6.93 (1H, m), 7.12 (1H, m), 7.35 (2H, m), 7.57 (1H, s), 7.61 (1H, m). LRMS: m/z APCl 467 [M+H$^+$], 465 [M−H$^−$].

EXAMPLE 78

3-{2-[2-(3,5-Dihydroxy-phenyl)-2-hydroxy-ethylamino]-propyl}-N-[2-(2-trifluoromethyl-phenyl)-ethyl]-benzamide

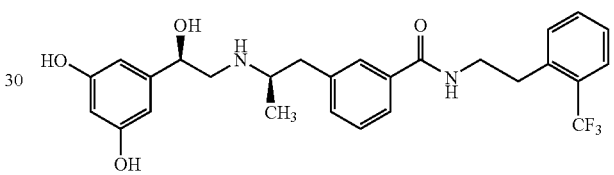

The title compound was prepared from the compound of preparation 107 using the method described for example 12 and was isolated as a white foam.

$^1$H NMR (400 MHz, CD$_3$OD) δ 1.06 (3H, d), 2.62 (1H, m), 2.75 (1H, m), 2.82 (2H, m), 2.98 (1H, m), 3.12 (2H, t), 3.62 (2H, t), 4.56 (1H, m), 6.17 (1H, m), 6.26 (2H, s), 7.35 (3H, m), 7.50 (2H, m), 7.61 (3H, m). LRMS: m/z APCl 503 [M+H$^+$], 501 [M−H$^−$].

EXAMPLE 79

3-{2-[2-(3,5-Dihydroxy-phenyl)-2-hydroxy-ethylamino]-propyl}-N-(2-naphthalen-1-yl-ethyl)-benzamide

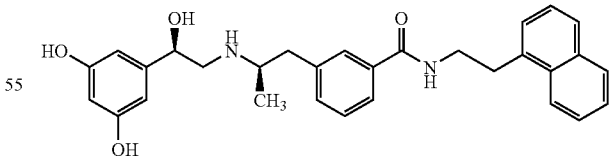

The title compound was prepared from the compound of preparation 108 using the method described for example 12 and was isolated as a white foam.

$^1$H NMR (400 MHz, CD$_3$OD) δ 1.05 (3H, d), 2.60 (1H, m), 2.75 (3H, m), 2.96 (1H, m), 3.40 (2H, t), 3.70 (2H, t), 4.57 (1H, m), 6.17 (1H, m), 6.28 (2H, s), 7.35 (5H, m), 7.48 (3H, m), 7.59 (1H, m), 7.75 (1H, m), 7.84 (1H, m), 8.23 (1H, m). LRMS: m/z APCl 485 [M+H$^+$], 483 [M−H$^−$].

EXAMPLE 80

3-{2-[2-(3,5-Dihydroxy-phenyl)-2-hydroxy-ethylamino]-propyl}-N-[2-(2,4,5-trimethyl-phenyl)-ethyl]-benzamide

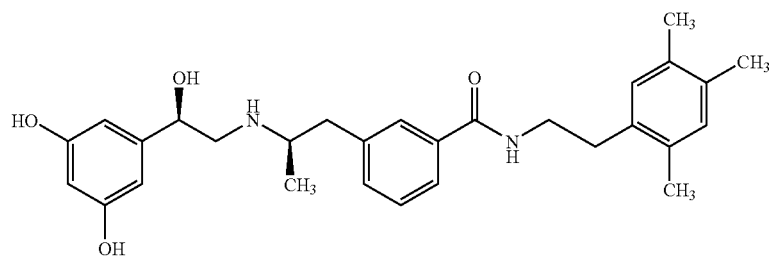

The title compound was prepared from the compound of preparation 109 using the method described for example 12 and was isolated as a white foam.

$^1$H NMR (400 MHz, CD$_3$OD) δ 1.05 (3H, d), 2.17 (3H, s), 2.17 (6H, s), 2.27 (3H, s), 2.62 (1H, m), 2.75 (1H, m), 2.81 (4H, m), 2.98 (1H, m), 3.50 (2H, t), 4.55 (1H, m), 6.17 (1H, m), 6.26 (2H, s), 6.88 (1H, s), 6.91 (1H, s), 7.35 (2H, m), 7.38 (1H, s), 7.40 (1H, m). LRMS: m/z APCl 477 [M+H$^+$], 475 [M−H$^-$].

EXAMPLE 81

3-{2-[2-(3,5-Dihydroxy-phenyl)-2-hydroxy-ethylamino]-propyl}-N-[2-(2,3-dimethyl-phenyl)-ethyl]-benzamide

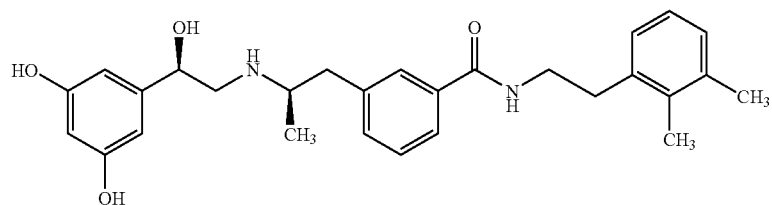

The title compound was prepared from the compound of preparation 110 using the method described for example 12 and was isolated as a white foam.

$^1$H NMR (400 MHz, CD$_3$OD) δ 1.05 (3H, d), 2.26 (3H, s), 2.26 (3H, s), 2.62 (1H, m), 2.75 (1H, m), 2.81 (2H, m), 2.95 (3H, m), 3.54 (2H, t), 4.56 (1H, m), 6.17 (1H, m), 6.26 (2H, s), 6.98 (3H, m), 7.35 (2H, m), 7.38 (1H, s), 7.41 (1H, m). LRMS: m/z APCl 463 [M+H$^+$], 461 [M−H$^-$].

EXAMPLE 82

3-{2-[2-(3,5-Dihydroxy-phenyl)-2-hydroxy-ethylamino]-propyl}-N-[2-(2-hydroxy-3-chloro-phenyl)-ethyl]-benzamide

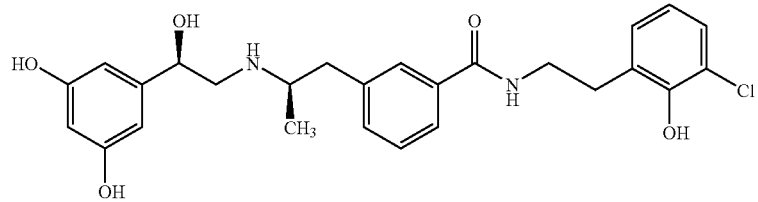

The title compound was prepared from the compound of preparation 111 using the method described for example 12 and was isolated as a white foam.
$^1$H NMR (400 MHz, CD$_3$OD) δ 1.06 (3H, d), 2.62 (1H, m), 2.75 (1H, m), 2.81 (2H, m), 2.95 (3H, m), 3.60 (2H, t), 4.56 (1H, m), 6.17 (1H, m), 6.26 (2H, s), 6.74 (1H, m), 7.06 (1H, m), 7.17 (1H, m), 7.35 (2H, m), 7.57 (1H, s), 7.60 (1H, m). LRMS: m/z APCl 485 [M+H$^+$], 483 [M–H$^-$].

EXAMPLE 83

3-{2-[2-(3,5-Dihydroxy-phenyl)-2-hydroxy-ethylamino]-propyl}-N-[2-(4-chloro-phenyl)-ethyl]-benzamide

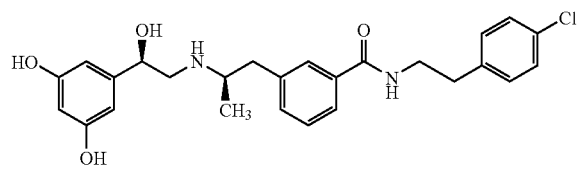

The title compound was prepared from the compound of preparation 112 using the method described for example 12 and was isolated as a white foam.
$^1$H NMR (400 MHz, CD$_3$OD) δ 1.05 (3H, d), 2.62 (1H, m), 2.75 (1H, m), 2.81 (2H, m), 2.95 (3H, m), 3.58 (2H, t), 4.56 (1H, m), 6.17 (1H, m), 6.26 (2H, s), 7.30 (6H, m), 7.58 (2H, m). LRMS: m/z APCl 469 [M+H$^+$], 467 [M–H$^-$].

EXAMPLE 84

3-{2-[2-(3,5-Dihydroxy-phenyl)-2-hydroxy-ethylamino]-propyl}-N-[2-(2-hydroxy-5-chloro-phenyl)-ethyl]-benzamide

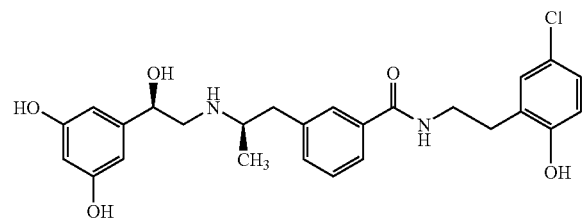

The title compound was prepared from the compound of preparation 113 using the method described for example 12 and was isolated as a white foam.
$^1$H NMR (400 MHz, CD$_3$OD) δ 1.06 (3H, d), 2.63 (1H, m), 2.77 (1H, m), 2.86 (4H, m), 3.00 (1H, m), 3.58 (2H, t), 4.57 (1H, m), 6.17 (1H, m), 6.26 (2H, s), 6.78 (1H, m), 7.00 (1H, m), 7.09 (1H, m), 7.30 (2H, m), 7.57 (1H, s), 7.59 (1H, m). LRMS: m/z APCl 485 [M+H$^+$], 483 [M–H$^-$].

EXAMPLE 85

3-{2-[2-(3,5-Dihydroxy-phenyl)-2-hydroxy-ethylamino]-propyl}-N-[2-(2-chloro-4-fluoro-phenyl)-ethyl]-benzamide

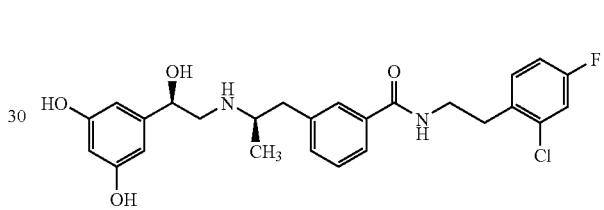

The title compound was prepared from the compound of preparation 114 using the method described for example 12 and was isolated as a white foam.
$^1$H NMR (400 MHz, CD$_3$OD) δ 1.05 (3H, d), 2.62 (1H, m), 2.75 (1H, m), 2.83 (2H, m), 3.00 (1H, m), 3.05 (2H, t), 3.62 (2H, t), 4.56 (1H, m), 6.17 (1H, m), 6.26 (2H, s), 6.99 (1H, m), 7.19 (1H, m), 7.35 (3H, m), 7.60 (2H, m). LRMS: m/z APCl 487 [M+H$^+$], 485 [M–H$^-$].

EXAMPLE 86

2-(3-{2-[2-(3,5-Dihydroxy-phenyl)-2-hydroxy-ethylamino]-2-methyl-propyl}-phenyl)-N-(2-methyl-benzyl)-acetamide

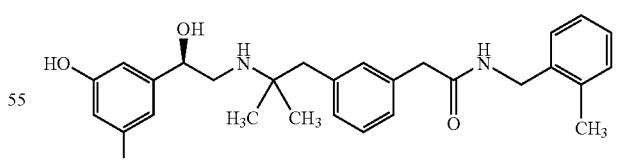

The title compound was prepared from the compound of preparation 115 using the method described for example 34 and was isolated as a white foam.
$^1$H NMR (400 MHz, CD$_3$OD) δ 1.04 (3H, s), 1.05 (3H, s), 2.22 (3H, s), 2.73 (3H, m), 2.83 (1H, m), 3.56 (2H, s), 4.37 (2H, s), 4.55 (1H, m), 6.18 (1H, m), 6.36 (2H, s), 7.04 (1H, d), 7.10 (6H, m), 7.21 (1H, t). LRMS: m/z electrospray 465 [M+H$^+$], 462 [M–H$^-$].

EXAMPLE 87

2-(3-{2-[2-(3,5-Dihydroxy-phenyl)-2-hydroxy-ethylamino]-2-methyl-propyl}-phenyl)-N-(3-methyl-benzyl)-acetamide

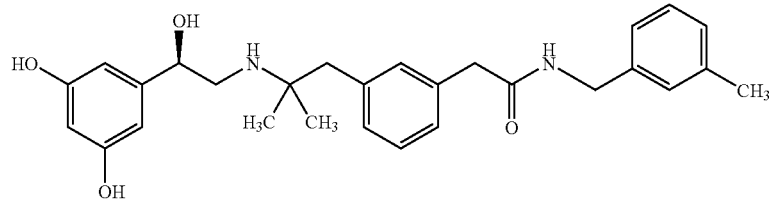

The title compound was prepared from the compound of preparation 116 using the method described for example 34 and was isolated as a white foam.

$^1$H NMR (400 MHz, CD$_3$OD) δ 1.04 (3H, s), 1.05 (3H, s), 2.23 (3H, s), 2.73 (3H, m), 2.83 (1H, m), 3.56 (2H, s), 4.31 (2H, s), 4.55 (1H, m), 6.18 (1H, m), 6.36 (2H, s), 7.04 (4H, m), 7.15 (3H, m), 7.21 (1H, t). LRMS: m/z electrospray 465 [M+H$^+$], 462 [M−H$^-$].

EXAMPLE 88

2-(3-{2-[2-(3,5-Dihydroxy-phenyl)-2-hydroxy-ethylamino]-2-methyl-propyl}-phenyl)-N-(4-methyl-benzyl)-acetamide

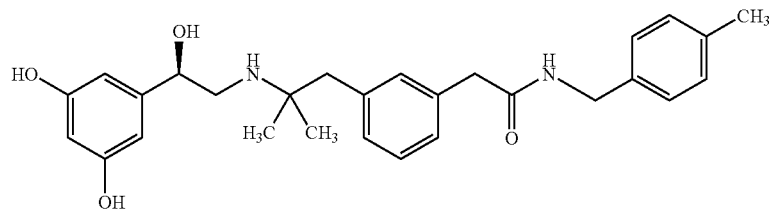

The title compound was prepared from the compound of preparation 117 using the method described for example 34 and was isolated as a white foam.

$^1$H NMR (400 MHz, CD$_3$OD) δ 1.04 (3H, s), 1.05 (3H, s), 2.27 (3H, s), 2.73 (3H, m), 2.83 (1H, m), 3.56 (2H, s), 4.28 (2H, s), 4.55 (1H, m), 6.18 (1H, m), 6.36 (2H, s), 7.04 (1H, d), 7.10 (5H, m), 7.17 (1H, d), 7.22 (1H, m). LRMS: m/z electrospray 465 [M+H$^+$], 462 [M−H$^-$].

EXAMPLE 89

2-(3-{2-[2-(3,5-Dihydroxy-phenyl)-2-hydroxy-ethylamino]-2-methyl-propyl}-phenyl)-N-(2-methoxy-benzyl)-acetamide

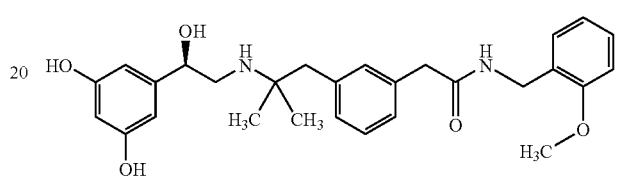

The title compound was prepared from the compound of preparation 118 using the method described for example 34 and was isolated as a white foam.

$^1$H NMR (400 MHz, CD$_3$OD) δ 1.04 (3H, s), 1.05 (3H, s), 2.68 (2H, t), 2.77 (1H, m), 2.83 (1H, m), 3.56 (2H, s), 3.79 (3H, s), 4.37 (2H, s), 4.55 (1H, m), 6.18 (1H, m), 6.37 (2H, s), 6.82 (1H, m), 6.92 (1H, d), 7.03 (1H, d), 7.12 (3H, m), 7.22 (2H, m). LRMS: m/z electrospray 480 [M+H$^+$], 478 [M−H$^-$].

EXAMPLE 90

2-(3-{2-[2-(3,5-Dihydroxy-phenyl)-2-hydroxy-ethylamino]-2-methyl-propyl}-phenyl)-N-(4-methoxy-benzyl)-acetamide

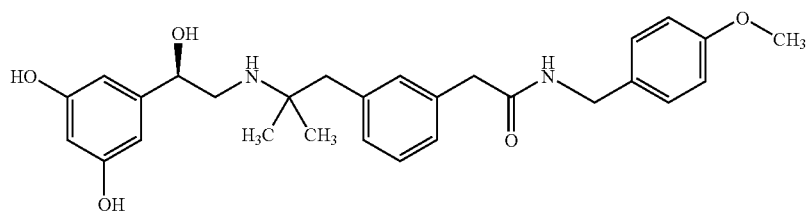

The title compound was prepared from the compound of preparation 119 using the method described for example 34 and was isolated as a white foam.

$^1$H NMR (400 MHz, CD$_3$OD) δ 1.04 (3H, s), 1.05 (3H, s), 2.68 (3H, m), 2.83 (1H, m), 3.56 (2H, s), 3.77 (3H, s), 4.27 (2H, s), 4.55 (1H, m), 6.18 (1H, m), 6.36 (2H, s), 6.92 (2H, d), 7.04 (2H, d), 7.17 (4H, m), 7.21 (1H, m). LRMS: m/z electrospray 481 [M+H$^+$], 478 [M–H$^-$].

EXAMPLE 91

2-(3-{2-[2-(3,5-Dihydroxy-phenyl)-2-hydroxy-ethylamino]-2-methyl-propyl}-phenyl)-N-(2,3-dimethyl-benzyl)-acetamide

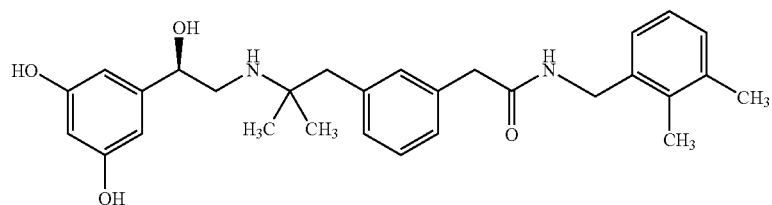

The title compound was prepared from the compound of preparation 120 using the method described for example 34 and was isolated as a white foam.

$^1$H NMR (400 MHz, CD$_3$OD) δ 1.04 (3H, s), 1.05 (3H, s), 2.15 (3H, s), 2.24 (3H, s), 2.68 (3H, m), 2.83 (1H, m), 3.53 (2H, s), 4.37 (2H, s), 4.55 (1H, m), 6.18 (1H, m), 6.36 (2H, s), 7.02 (1H, d), 7.08 (3H, m), 7.11 (1H, m), 7.17 (1H, d), 7.21 (1H, m). LRMS: m/z electrospray 478 [M+H$^+$], 476 [M–H$^-$].

EXAMPLE 92

2-(3-{2-[2-(3,5-Dihydroxy-phenyl)-2-hydroxy-ethylamino]-2-methyl-propyl}-phenyl)-N-(3,4-dimethyl-benzyl)-acetamide

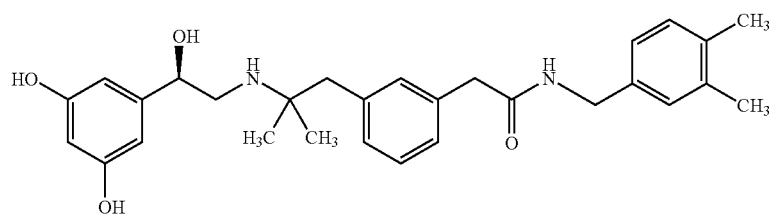

The title compound was prepared from the compound of preparation 121 using the method described for example 34 and was isolated as a white foam.

$^1$H NMR (400 MHz, CD$_3$OD) δ 1.04 (3H, s), 1.05 (3H, s), 2.19 (3H, s), 2.19 (3H, s), 2.68 (3H, m), 2.83 (1H, m), 3.54 (2H, s), 4.27 (2H, s), 4.55 (1H, m), 6.18 (1H, m), 6.36 (2H, s), 6.96 (1H, d), 6.97 (1H, s), 7.06 (2H, m), 7.11 (1H, m), 7.18 (1H, m), 7.21 (1H, m). LRMS: m/z electrospray 477 [M+H$^+$], 475 [M–H$^-$].

EXAMPLE 93

2-(3-{2-[2-(3,5-Dihydroxy-phenyl)-2-hydroxy-ethylamino]-2-methyl-propyl}-phenyl)-N-(2-chloro-6-methyl-benzyl)-acetamide

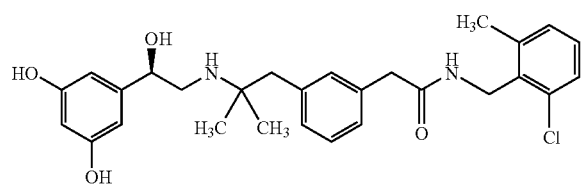

The title compound was prepared from the compound of preparation 122 using the method described for example 34 and was isolated as a white foam.

$^1$H NMR (400 MHz, CD$_3$OD) δ 1.04 (3H, s), 1.05 (3H, s), 2.37 (3H, s), 2.68 (3H, m), 2.83 (1H, m), 3.47 (2H, s), 4.53 (2H, s), 4.55 (1H, m), 6.18 (1H, m), 6.36 (2H, s), 7.04 (1H, d), 7.09 (1H, m), 7.18 (4H, m), 7.21 (1H, m). LRMS: m/z electrospray 497 [M+H$^+$].

EXAMPLE 94

2-(3-{2-[2-(3,5-Dihydroxy-phenyl)-2-hydroxy-ethylamino]-2-methyl-propyl}-phenyl)-N-(3-chloro-4-methyl-benzyl)-acetamide

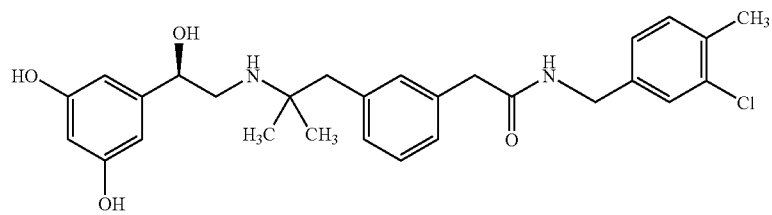

The title compound was prepared from the compound of preparation 123 using the method described for example 34 and was isolated as a white foam.

$^1$H NMR (400 MHz, CD$_3$OD) δ 1.04 (3H, s), 1.05 (3H, s), 2.31 (3H, s), 2.68 (3H, m), 2.83 (1H, m), 3.56 (2H, s), 4.28 (2H, s), 4.53 (1H, m), 6.18 (1H, m), 6.36 (2H, s), 7.04 (1H, d), 7.11 (1H, s), 7.18 (1H, m), 7.21 (4H, m). LRMS: m/z electrospray 497 [M+H$^+$].

EXAMPLE 95

2-(3-{2-[2-(3,5-Dihydroxyphenyl)-2-hydroxyethylamino]-2-methylpropyl}phenyl)-N-[2-(6-methoxynaphthalen-2-yl)ethyl]acetamide

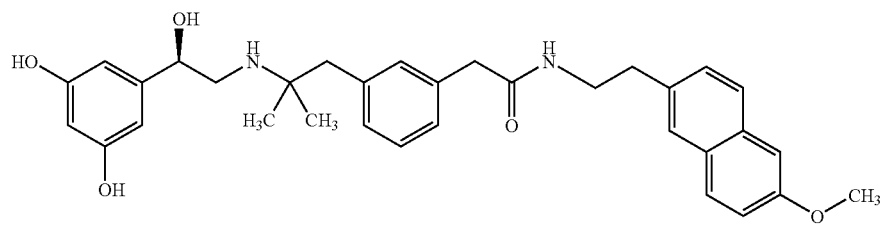

The title compound was prepared from the compound of preparation 124 using the method described for example 34 and was isolated as a white foam.

$^1$H NMR (400 MHz, CD$_3$OD) δ 1.07 (3H, s), 1.07 (3H, s), 2.63 (2H, m), 2.81 (2H, m), 3.44 (2H, s), 3.51 (2H, m), 3.64 (2H, s), 3.87 (3H, s), 4.58 (1H, m), 6.18 (1H, m), 6.36 (2H, s), 7.04 (6H, m), 7.24 (1H, d), 7.47 (1H, s), 7.63 (2H, m). LRMS: m/z electrospray 543 [M+H$^+$].

EXAMPLE 96

N-(2-Chlorobenzyl)-3-(3-{2-[2-(3,5-dihydroxyphenyl)-2-hydroxyethylamino]propyl}phenyl)propionamide

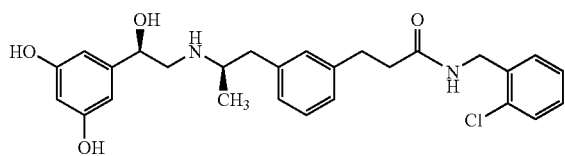

Prepared according to the procedure used for example 12, using preparation 142.
$^1$H NMR (400 MHz, CD$_3$OD) 1.04 (3H, d), 2.50-2.72 (3H, m), 2.65-2.75 (2H, m), 2.76-2.85 (1H, m), 2.86-2.95 (3H, m), 4.40 (2H, s), 4.53 (1H, m), 6.16 (1H, m), 6.26 (2H, s), 6.94-7.08 (4H, m), 7.13-7.24 (3H, m), 7.35 (1H, m); LRMS APCl m/z 483 [M+H]$^+$

EXAMPLE 97

N-(2,6-Dichlorobenzyl)-3-(3-{2-[2-(3,5-dihydroxyphenyl)-2-hydroxyethylamino]propyl}phenyl)propionamide

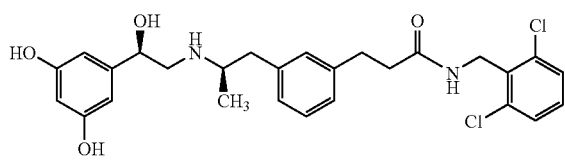

Prepared according to the procedure used for example 12, using preparation 143.
$^1$H NMR (400 MHz, CD$_3$OD) δ: 1.04 (3H, d), 2.42-2.58 (3H, m), 2.62-2.75 (2H, m), 2.76-2.95 (4H, m), 4.53 (1H, m), 4.62 (2H, s), 6.16 (1H, m), 6.25 (2H, s), 6.92 (1H, m), 6.96 (1H, s), 7.01 (1H, m), 7.13 (1H, t), 7.26 (1H, t), 7.38 (2H, m); LRMS APCl m/z 517 [M+H]$^+$

EXAMPLE 98

1-(3,4-Dihydro-1H-isoquinolin-2-yl)-3-(3-{2-[2-(3,5-dihydroxyphenyl)-2-hydroxyethylamino]propyl}phenyl)propan-1-one

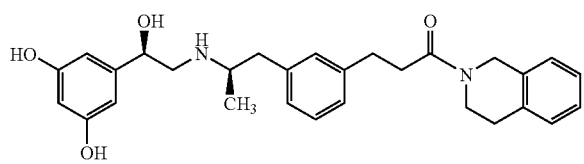

Prepared according to the procedure used for example 12, using preparation 144.
$^1$H NMR (400 MHz, CD$_3$OD) δ: 1.03 (3H, d), 2.65-2.95 (11H, m), 3.62-3.75 (2H, m), 4.46-4.68 (3H, m), 6.16 (1H, m), 6.24 (2H, s), 6.84-7.19 (8H, m); LRMS APCl m/z 475 [M+H]$^+$

EXAMPLE 99

N-(2-Chloro-4-fluorobenzyl)-2-(3-{2-[2-(3,5-dihydroxyphenyl)-2-hydroxyethylamino]propyl}phenyl)acetamide

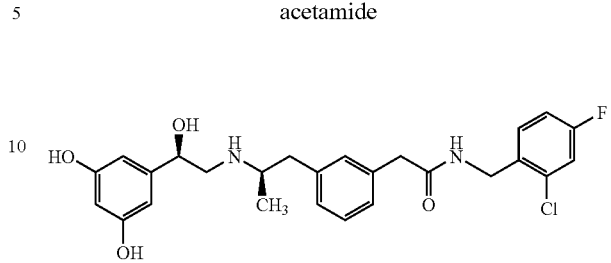

The title compound was prepared from the compound of preparation 145 using the method described for example 34.
$^1$H NMR (400 MHz, CD$_3$OD) δ 1.00 (3H, d), 2.60-2.65 (1H, m), 2.64-2.68 (2H, m), 2.83-2.93 (1H, m), 3.48 (2H, s), 4.86 (2H, s), 4.47-4.50 (1H, m), 6.11 (1H, s), 6.21 (2H, m), 6.99-7.83 (7H, m). LRMS: m/z APCl 687 [M+H$^+$].

EXAMPLE 100

N-(4-Bromobenzyl)-2-(3-{2-[2-(3,5-dihydroxyphenyl)-2-hydroxyethylamino]-2-methylpropyl}phenyl)acetamide

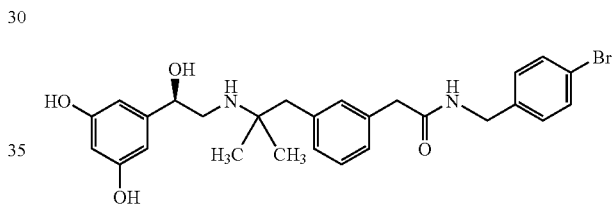

The title compound was prepared from the compound of preparation 146 using the method described for example 34.
$^1$H NMR (400 MHz, CD$_3$OD) δ: 1.07 (d, 6H), 2.63-2.78 (m, 3H), 2.84 (t, 1H), 3.57 (s, 2H), 4.31 (s, 2H), 4.53-4.57 (m, 1H), 6.18 (s, 1H), 6.37 (s, 2H), 7.05 (d, 1H), 7.16 (t, 4H), 7.22 (t, 1H), 7.42 (d, 2H); LRMS APCl m/z 529 [M+H]$^+$.

EXAMPLE 101

2-(3-{2-[2-(3,5-Dihydroxyphenyl)-2-hydroxyethylamino]-2-methylpropyl}phenyl)-N-(3,4-dimethylphenyl)acetamide

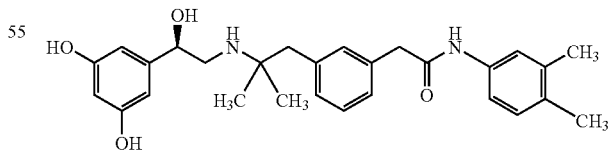

The title compound was prepared from the compound of preparation 147 using the method described for example 34.
$^1$H NMR (400 MHz, CD$_3$OD) δ: 1.05 (d, 6H), 2.22 (d, 6H), 2.66-2.78 (m, 3H), 2.83 (t, 1H), 3.62 (s, 2H), 4.56-4.59 (m, 1H), 6.18 (s, 1H), 6.32 (s, 2H), 7.04 (t, 2H), 7:18-7.24 (m, 4H), 7.31 (s, 1H); LRMS APCl m/z 463 [M+H]$^+$.

EXAMPLE 102

2-(3-{2-[2-(3,5-Dihydroxyphenyl)-2-hydroxyethylamino]propyl}phenyl)-N-(2,3-dimethylbenzyl)acetamide

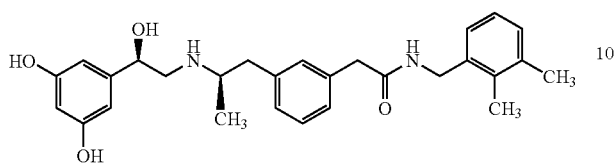

The title compound was prepared from the compound of preparation 148 using the method described for example 12.

$^1$H NMR (400 MHz, CD$_3$OD) δ: 0.99 (3H, s), 2.20 (3H, s), 2.48 (1H, dd), 2.61-2.67 (2H, m), 2.72 (1H, dd), 2.80 (1H, dt), 3.45 (2H, s), 4.31 (2H, s), 4.44 (1H, dd), 6.09 (1H, t), 6.19 (1H, s), 6.20 (1H, s), 6.92-7.17 (7H, m); LRMS APCl m/z 462 [M+H]$^+$.

EXAMPLE 103

2-(3-{2-[2-(3,5-Dihydroxyphenyl)-2-hydroxyethylamino]propyl}phenyl)-N-(4-fluorobenzyl)acetamide

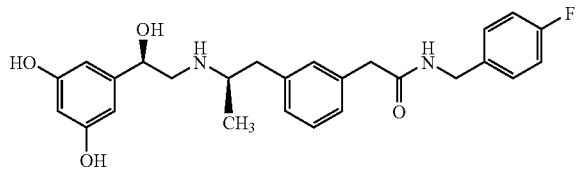

The title compound was prepared from the compound of preparation 149 using the method described for example 12.

$^1$H NMR (400 MHz, CD$_3$OD) δ: 0.99 (3H, d), 2.49 (1H, dd), 2.60-2.66 (2H, m), 2.74 (1H, dd), 2.82-2.89 (1H, m), 3.46 (2H, s), 4.27 (2H, s), 4.46 (1H, dd), 6.12 (1H, t), 6.21 (1H, s), 6.22 (1H, s), 6.91-6.98 (3H, m), 7.02-7.07 (2H, m), 7.03-7.21 (3H, m); LRMS APCl m/z 451 [M+H]$^+$.

EXAMPLE 104

2-(3-{2-[2-(3,5-Dihydroxyphenyl)-2-hydroxyethylamino]propyl}phenyl)-1-(4-pyridin-2-ylpiperazin-1-yl)ethanone

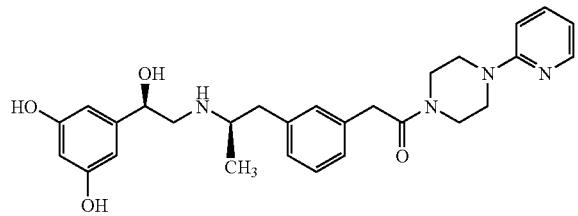

The title compound was prepared from the compound of preparation 150 using the method described for example 12.

$^1$H NMR (400 MHz, CD$_3$OD) δ: 1.05 (3H, d), 2.59 (1H, dd), 2.78-2.93 (3H, m), 3.08-3.15 (1H, m), 3.31 (2H, t), 3.41 (2H, t), 3.59 (2H, t), 3.66 (2H, t), 3.77 (2H, s), 4.55 (1H, dd), 6.13 (1H, t), 6.25 (1H, s), 6.26 (1H, s), 6.62-6.65 (1H, m), 6.73 (1H, d), 7.02-7.11 (3H, m), 7.20 (1H, t), 7.48 (1H, dt), 8.01 (1H, bd); LRMS APCl m/z 491 [M+H]$^+$.

EXAMPLE 105

2-(3-{2-[2-(3,5-Dihydroxyphenyl)-2-hydroxyethylamino]-2-methylpropyl}phenyl)-N-(2-phenylpropyl)acetamide

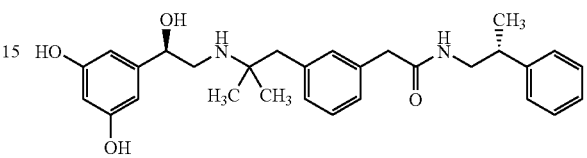

The title compound was prepared from the compound of preparation 151 using the method described for example 12.

$^1$H NMR (400MHZ, CD$_3$OD) δ: 0.92 (3H, D),1.06 (3H, D), 2.40 (1H, DD), 2.53-2.59 (2H, M), 2.66 (1H, DD), 2.74-2.83 (2H, M), 3.14-3.24 (2H, M), 3.27 (2H, S), 4.38 (1H, DD), 6.02 (1H, T), 6.13 (1H, S), 6.13 (1H, S), 6.83-6.90 (2H, M), 6.98-7.07 (4H, M), 7.08-7.13 (92H, M); LRMS APCl M/Z 463 [M+H]$^+$.

The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-pig Trachea

Male, Dunkin-Hartley guinea pigs (475-525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3-4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma 17378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30-45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma 15627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The $EC_{50}$ value for beta-2 agonist according to the present invention refers to the concentration of compound required to produce half maximal effect. Data for beta-2 agonists according to the present invention are then expressed as relative potency to isoprenaline defined by the ratio ($EC_{50}$ beta-2 agonist)/(EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β2 antagonist) which results in the case of a beta-2 mediated effect in a rightward-shift of the test compound dose response curve.

According to another alternative, the agonist potency for the β2 receptor of the compounds of the formula (1) may also be determined by the measure of the concentration of compound according to the present invention required to produce half maximal effect ($EC_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46-50, 1987 and Bouvier et al., Mol Pharmacol 33: 133-139 1988 CHOhβ2) were grown in Dulbeccos MEM/NUT MIX F12 (Gibco, 21331-020) supplemented with 10% foetal bovine serum (Sigma, F4135, Lot 90K8404 Exp September 2004), 2 mM glutamine (Sigma, G7513), 500 μg/ml geneticin (Sigma, G7034) and 10 μg/ml puromycin (Sigma, P8833). Cells were seeded to give about 90% confluency for testing.

Assay Method

25 μl/well each dose of compound was transferred into a cAMP-Flashplate® (NEN, SMP004B), with 1% DMSO as basal controls and 100 nM Isoprenaline as max controls. This was diluted 1:2 by the addition of 25 μl/well PBS. Cells were trypsinised (0.25% Sigma, T4049), washed with PBS (Gibco, 14040-174) and resuspended in stimulation buffer (NEN, SMP004B) to give $1\times10^6$ cells/ml CHOhB2. Compounds were incubated with 50 μl /well cells for 1 hour. Cells were then lysed by the addition of 100 μl/well detection buffer (NEN, SMP004B) containing 0.18 μCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the compounds of formula (1) according to the present invention that are illustrated in examples 1 to 105 show a β2 cAMP $EC_{50}$ below 30 nM.

What is claimed is:

1. A compound of formula (1),

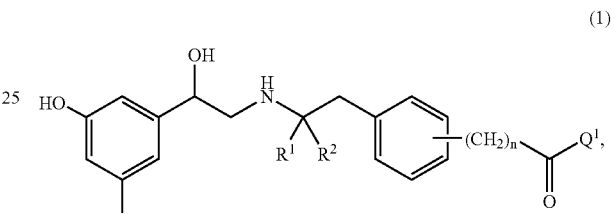

(1)

or a pharmaceutically acceptable salt thereof,
wherein the $(CH_2)_n$—C(=O)Q$^1$ group is in the meta or para position;
R$^1$ and R$^2$ are independently H or $C_1$-$C_4$ alkyl;
n is 0, 1 or 2;
Q$^1$ is *—NR$^8$-Q$^2$-A;
Q$^2$ is a single bond or $C_1$-$C_4$ alkylene optionally substituted with OH;
R$^8$ is H or $C_1$-$C_4$ alkyl;
A is

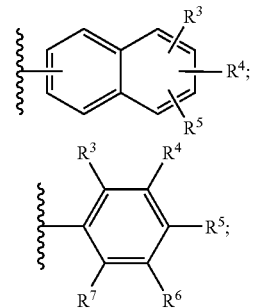

R$^3$, R$^4$, R$^5$, R$^6$ and R$^7$ are independently H, $C_1$-$C_4$ alkyl, OR$^9$, SR$^9$, SOR$^9$, SO$_2$R$^9$, halo, CN, CF$_3$, OCF$_3$, SO$_2$NR$^9$R$^{10}$, COOR$^9$, CONR$^9$R$^{10}$, NR$^9$R$^{10}$, NHCOR$^{10}$ or phenyl optionally substituted with OH;
R$^9$ and R$^{10}$ are independently H or $C_1$-$C_4$ alkyl; and
* represents the attachment point to the carbonyl group.

2. A compound of claim 1 or a pharmaceutically acceptable salt thereof wherein the $(CH_2)_n$—C(=O)Q$^1$ group is in the meta or para position;

$R^1$ and $R^2$ are independently H or $C_1$-$C_4$ alkyl;
n is 0, 1 or 2;
$Q^1$ is *—$NR^8$-$Q^2$-A;
$Q^2$ is $C_1$-$C_4$ alkylene; and
A is

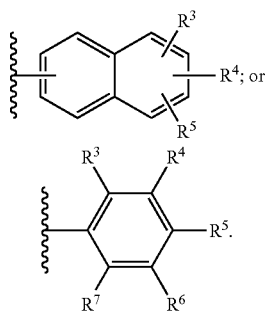

3. A compound of claim 1 or a pharmaceutically acceptable salt thereof wherein A is naphthyl optionally substituted with $OR^9$.

4. A compound of claim 2 or a pharmaceutically acceptable salt thereof wherein $Q^1$ is *—NH-$Q^2$-A; and
A is

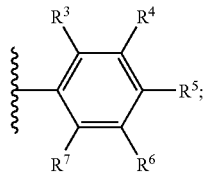

provided at least 2 of $R^3$, $R^4$, $R^5$, $R^6$ and $R^7$ are H.

5. A compound of claim 1 or a pharmaceutically acceptable salt thereof wherein $Q^2$ is —$CH_2$—, —$(CH_2)_2$—, —$(CH_2)_3$—, —$CH(CH_3)$—, —$CH_2CH(CH_3)$— or $C(CH_3)_2$—.

6. A compound of claim 1 or a pharmaceutically acceptable salt thereof wherein $R^1$ is H or $CH_3$ and $R^2$ is $CH_3$.

7. A compound of claim 1 or a pharmaceutically acceptable salt thereof wherein n is 0 or 1.

8. The (R,R)-stereoisomer of a compound of claim 1 or a pharmaceutically acceptable salt thereof.

9. A compound of claim 1 or a pharmaceutically acceptable salt thereof wherein the $(CH_2)_n$—C(=O)$Q^1$ group is in the meta position.

10. A pharmaceutical composition comprising an effective amount of a compound of claim 1 or a pharmaceutically acceptable salt thereof and a pharmaceutically acceptable excipient or additive.

11. A method of treating a disease, disorder or condition in a mammal, wherein said treatment is palliative treatment, said method comprising administering to said mammal in need thereof (a) a therapeutically effective amount of a compound of claim 1 or a pharmaceutically acceptable salt thereof or (b) a therapeutically effective amount of a compound of claim 1 or a pharmaceutically acceptable salt thereof and a pharmaceutically acceptable excipient, wherein said disease, disorder or condition is asthma, chronic obstructive pulmonary disease, bronchitis, chronic or acute bronchoconstriction, adult respiratory distress syndrome, acute lung injury or bronchiectasis.

12. A method of claim 11 wherein said asthma is selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, bronchitic asthma, emphysematous asthma, exercise-induced asthma, allergen induced asthma, cold air induced asthma, infective asthma caused by bacterial, fungal, protozoal, or viral infection, non-allergic asthma, wheezy infant syndrome ; said bronchitis is selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis; and said bronchiectasis is cylindric bronchiectasis, sacculated bronchiectasis, fusiform bronchiectasis, capillary bronchiectasis, cystic bronchiectasis, dry bronchiectasis and follicular bronchiectasis.

* * * * *